United States Patent [19]

Kishimoto et al.

[11] Patent Number: 4,794,108
[45] Date of Patent: Dec. 27, 1988

[54] 1-CARBOXYMETHOXY ACETIDINONES AND THEIR PRODUCTION

[75] Inventors: Shoji Kishimoto, Takarazuka; Michiyuki Sendai; Michihiko Ochiai, both of Suita, all of Japan

[73] Assignee: Takeda Chemical Industries, Ltd., Osaka, Japan

[21] Appl. No.: 651,033

[22] Filed: Sep. 14, 1984

[30] Foreign Application Priority Data

Apr. 24, 1984 [WO] PCT Int'l Appl. ............. 84/00215
Apr. 24, 1984 [WO] PCT Int'l Appl. ............. 84/00215

[51] Int. Cl.$^4$ ............. A61K 31/425; C07D 205/08; C07D 417/12; C07D 303/48
[52] U.S. Cl. ............. 514/210; 540/355; 549/549; 560/150; 560/159; 562/564
[58] Field of Search ............. 514/210; 260/239 A; 540/355

[56] References Cited

U.S. PATENT DOCUMENTS 4,548,747 10/1985 Zahler ............. 514/210
4,548,751 10/1985 Kimball ............. 514/210

FOREIGN PATENT DOCUMENTS 0051381 5/1982 European Pat. Off. .
3328047 2/1984 Fed. Rep. of Germany .
2125794 3/1984 United Kingdom .
2127411 4/1984 United Kingdom .
2129428 5/1984 United Kingdom .

OTHER PUBLICATIONS

Atherton, Chem. Abs. 101,6897y (1984).
Woulfe et al., Chem. Abs. 102, 6001x (1984).

Primary Examiner—Mark L. Berch
Attorney, Agent, or Firm—Wenderoth, Lind & Ponack

[57] ABSTRACT

A 2-azetidinone derivative having a group of the formula

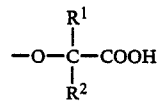

wherein $R^1$ and $R^2$ are the same or different and each represents a hydrogen atom, alkyl, aryl or arylalkyl which may have a substituent at the 1-position and an amino group, at the 3-position, which may be acylated or protected, its salt or ester, and methods of producing the same, (1) a method comprising subjecting a 2-azetidinone derivative having a group of the formula

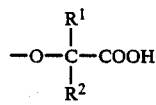

wherein the symbols are as defined above at the 1-position and an amino group at the 3-position, its salt or ester to an acylation or protective-group introduction reaction, and (2) a method comprising reacting a 2-azetidinone derivative having a hydroxy group at the 1-position and an amino group, at the 3-position, which may be acylated or protected, or its salt with a compound of the formula

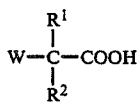

wherein W is a halogen atom; other symbols are as defined above, its salt or ester. The above objective compounds are utilizable as excellent antimicrobial agents or as valuable intermediates for the synthesis of the same.

8 Claims, No Drawings

1-CARBOXYMETHOXY ACETIDINONES AND THEIR PRODUCTION

This invention relates to novel 2-azetidinone derivatives which are excellent antimicrobial substances or useful intermediates for the production thereof, and to processes for producing the same.

In the past, various 2-azetidionone derivatives have been synthesized and reported (Tetrahedron, 34 (1978), 1731-1767; Chemical Reviews, 76 (1976), 113-346; Synthesis, 1973, 327-346, etc.). However, none of the 2-azetidinone derivatives which have at the 1-position a group of the formula:

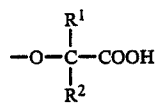

wherein $R^1$ and $R^2$ are the same or different, and each represents a hydrogen atom, an alkyl group or aryl or arylalkyl group which may have a substituent have been known yet.

This invention relates to 2-azetidinone derivatives (hereinafter referred to briefly as "derivatives [I]")having at the 1-position a group of the formula

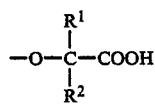

wherein the symbols are as defined above and at the 3-position, an amino group which may optionally be acylated or protected their salts or esters and to processes for producing the same.

The inventors have found that the derivatives [I] can be obtained, for example, by subjecting a 2-azetidinone derivative having at the 1-position a group of the formula

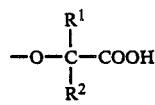

wherein the symbols are as defined above and at the 3-position an amino group, its salt or ester to an acylatron reaction or protective-group introduction reaction, or by reacting a 2-azetidinone derivative having at the 1-position a hydroxy group and at the 3-position an amino group which may optionally be acylated or protected, or its salt with a compound of the formula:

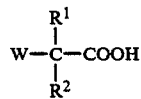 [II]

wherein $R^1$ and $R^2$ are as defined above; W is a halogen atom, its salt or ester, and that the resulting derivatives [I] are excellent antimicrobial substances or useuul intermediates for the synthesis thereof, and accomplished this invention on the basis of these findings.

In the derivatives [I], $R^1$ or $R^2$ are the same or different, and each represents a hydrogen atom, an alkyl group, or aryl or arylalkyl group which may optionally have a substituent. As the alkyl group represented by $R^1$ or $R^2$, use is made of straight or branched alkyl groups, and among others, lower alkyl groups having one to six carbon atoms carbon atoms are preferably. Specially, frequent use is made of methyl, ethyl, n-propyl, isopropyl, n-butyl, isobutyl, n-pentyl, isopentyl, n-hexy,, isohexyl, etc. As the aryl group represented by $R^1$ or $R^2$, those having six to ten carbon atoms are preferred, and use is made for example of phenyl and naphthyl. As the arylalkyl group represented by $R^1$ or $R^2$, use is made for example of the above-described alkyl groups which are substituted with the above-mentioned aryl group, and those having seven to eleven carbon atoms are preferable. Frequent use is made for example of benzyl, phenethyl, phenylpropyl and naphthylmethyl. The aryl group represented by $R^1$ or $R^2$ as well as the aryl group in the arylalkyl group represented by $R^1$ or $R^2$ may have a substituent, and the number of such substituents is preferably one to three. As these substituents, use is made for example of alkyl, halogen (fluorine, chlorine, bromine or iodine), cyano, hydroxy, alkoxy, alkylcarboxyloxy, carbamoyloxy, nitro, amino, alkylcarbonylamino, carboxy, alkoxycarbonyl, carbamoyl, alkylcarbonyl and trifluoromethyl (whereby as the alkyl, use is made of the alkyl groups mentioned above, and as the alkoxy group, use is made of the above-mentioned alkyl groups having an oxygen atom attached thereto; among others, frequent use is made of lower alkoxy groups having one to six carbon atoms such as methoxy, ethoxy, n-propoxy, isopropoxy, n-butoxy, isobutoxy, n-pentoxy, isopentoxy, n-hexyloxy and isohexyloxy).

Specific examples of the substituted aryl or arylalkyl group represented by $R^1$ and $R^2$ include preferably p-hydroxyphenyl, p-methoxyphenyl, 3,4-dihydroxyphenyl, p-chlorophenyl, p-hydroxybenzyl, p-methoxybenzyl, etc.

The derivatives [I] have, at the 3-position, an amino group which may optionally be acylated or protected, whereby as the acyl group in the acylated amino group, use is made for example of the acyl groups which are conventionally known as substituents on the 6-amino group of penicillin derivatives and the 7-amino group of cephalosporin derivatives. Hereinafter, in this specification, any group "which may optionally have a substituent" will be designated by the group marked with a superscript asterisk "*". For example, "alkyl which may optionally have a substituent" will be represented by "alkyl*". In such cases, the number of the substituents is not restricted to one, and some substituted groups may have a few substituents which may be the same or different. In accordance with this designation system, as the acyl group in the 3-substituent of the derivatives[I], use is made for example of groups of the formula:

 [A]

wherein $R^5$ is a lower alkyl, phenyl* or heterocyclic* group, groups of the formula:

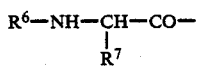 [B]

wherein $R^6$ is hydrogen, an amino acid residue, an amino protecting group or a group represented by the formula $R^8(CH_2)n_1$—CO—in which $R^8$ is a heterocyclic* group; $n_1$ is an integer of 0 to 2; $R^7$ is a lower alkyl, phenyl*, heterocyclic*carbonylamino or heterocyclic* group, groups of the formula:

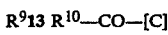

wherein $R^9$ is a group represented by the formula

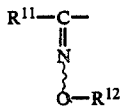

in which $R^{11}$ is an alkyl*, heterocylic* or phenyl* group; $R^{12}$ is hydrogen, lower alkyl, lower alkenyl, phenyl*carbonyl or a group represented by the formula —$R^{13}$—$R^{14}$ (wherein $R^{13}$ is lower alkylene or lower alkenylene; $R^{14}$ is phenyl*, phenyl*carbonyl, carbamoyl, carboxy or its ester or mono- or di- loweralkylamino); $R^{10}$ is a mere linkage or a group represented by the formula

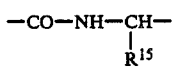

(wherein $R^{15}$ is a lower alkyl, phenyl* or thiazolyl* group), groups of the formula:

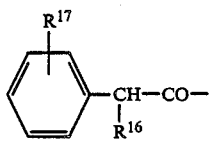
[D]

wherein $R^{16}$ is hydroxy, hydroxysulfonyloxy, carboxy, ureido*, sulfamoyl*, sulfo, phenoxy*carbonyl or formyloxy; $R^{17}$ is hydrogen, lower alkyl, lower alkoxy, halogen, nitro or hydroxy and groups of the formula:

wherein $R^{18}$ is cyano, phenyl*, phenoxy*, lower alkyl*, lower alkenyl* or heterocyclic* group; $R^{19}$ is a mere linkage or —S—.

In the symbols $R^5$ through $R^{19}$, as the alkyl, lower alkyl and halogen, use is made of those described with reference to the above $R^1$ and $R^2$, while as the lower alkoxy group, use is made of the above-mentioned alkoxy groups which have 1 to 6 carbon atoms. As the heterocyclic group, use is made for example of five- to eight-membered rings having one or more hetero atoms such as nitrogen atom (which may be oxidized), oxygen atom and sulfur atom or their fused rings, and frequent use is made for example of 1-, 2- or 3-pyrrolyl, 2- or 3-furyl, 2- or 3-thienyl, 1-, 2- or 3-pyrrolidinyl, 2-, 3- or 4-pyridyl, N-oxido-2-, 3- or 4-pyridyl, 1-, 2-, 3- or 4-piperidinyl, 2-, 3- or 4-pyranyl, 2-, 3- or 4-thiopyranyl, pyradinyl, 2-, 4- or 5-thiazolyl, 2-, 4- or 5-oxazolyl, 3-, 4- or 5-isothiazolyl, 3-, 4- or 5-isoxazolyl, 1-, 2-, 4- or 5-imidazolyl, 1-, 3-, 4- or 5-pyrazolyl, 3- or 4-pyridazinyl, N-oxido-3- or 4-pyridazinyl, 2-, 4- or 5-pyrimidinyl, N-oxido-2-, 4- or 5-pyrimidinyl, 1- or 2-piperazinyl, 4- or 5-(1,2,3-thiadiazolyl) 3- or 5-(1,2,4-thiadiazolyl), 1,3,4-thiadiazolyl, 1,2,5-thiadiazolyl, 4- or 5-(1,2,3-oxadiazolyl), 3- or 5-(1,2,4-oxadiazolyl), 1,3,4oxadiazolyl, 1,2,5-oxadiazolyl, 1- or 4-(1,2,3-triazolyl), 1- or 2-(1,2,4-triazolyl), 1- or 5-(1H-tetrazolyl), 2- or 5-(2-H-tetrazolyl), pyrido[2,3-d]pyrimidyl, benzopyranyl, 1,8-, 1,5-, 1,6-, 1,7-, 2,7- or 2,6-naphthyridyl, quinolyl and thieno[2,3-b] pyridyl. Among others, five or six-membered heterocyclic groups containing one to four hetero atoms selected from oxygen, nitrogen and sulfur atoms, such as thienyl, furyl, thiazolyl, imidazolyl, thiadiazolyl, triazolyl, tetrazolyl, pyridyl and pyrimidinyl, are preferable. As the amino acid residue, use is made for example of glycyl, alanyl, valyl, leucyl, isoleucyl, seryl, threonyl, cysteinyl, cystyl, methionyl, α- or β-aspartyl, α- or γ-glutamyl, lysyl, arginyl, phenyalanyl, phenylglycyl, tyrosyl, histidyl, tryptophanyl and prolyl. As the amino protecting group, use is made of those similar to the amino protecting groups to be described below. The lower alkylene is preferably straight or branched alkylene groups having one to three carbon atoms, and for example, use is made of methylene, ethylene, propylene and isopropylene. The lower alkenyl is preferably alkenyl groups having two to four carbon atoms, and for example, use is made of vinyl, allyl, isopropenyl and 3-butenyl.

The alkenylene is preferably straight or branched lower alkenylene having two to four carbon atoms, and for example, use is made of vinylene and propenylene. As the ester in the carboxy group, use is made for example of lower alkyl esters having one to six carbon atoms such as methyl ester, ethyl ester, propyl ester, n-butyl ester, isobutyl ester and tert-butyl ester. As the substtituents in the heterocyclic* group, phenyl*, thiazolyl*, phenox*carbonyl and phenoxy*, use is made of those such as the substituents on the aryl or arylalkyl mentioned with reference to the foregoing $R^1$ and $R^2$. Furthermore, as the substituent in the thiazolyl*, use may be made for example of acylamino having two to four carbon atoms substituted with alkyl, alkoxy, halogen, hydroxy, amino, etc., wherein acyl is for example acetyl, propionyl, butyryl, etc. As the substituent in the heterocyclic* group, use is made for example of the above-mentioned phenyl substituted with alkyl, alkoxy, halogen, nitro, amino, etc. As the substituent in the ureido*, use is made for example of sulfo in the form of a salt suitably formed with sodium, potassium, etc., crrbamoyl, sulfamoyl, amidino and alkyl having one to three carbon atoms. As the substituent on the sulfamoyl*, use is made for example of lower alkyl having one to three carbon atoms and amidino. As the substituent in the alkyl* and lower alkyl*, use is made for example of the above-described halogen, hydroxy, cyano and trifluoromethyl. As the substituent in the lower alkenyl*, use is made for example of carboxy and cyano.

The formula

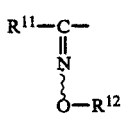

for $R^9$ represents either the syn isomer of the formula

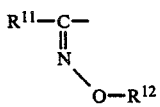

or the anti isomer of the formula

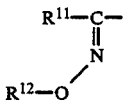

or a mixture thereof.

When amino, carboxy or hydroxy group is present in the above-mentioned substituent represented by $R^5$ through $R^{19}$, such groups may be protected. As the protective group for amino group, use is made for example of the amino-protecting groups to be described below. As the protective group for carboxy group, use can be made of any group which can be conventionally used as a carboxy-protecting group in the fields of β-lactam and organic chemistry, such as ester residues exemplified by methyl, ethyl, n-propyl, isopropyl, tert-butyl, tert-amyl, benzyl, p-nitrobenyl, p-methoxybenzyl, benzhydryl, phenacyl, phenyl, p-nitrophenyl, methoxymethyl, ethoxymethyl, benzyloxymethyl, acetoxymethyl, pivaloyloxymethyl, β-methylsulfonylethyl, methylthiomethyl, trityl, β,β,β-trichloroethyl, β-iodoethyl, 2-trimethylsilylethyl, trimethylsilyl, dimethylsilyl, acetylmethyl, p-nitrobenzoylmethyl, p-mesylbenzoylmethyl, phthalimidomethyl, propionyloxymethyl, mesylmethyl, benzenesulfonylmethyl, phenylthiomethyl and dimethylaminoethyl, and silyl group. Among others, β,β,β-trichloroethll, p-nitrobenzyl, tert-butyl, 2-trimethylsilylethyl and p-methoxybenzyl are preferable. As the protective group for hydroxyl, any group which can be conventionally used as a hydroxyprotecting group in the fields of β-lactam and other organic chemistry can be utilized; for example, use is made of acyl group such as acetyl and chloroacetyl, oxycarbonyl group such as β,β,β-trichloroethoxycarbonyl and 2-trimethylsilylethoxycarbonyl, alkyl or substituted alkyl group such as tert-butyl, benzyl, p-nitrobenzyl, trityl, methylthiomethyl and β-methoxyethoxymethyl, silyl group such as trimethylsilyl and tert-butyldimethylsilyl and pyranyl group such as 2-tetrahydropyranyl and 4-methoxy-4-tetrahydropyranyl. The choice of the above-mentioned hydroxy-protective group is not particularly restricted in the present invention, as is the case with the amino- and carboxy-protective groups.

In the foregoing formulas, as the preferred example of the group represented by the formula [B], use is made of groups of the formula:

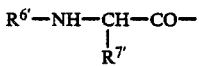 [B]' wherein $R^{6'}$ is an amino-protective group or a group of the formula $R^8$-$(CH_2)_{n_1}$—CO— in which $R^8$ is as defined above; n is an integer of 0 to 2 ; $R^{7'}$ is a phenyl* or heterocyclic* group; as the preferred example of the group represented by the formula [C], use is made of groups of the formula:

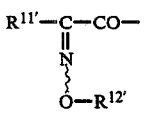 [C]'

[wherein $R^{11'}$ is a heterocyclic* group or phenyl*; $R^{12'}$ is a hydrogen atom, lower alkyl or a group of the formula —$R^{13}$—$R^{14'}$ in which $R^{13}$ is as defined above; $R^{14'}$ is carboxy or its ester; and as the preferable example of the group represented by the formula [E], use is made of groups of the formula:

$$R^{18'}—R^{19}—CH_2—CO—[E]'$$

wherein $R^{18'}$ is a heterocyclic* group; $R^{19}$is as defined above, whereby as the amino-protective group, phenyl*, heterocyclic* group, lower alkyl and ester in the carboxy group represented by $R^{6'}$, $R^{7'}$, $R^{11'}$, $R^{12'}$, $R^{14'}$ and $R^{18'}$, use is made of those as descrieed above.

With reference to the antimicrobial activity, particularly, groups of the formula:

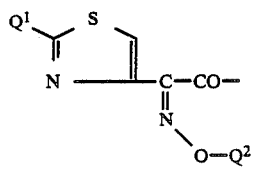

wherein $Q^1$ is an amino or protected amino group; $Q^2$ is lower alkyl, lower alkenyl, a group of the formula —$CH_2COOQ^3$ or a group of the formula —$C(CH_3)_2COOQ^3$, where $COOQ^3$ is carboxy or its ester are more useful as an acyl group for the acylated amino group, i.e. the substituent at the 3-position of the derivatives [I], whereby as the protective group for the protected amino group represented by $Q^1$, lower alkyl and lower alkenyl represented by $Q^2$ and ester in the carboxy represented by $COOQ^3$, use is made of those as described above.

In the above-mentioned acyl group, as the specific example of the acyl group represented by the formula $R^5$—CO—, use is made for example of 3-(2,6-dichlorophenyl)-5-methylisoxazol4-yl-carbonyl and 4-ethyl-2,3-dioxo-1-piperazinocarbonyl.

As the specific example of the acyl group represented by the formula

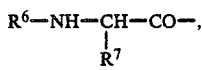

use is made for example of D-alanyl, benzyl Nα-carbobenzoxy-γ-D-glutamyl-D-alanyl, D-phenylglycyl-D-benzyl alanyl, N-carbobenzoxy-D-phenylglycyl, D-alanyl-D-phenylglycyl, γ-D-glutamyl-D-alanyl, 2-(4-ethyl-2,3-dioxo-1-piperazinocarboxamido)2-phenylacetyl, 2-(4-ethyl-2,3-dioxo-1-piperazinocarboxamido)2-(p-sulfoxyphenyl)acetyl, N-(4-ethyl-2,3-dioxo-1-piperazino- carbonyl)-D-alanyl, N-(4-ethyl-2,3-dithioxo-1-piperazinocarbonyl)- D-phenylglycyl, 2,2 -bis-(4-ethyl-2,3-dioxo-1-piperazinocarboxamido acetyl, 2-(2-aminothiazol-4-yl)-2-(4-ethyl-2,3-dioxo-piperazinocarboxamido)acetyl, 2-(4-hydroxy-6-methylnicotinamido)-2-phenylacetyl, 2-(4-hydroxy-6-methylnicotinamido)-2-(p-hydroxyphenyl)acetyl, 2-(5,8-dihydro-2-(4-formyl-1-piperazinyl)-5-oxopyrido[2,3-d]pyrimidine-6-carboxamido)-2-phenylacetyl, 2-(3,5-dioxo1,2,4-triazine-6-carboxamido)-2-(p-hydroxyphenyl)acetyl, 2-(3- furfurylideneamino-2-oxoimidazolidine-1-carboxamido)-2-phenylacetyl 2-(coumarin-3-carboxamido)-2-phenylacetyl, 2-(4-hydroxy-7-methyl1,8-naphthylidine-3-carboxamido)-2-phenylacetyl, 2-(4-hydroxy7-trifluoromethylquinoline-3-carboxamido)-2-phenylacetyl, N-[2-(2-aminothiazol-4-yl)acetyl]-D-phenylglycyl, 2-(6-bromo- 1-ethyl1,4-dihydro-4-oxothieno[2,3-b]pyridine-3-carboxamido)-2-phenylacetyl, 2-(4-ethyl-2,3-dioxo-1-piperazinocarboxamido)-2-thienylacetyl, 2-(4-n-pentyl-2,3-dioxo-1-piperazinocarboxamido)-2thienylacetyl, 2-(4-n-octyl-2,3-dioxo-1-piperazinocarboxamido)2-thienylacetyl, 2-(4-cyllohexyl-2,3-dioxo-1-piperazinocarboxamido)2-thienylacetyl, 2-[4-(2-phenylethyl)-2,3-dioxo-1-piperazinocarboxamido]-2-thienylacetyl, 2-(3-methylsulfonyl-2-oxoimid- azolidine-1-carboxamido)-2-phenylacetyl, 2-(3-furfurylideneamino2-oxoimidazolidine-1-carboxamido)-2-(p-hydroxyphenyl)acetyl, 2-(4-etyyl-2,3-dioxo-1-piperazinocarboxamido)-2-(p-benzyloxyphenyl)acetyl, 2-(4-ethyl-2,3-dioxo-1-piperazinocarboxamido)2-(p-methoxyphenyl)acetyl, 2-(8-hydroxy-1,5-naphthylidine-7-carboxamido]-2-phenylacetyl, 2-[2-aminothiazol-4-yl)-2-formamidoacetyl and 2-(2-aminothiazol-4-yl)-2-acetamidoacetyl.

As the specific example of the acyl group represented by the formula $R^9$- $R^{10}$—CO—, use is made for example of N-[2-(2- aminothiazol-4-yl)-2-methoxyiminoacetyl]-D-alanyl, N-[2-(2-aminothiazo4-yl-2-methoxyiminoacetyl]-D-phenylglycyl, 2-(2-aminothiazol-4-yl -2-[2-(2-aminothiazol-4-yl)-2-methoxyiminoacetamido]acetyl, 2-(2-clloroacetamidothiazol-4-yl)-2-methoxyiminoacetyl, 2-(2-aminothiazol-4-yl)-2-methoxyiminoacetyl, 2-(2-amino-thiazol-4-yl)-2-ethoxyimi0oacetyl, 2-(2-aminothiazol-4-yl)-2propoxyiminoacetyl, 2-(2-aminothiazol-4-yl)-2-butoxyiminoacetyl, 2-(2-amino-4-thiazol-4-yl)alloxyiminoacetyl, 2-(2-aminothiazol-4-yl)-2-allyloxyiminoacetyl, 2-(2-aminothiazol-4-yl)-2-[(1-methyl-1-carboxyethyl)oxyimino]acetyl, 2-(2-aminothiazol4-yl)-2-[(1-methyl-1-methoxycarbonylethyl)oxyimino]4 acetyl, 2-(2-aminothiazol-4-yl)-2-carboxymethoxyiminoacetyl, 2-(2-aminothiazol-4-yl)-2-carboxyvinyloxyiminoacetyl, 2-(2-aminothiazol-4-yl)-2-carboxyethoxyiminoacetyl, 2-(2-aminothiazol-4-yl)-2-methoxycarbonylethoxyiminoacetyl, 2-(2-aminothiazol-4-yl-(3,4-diacetoxybenzoyl)methoxyiminoacetyl, 2-(2-amino-5-chlorothiazol-4-yl)-2-methoxyiminoacetyl, 2-(2-amino5-bromothiaool-4-yl)-2-methoxyiminoacetyl, 2-(2-aminothiazol-4-yl)2-oxyiminoacetyl, 2-thienyl-2-methoxyiminoacetyl, 2-furyl-2methoxyiminoacetyl, 2-(1,2,4-thiadiazol-3-yl)-2-methoxyiminoacetyl, 2-(1,2,4-thiadiazol-5-yl)-2-methoxyiminoacetyl, 2-(1,3,4-thiadiazol-2-yl)-2-methoxyiminoacetyl, 2-(p-hydroxyphenyl)-2-methoxyiminoacetyl, 2-phenyl-2-methoxyiminoacetyl, 2-phenyl-2oxyiminoacetyl, 2-[4-(γ-D-glutamyloxy)phenyl]-2-oxyiminoacetyl and 2-[p-(3-amino-3-carboxypropoxy)-phenyl]-2-oxyiminoacetyl.

As the specific example of the acyl group represented by the formula

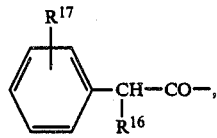

use is made for example of α-sulfophenylacetyl, α-hydroxyphenylacetyl, α-sulfureidophenylacetyl, α-sulfoureidophenylacetyl, α-sulfamoylphenylacetyl, α-phenoxycarbonylphenylacetyl, α-(p-tolyloxycarbonyl)-phenylacetyl and α-formyloxyphenylacetyl.

As the specific example of the acyl group represented by the formula $R^{18}$—$R^{19}$—CH$_2$—CO—, use is made for example of cyanoacetyl, phenylacetyl, phenoxyacetyl, trifluoromethylthioacetyl, cyanomethylthioacttyl, 1H-tetrazol-1-ylacetyl, thienylacetyl, 2-(2-amincthiazol-4-yl)acetyl, 4-pyridylthioacetyl, 2-thienylthioacetyl, 3,5-dichloro-1,4-dihydro-4-oxopyridine-1-acetyl, β-carboxyvinylthioacetyl and 2-(o-aminomethylphenyl)acetyl.

Of the above-mentioned specific examples of the acyl groups, the amino and/or carboxy and/or hydroxy groups, which have the protective groups, are also included. As the said amino-protecting group, use is made of the same as the amino-protecting groups to be described below. As the protective groups for carboxy and hydroxy groups, use is made of those as mentioned above.

As the protective group for amino group, i.e. a substituent at the 3-position of the derivatives[I], which may be protected, groups being usable for this purpose in the fields of β-lactam and peptide synthesis are suitably adopted. For example, use is made of aromatic acyl groups such as phthaloyl, p-nitrobenzoyl, p-tert-butylbenzoyl, p-tert-butylbenzenesulfonyl, benzenesulfonyl, toluenesulfonyl, phenylacetyl and phenoxyacetyl; aliphatic acyl groups such as formyl, acetyl, propionyl, monochloroacetyl, dichloroacetyl, trichloroacetyl, methanesulfonyl, ethanesulfonyl, trifluoroacetyl, maleoyl add succinyl; oxycarbonyl groups such as methoxycarbonyl, ethoxycarbonyl, tert-butoxycarbonyl, isopropoxycarbonyl, 2-cyanoethoxycarbonyl, β,β,β-trichloroethoxycarbonyl, β-trimethylsilylethoxycarbonyl, β-methylsulfonylethoxycarbonyl, benzyloxycarbonyl, p-nitrobenzyloxycarbonyl, p-methoxybenzyloxycarbonyl, diphenylmethoxycarbonyl, methoxymethyloxycarbonyl, acetylmethyloxycarbonyl, isobornyloxycarbonyl and phenoxycarbonyl; furthermore, protective groups other than acyl group such as trityl, o-nitrophenylthio, benzylidene, p-nitrobenzylidene or trialkylsilyl, benzyl and p-nitrobenzyl; and proton. The choice of said protective groups is not particularly restricted in this invention.

The derivatives[I] may have two substituents at the 3-position, and may have as the 3-substituent the above-mentioned aminogroup which may be acylated or protected and the abovementioned lower alkoxy group. Furthermore, the 4-position of the derivatives[I] may be either unsubstituted or substituted.

Preferred examples of the derivatives [I], their salts or esters include compounds of the formula:

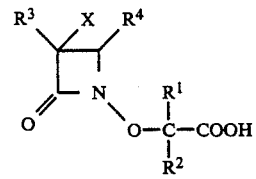

[I]′ wherein $R^1$ and $R^2$ are as defined above; $R^3$ is an amino group which may be acylated or protected; $R^4$ is hydrogen atom, carboxy, alkoxycarbonyl, carbamoyl which may have a substituent, aryl which may have a substituent or alkyl which may have a substituent; X is a hydrogen atom or methoxy group, their salts or esters. In the formula [I]′, the amino group repreeented by $R^3$ which may be acylated or protected designates those as described above. As the alkoxycarbonyl group represented by $R^4$, use is made for example of $C_{1-6}$ alkoxycarbonyl groups, whereby as the $C_{1-6}$ alkoxy, use is made of those mentioned for the above $R^1$ and $R^2$. As the substituent (one to two) on the carbamoyl group represented by R⁴ which may have a substituent, use is made for example of the above-mentioeed lower alkyl groups having one to six carbon atoms and lower alkoxy groups having one to six carbon atoms as well as benzyloxy, phenyl, amino, N-methylamino, and N,N-dimethylamino groups. As the aryl represented by R⁴ which may have a substituent, use is made for example of those as mentioned for the above R¹ and R². As the alkyl group represented by R⁴ which may have a substituent, use is made for example of groups of the formula:

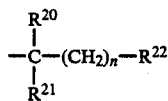
[F]

wherein n is an integer of zero to three; $R^{20}$, $R^{21}$ and $R^{22}$ are the same or different and each represents a hydrogen atom, lower alkyl having one to six carbon atoms, cycloalkyl*, aryl*, heterocycle*, (lower alkyl having one to six carbon atoms)-oxycarbonyl, acyl, halogen, cyano, hydroxy, (lower alkyl having one to six carbon atoms)oxy, aryl*oxy, aryl*alkyloxy, acyloxy, carbamoyloxy, hydroxysulfonyloxy, (lower alkyl having one to six carbon atoms)-sulfonyloxy, aryl*sulfonyloxy, nitro, amino, azide, carboxy, (lower alkyl having one to six carbon atoms)-oxycarbonylmethoxy, carbamoylmethoxy, carbamoyl, mercapto, (lower alkyl having one to six carbon atoms)thio, aryl*thio, heterocycle*thio or quaternary ammonium*]. Of the groups represented by $R^{20}$ through $R^{22}$, as the $C_{1-6}$ lower alkyl, aryl*, heterocycle* and halogen, use is made of those as described above. As the cycloalkyl, frequent use is made for example of cycloalkyl groups having three to eight carbon atoms such as cyclopropyl, cyclobutyl, cyclopentyl, cyclohexyl, cycloheptyl, and adamantyl. As the substituent in the cycloalkyl*, use is made of those similar to substituents on the aryl represented by the above R¹ and R².

As the acyl group, use is made of formyl as well as acyl group employed for R³, i.e. the substituent at the 3-position of the above derivatives[I]. As the quaternary ammonium group, use is made for example of quaternary ammonium groups as represented e.g. by the general formula:

wherein W is hydrogen atom, methyl, carbamoylmethyl, carboxymethyl, carbamoyl, carboxy, sulfo or methoxy group derived from pyridine and pyridine derivatives such as carbamoyl-group substituted pyridines exemplified by nicotinamide or isonicotinamide, carboxy group substituted pyridines exemplified by nicotinic acid or isonicotinic acid and sulfo-group substituted pyridines exemplified by pyridinesulfonic acid, or quinolinium. As the substituents in the quaternary ammonium* group, use is made of those similar to substituents on the aryl represented by the above R¹ and R². These quaternary ammonium groups can form inner salts with intramolecular carboxy group or sulfo group. When the amino group is present in the substituents represented by $R^{20}$, $R^{21}$ and $R^{22}$, such amino group may be substituted or protected, while in the case of the carboxy or hydroxy group being present, these may also be protected. As the substituent on the amino group, use is made for example of acyl, lowe alkyl having one to six carbon atoms, aryl*, aryl*methyl, hydroxysulfonyl, (lower alkyl having one to six carboxy atoms)-sulfonyl and carbamoyl (whereby as the acyl, lower alkyl having one to six carbon atoms and aryl*, use is made of the those as mentioned above). Furthermore, they may form cyclic amino groups, such as pyrrolidino, piperidino, morpholino, and piperazino, with these substituents. As the protective groups for the amino, carboxy and hydooxy groups, use is made of those similar to the protective groups used for the above R³.

Particularly preferred examples of the groups represented by the formula [F] include methyl, ethyl, carbamoyloxymethyl, acetoxymethyl, acetamidomethyl, carbamoylaminomethyl, methoxymethyl, ethoxymethyl,methylthiomethyl, ehhylthiomethyl, chloromethyl, fluoromethyl, cyanomethyl, azidomethyl, carbamoylmethyl, methoxycarbonylmethyl, ethoxycarbonylmethyl, carbamoyloxyethyl, methoxyethyl, ethoxyethyl, pyridiniomethyl, pyridinioethyl, and (4-carbamoylpyridinio)methyl.

The derivatives[I] of this invention can exist in various steric isomers (e.g., cis, trans and optically active isomers) with reference to the 3- and 4-positions of its β-lactam ring, and it is to be understood that the present invention encompasses these individual isomers as well as mixtures thereof.

Of the optically active isomers described above, the optically active isomers of the formula:

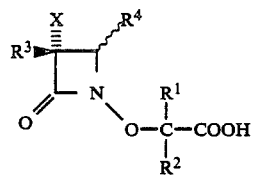
[III]

wherein R¹, R², R³, R⁴ and X are as defined above; the dotted line denotes that R⁴ at the 4-position is in the cis- or transconfiguration to R³ at the 3-position, namely the compounds having R³ in the β-configuration (in the case of X being a hydrogen atom, the compounds having 3S-configuration and in the case of X being a methoxy group, the compounds having the 3R-configuration), exhibit enhanced antimicrobial activity as compared with the corresponding compounds having R³ in the α-configuration. Among the derivatives [I], consequently, the compounds of the formula [III] are in conformity with the purpose of this invention and preferable.

When R¹ and R² are different or when R¹, R², R³ and R⁴ contain the asymmetric carbon atom, the compounds can occur in optically active isomers, and in the case of R³ having the unsaturated bond, furthermore, they can also occur in geometrical isomers (e.g., syn, anti, cis, trans, Z- and E-isomers). These individual isomers and mixtures thereof are also included in the present invention.

Also, this invention relates to;
(1) the derivative [I], their salts or esters,
(2) the compounds as described under (1) having a carbamoyl or carbamoyloxyalkyl group at the 4-position, (3) the compounds as described under (2) having a carbamoyl group at the 4-position, (4) the compounds as described under (2) having a carbamoyloxyalkyl group at the 4-position, (5) the compounds as described under (4) wherein the carbamoyloxyalkyl is carbamoyloxymethyl, (6) the derivatives [I] as described under (1) through (5) wherein the substituent at the 3-position is 2-(2-aminothiazol4-yl)-(Z)-2-carboxymethoxyiminoacetamide group, their salts or esters, (7) the derivatives [I] as described under (1) through (5) wherein the substituent at the 3-position is a 2-(2-aminothiazol-4-yl)-(Z)-2-(1-carbonyl-1-methylethoxyimino)acetamido group, their salts or esters, (8) the derivatives [I] as described under (1) through (7) wherein the substituent at the 1-position is a group represented by the formula

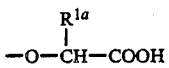

in which $R^{1a}$ is an aryl group which may have a substituent, their salts or esters (9) the derivatives [I] as described under (1), (2), (4) or (5) which are represented by the formula:

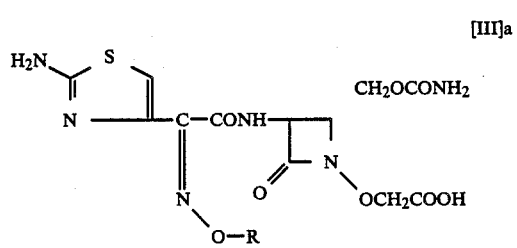

[III]a wherein R is an alkyl or carboxyalkyl group, their salts or esters, and

(10) the compounds as described under (1) through (9) which have a 4-substituent of the azetidine ring in the trans configuration to a 3-substituent of the same.

In the formula

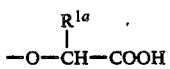

under the above (8), $R^{1a}$ is an aryl group which may have a substituents. As the aryl group which may have a substituent as represented by $R^{1a}$, use is made for example of those mentioned for the above $R^1$ and $R^2$. The preferred examples of $R^{1a}$ include for example a phenyl group which may have a substituent. As the substituent on the phenyl group which may have a substituent, use is made for example of lower alkyl having one to four carbon atoms such as methyl, ethyl, n-propyl, isopropyl, n-butyl and tert-butyl,lower alkoxy having one to four carbon atoms such as methoxy, ethoxy, n-propoxy, isopropoxy, n-butoxy and tert-butoxy,- halogen such as fluorine, chlorine and bromine, hydroxy and amino. The number of the substituents on the phenyl group is one to three, and when then number is not less than two, the substituents may be the same ordifferent. As the preferred example of $R^{1a}$, use is made for example of phenyl, p-hydroxyphenyl, p-methoxyphenyl, 3,4-dihydroxyphenyl and p-chlorophenyl. R in the formula [III]a described under (9) represents alkyl or carboxyalkyl. As the alkyl of the alkyl and carboxyalkyl represented by R, use is made for example of those described for the above $R^1$ and $R^2$. Preferable examples of R include for example methyl, —CH$_2$COOH and —C(CH$_3$)$_2$COOH.

The derivatives [I], their salts or esters having a carbamoyloxyalkyl group at their 4-positions, namely the compounds under the above (4) and (5) and the like, demonstrate excellent antimicrobial activity against pathogenic bacteria such as Enterobacter cloacae IFO 12937. Of the compounds as described under (4) and (5), particularly, the compounds having a carbaoyloxyalkyl group of the azetidine ring in the trans configuration to a 3-substituent of the same exhibit by far improved antimicrobial activity as compared with the corresponding compounss having the cis configuration, and the difference in antimicrobial activity between two types of compounds is unexpectedly great.

The derivatives [I] of this invention may be employed while having the carboxy group in the 1-substituent and the carboxy groups in the 3- and 4-substituents in the free form, but may also be used after having them converted into salts with nontoxic cations such as sodium and potassium, basic amino acids such as arginine, ornithine, lysine and histidine, polyhydroxyalkylamines such as N-methylglucamine, diethanolamine, triethanolamine and trishydroxymethylaminomethane, and the like. When the 3- and 4-substituents of the derivatives [I] contain a basic group, the derivatives [I] may be used after having such basic groups converted into salts with organic acids such as acetic acid, tartaric acid and methanesulfonic acid, inorganic acids such as hydrochloric acid, hydrobromic acid, sulfuric acid and phosphoric acid, acidic amino acids such as aspartic acid and glutamic acid, and the like. The derivatives [I] can also be used after having the above carboxy groups:contained therein converted into biologically active ester derivatives conducive to increased blood concentration and prolonged in vivo activity. As the ester groups effective in such a case, use is made for example of alkoxymethyl such as methoxymethyl, ethoxymethll, isopropoxymethyl, 1-methoxyethyl and 1-ethoxyethyl, 1-alkoxy1-substituted methyl groups such as 1-alkoxyethyl, alkylthiomethyl groups such ss methylthiomethyl, ethylthiomethyl and isopropylthiomethyl, acyloxymethyl or 1-acyloxy-1-substituted methyl groups such as pivaloyloxymethyl and 1-acetoxybutyl, and 1-alkoxycarbonyloxy-1-substituted-methyl groups such as ethoxycarbonyloxymethyl and 1-ethoxycarbonyloxyethyl. When the derivatives I , i.e. the objective compounds of this invention, are employed as an intermediate, such oarboxy groups may be protected with the above-mentioned protective groups.

Specific examples of the derivatives [I] as described above include the following compounds in addition to the compounds of the examples to be mentioned below.

(a) (3S)-3-2-(2-Aminothiazol-4-yl)-(Z)-2-carboxymethoxyiminoacetamido]-1-(1-carboxy-1-methylethoxy)-2-azetidinone, (b) (3S)-3-[2-(2-Aminothiazol-4-yl)-(Z)-2-methoxyiminoacetamido]-1-(α-carboxy-p-hydroxybenzyloxy)-2-azetidinone, (c) (3S,4S)-1-Carboxymethoxy-3-[(D)-2-(4-hydroxy-1,5-naphthylidine3-carbonylamino)-2-phenylacetamido]-4-methyl-2-azetidinone, (d) (3S,4S)-1-Carboxymethoxy-3-[(D)-2-(4-hydroxy-6-methylpyridine-3-carbonylamino)-2-(p-hydroxyphenyl)acetamido-4-methyl-2-azetidinone, (e) (3S,4R)-3-[2-(2-Aminothiazol-4-yl)-(Z)-2-(1-carboxy-1-methylethoxyimino)acetamido]-1-carboxymethoxy-4-methyl-2-azetidinone, (f) (3S)-1-Carboxymethoxy-3-[(D)-2-(4-ethyl-2,3-dioxo-1-piperazino)carbonylamino-2-phenylacetamido]-2-azetidinone, (g) 3,4-trans-3-[2-(2-Aminothiazol-4-yl)-(Z)-2-carboxymethoxyiminoacetamido]-4-carbamoyloxymethyl-1-carboxymethoxy-2-azetidinone, (h) 3,4-trans-3-[2-(2-Aminothiazol-4-yl)-(Z)-2-(1-carboxy-1-methylethoxyimino)acetamido]-4-carbamoyl-1-carboxymethoxy-2-azetidinone, (i) 3,4-trans-3-[2-(2-Aminothiazol - 4-yl)-(Z)-2-(1-carboxy-1methylethoxyimino)acetamido]-1-carboxymethoxy-4-methoxymethyl-2-azetidinone, (j) (3S,4S)-3-[2-(5-Amino-1,2,4-thiadiazol - 3-yl)-(Z)-2-ethoxyiminoacetamido]-1-carboxymethoxy-4-methyl-2-azetidinone, (k) (3S,4S)-3-[2-(5-Amino-1,2,4-thiadiazol 3-yl)-(Z)-2-carboxymethoxyiminoacetamido]-1-carboxymethoxy-4-methyl-2-azetidinone, and (l) (3S)-3-[2-(5-Amino-1,2,4-thiadiazol 3-yl)-(Z)-2-(1-carboxy-1-methylethoxyimino)acetamido]-1-carboxymethoxy-2-azetidinone.

The derivatives [I] or their salts or esters in which the 3-substituent $R^3$ is an acylated amino group are valuable antimicrobial agents active against a variety of gram-positive and gram-negative bacteria, and are utilized as medicaments to human beings and domestic animals. The above compounds wherein $R^3$ is an amino group which may be protected are useful as an intermediate for the synthesis of the above-mentioned antimicrobial agents.

The antimicrobial agents of this invention can be used solely or in combination with other active substances in any of various pharmaceutical preparations such as capsules, tablets, powders or solutions, suspensions or elixirs. These preparations can be administered orally, intravenously or intramuscularly.

Tablets usable for oral administration can contain a conventional excipient, for example, a binder such as syrup, gum arabic, gelatin, sorbitol, gum tragacanth or polyvinylpyrrolidone; filler such as lactose,.sugars, corn starch, calcium phosphate, sorbitol or glycine; lubricant such as magnesium stearate, talc, polyethylene glycol and silica; disintegrating agent such as potato starch; or surface active agent such as sodium lauryl sulfate. The tablets can be coated in a manner well known in the art. The oral liquid preparations may be in such dosage forms as aqueous or oil suspensions, solutions, emulsions, syrups, elixirs, etc. or in the form of lyophilizates for extemporaneous dissolution in water or a suitable solvent. These liquid preparations can contain a suspending agent such as sorbitol syrup, methylcellulose, glucose/sugar syrup, gelatin, hydroxyethylcellulose, carboxymethylcellulose and aluminum stearate gel, a preservative such as methyl or propyl p-hydroxybenzoate or sorbic acid, or any other ingredient such as a hydrogenated edible oil, almond oil, coconut oil fractions, oily esters, propylene glycol, ethyl alcohol. Suppositories may contain a conventional suppository base, such as theobroma oil or other glycerides.

Injectable compositions can be made available in ampules or other unit-dose containers with the addition of a preservative. These compositions may be in such dosage forms as suspensions, solutions or emulsions in an oily or aqueous vehicle, and may contain a suitable adjuvant or adjuvants such as a suspending agent, stabilizer and/or dispersing agent. Alternatively, the active substance may be in the form of powder reconstitutable with a suitable solvent such as sterilized pyrogen-free water prior to use. The active ingredient can also be formulated into suitable dosage forms adsorbable through the mucous membranes of the nose and throat or the bronchial tissues, for example, powders, liquid sprays or inhalants, lozenges, throat paints, etc. For ophthalmological or otological application, it can be administered as liquid or semisolid capsules or as drops for instillation. In addition, it may be formulated with hydrophobic or hydrophilic pharmaceutical bases into such dosage forms as ointments, creams, lotions, paints, powders, etc. to provide pharmaceutical preparations for external application.

In addition to the carriers, these preparations may contain other components such as stabilizers, binders, antioxidants, preservatives, lubricants, suspending agents, rheology modifiers or flavoring agents. Moreover, other active compound(s) can be incorporated in the composition to provide for a broader spectrum of antimicrobial activities. For administration to domestic animals, intramammary preparations can be formulated by using a medium intended to long-lasting effect or rapid release.

The antimicrobial agents of this invention can be applied to mammals as thrapeutic agents for microbial infections in the treatment of, for example, respiratory tract infections, urinary tract infections, suppurative infections, bile duct infections, intestinal infections, gynecological infections, surgical infections, etc. Their daily dosage varies with the condition of the patient to be treated, the weight of the host, the route and frequency of administration, the particular parenteral procedure suitable for general infections and the oral procedure employed for intestinal infections. Generally, the oral daily dosage comprises the active ingredient in an amount of about 15 to 600 mg per kg of body weight of the patient in one or more doses. The daily dosage suitable for administration to an adult human is about 10 to about 300 mg per kg of body weight as the active ingredient, which can suitably be administered daily in two to four doses of about 2.5 to about 150 mg per kg each by a route other than the oral.

A pharmaceutical composition containing the derivatives[I] can be administered, for example, in various liuuid or solid, orally ingestable unit dosage forms. The liquid or solid unit dosage composition may contain 0.5 to 99% of the active substance, with the preferred concentration range being about 10 to 60%. The composition generally contains about 15 to 1500 mg of the active ingredient, but it is generally preferable to use a unit dose in the range of about 250 to 1000 mg as the active ingredient.

The derivatives [I] that are the objective compounds of this invention can be prepared by subjecting a 2-azetidinone derivative (hereinafter referred to briefly as "starting compound [IV]") having a group of the formula

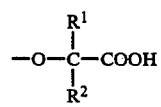

wherein the symbols are as defined above at the 1-position and an amino group at the 3-position, its salt or ester to an acylation reaction or protective-group introduction reaction.

As the salt or ester of the starting compound [IV], use is made for example of those mentioned for the salts and esters of the derivatives [I]. Acylation can be effected by reacting such starting compound [IV], its salt or ester with a carboxylic acid of the formula $R^0COOH$ wherein $R^0CO$ is an acyl group as mentioned above for the 3-substituent of the derivative [I], its salt (e.g., salts with alkal metals such as sodium and potassium) or reactive derivative. When the starting compound [IV], its salt or ester contains a free amino, carboxy or hydroxy group, such compound may be subjected to this reaction after the above-mentioned protective groups are introduced by the conventional procedure. After the completion of the reaction, if desired, these protective groups may be removed on the basis of the known methods. As the reactive derivative of the carboxylic acid represented by the formula $R^0COOH$, use is made for example of acid halides, acid anhydrides, active amides, active esters and active thioesters, and such reactive derivatives are exemplified in the following:

(1) Acid halides:
As the acid halide, use is made for example of acid chlorides and acid bromides.

(2) Acid anhydrides:
As the acid anhydride, use is made for example of mixed acid anhydrides with monoalkylcarbonic acids, aliphatic carboxylic acids (e.g., acetic acid, pivalic acid, valeric acid, isovaleric acid, trichloroacetic acid, etc.) and aromatic carboxylic acids (e.g., benzoic acid, etc.), and symmetric acid anhydrides.

(3) Active amides:
As the active amide, use is made for example of amides with pyrazole, imidazole, 4-substituted imidazoles, dimethylpyrazole, benzotriazole, etc.

(4) Active esters:
As the cctive ester, use is made for example of esters such as methyl, ethyl, methoxymethyl, propargyl, p-nitrophenyl, 2,4-dinitrophenyl, trichlorophenyl, pentachlorophenyl and mesylphenyl esters as well as esters of the above-mentioned carboxylic acids with 1-hydroxy-1H-2-pyridone, N-hydroxysuccinimide, N-hydroxyphthalimide, etc.

(5) Active thioesters:
As the active thioester, use is made for example of thioesters with heterocyclic thiols such as 2-pyridylthiol and 2-benzothiazolylthiol. The various reactive derivatives described above are suitably selected depending upon the type of carboxylic acid to be used. In this acylating procedure, one mole of the starting compound [IV], its salt or ester is in the first place reacted with not less than one mole, preferably one to four moles, of a carboxylic acid, its salt or reactive derivative to carry out the acylation. This reaction is usually carried out in a solvent. As the solvent, use is made of water, acetone, dioxane, acetonitrile, methylene chloride, chloroform, dichloroethane, tetrahydrofuran , ethyl acetate, N,N-dimethylformamide, N,N-dimethylacetamide, pyridine or other conventional organic solvents which do not affect the reaction. Of these, hydrophilic solvents can be used as a mixture with water. When the carboxylic acid is used in the free form, it is preferable to conduct the reaction in the presence of a condensing agent, whereby as such condensing agent, use is made for example of N,N'-dicyclohexylcarbodiimide, N-cyclohexyl-N'-morpholinoethylcarbodiimide, N-cyclohexyl-N'-(4-diethylaminocyclohexyl)carbodiimide and N-ethyl-N'-(3-dimethylaminopropyl)carbodiimide. Also, this reaction can be carried out in the presence of a base, such as alkali metal carbonates, trialkylamines exemplified by trimethylamine, triethylamine, tributylamine, N-methylmorpholine and N-methylpiperidine, N,N-dialkylanilines, N,N-dialkylbenzylamines, pyridine, picoline, lutidine, 1,5-diazabicyclo[4,3,0]non5-ene, 1,4-diazabicyclo[2,2,2]octane and 1,8-diazabicyclo[5,4,4]undec-7-ene. Among the bases or the above-mentioned condensing agents, liquid compounds can also function as a solvent. The reaction temperature is not particularly restricted, and the reaction is conveniently carried out under cooling or at room temperature, and goes to completion in a few minutes to several ten hours. The resulting product in this reaction can be isolated and purified by the per se known methods such as concentration, change of pH, change of solvent, solvent extraction, crystallization, recrystallization, fractional distillation and chromatography, but the reaction mixture, as such without being isolated, can be used as a starting material in the subsequent step.

The reaction of introducing a protective group into the starting compound [IV], its salt or ester can be carried out according to the known methods [e.g., the method as described in "Peptides, Proceedings of the Fifth European Symposium, Oxford, Sept., 1962, and the like], as far as the objective derivative [I] is obtained.

When the derivatives[I] thus obtained contain protective groups other than the protective group for the 3-amino group, such protective groups may be removed, if deiired, and as the method of removing such protective groups, the conventional methods such as the methods comprising the use of an acid, base, hydrazine and reduction and the method comprising the action of an iminohalogenating agent and then iminoetherifying agent, if desired, followed by hydrolysis, can be suitably selected to accomplish the removal, depending upon the type of the particular protective group to be removed. In the case of the method involving the use of an acid, use is made, as the acid, of inorganic acids such as hydrochloric acid, sulfuric acid and phosphoric acid, and organic acids such as formic acid, acetic acid, trifluoroacetic acid, propionic acid, benzenesulfonic acid and p-toluenesulfonic acid as well as acidic ion exchange resins and the like, which vary with the type of the protective groups to be removed and other conditions. In the case of the method comprising the use of a base, use is made, as the base, of inorganic bases subh as hydroxides and carbonates of alkali metals exemplified by sodium and potassium and alkaline earth metals exemplified by calcium and magnesium, and organic bases such as metal alkoxides, organic amines and quaternary ammonium salts as well as basic ion exchange resins and the like, which vary with the type of the protective groups to be removed and other conditions. When a solvent is used in the case of the above method comprising the use of an acid or base, hydrophilic organic solvents, water or mixed solvents are often employed. When the protective group is removed by reduction, the method involving the use of the combination of a metal such as tin and zinc cr a metal compound such as chromium dichloride and chromium acetate and an acid such as organic and inorganic acids exemplified by acetic acid, propionic acid, hydrochloric acid, etc., the method of reduction in the presence of a metal catalyst for catalytic reduction, and the like may be employed depending upon the type of the protective group to be removed and other conditions. The catalysts that can be used in the method by means of catalytic reduction include, for example, platinum catalysts such as platinum wire, platinum sponge, platinum black, platinum oxide and colloidal platinum, palladium catalysts such as palladium sponge, palladium black, palladium oxide, palladium on barium sulfate, palladium on barium carbonate, palladium on charcoal, palladium on silica gel and colloidal palladium, reduced nickel, nickel oxide, Raney nickel and Urushibara nickel, and the like. In the case of reduction with metal and acid, compounds of metals such ss iron and chromium and inorganic acids such as hydrochloric acid and organic acids such as formic acid, acetic acid and propionic acid are used. The removal of the protective group by reduction is usually conducted in a solvent, and in the method by means of catalytic reduction, frequent use is made of alcohols such as methanol, ethanol, propyl alcohol and isopropyl alcohol, ethyl acetate, etc. In the method by means of reduction with metal and acid, frequent use is made of water, acetone and the like, and when the acid is liquid, it can also be used itself as a solvent. As to the reaction temperature in the methods comprising the use of an acid, base and reduction, the reaction is usually carried out under cooling to under warming In the case of the method of removing the protective group which comprises the action of an iminohalogenating agent and then an iminoetherifying agent, if desired, followed by hydrolysis, the iminohalogenating agents being usable include for example phosphorus trichloride, phosphorus pentachloride, phosphorus tribromide, phosphorus oxychloride, thionyl chloride, phosgene, etc. The reaction temperature is not particularly restricted, but the reaction is often carried out normally at room temperature to under cooling. As the iminoetherifying agent which is to be acted on the resulting reaction product, use is made of alcohols or metal alkoxides, whereby the alcohols include alkanols such as methanol, ethanol, propanol, isopropanol, n-butanol and tert-butanol as well as those compounds in which the alkyl moieties of these alcohols are substituted with alkoxy groups such as methoxy, ethoxy, propoxy, isopropoxy and butoxy, and the metal alkoxides include alkali metal alkoxides such as sodium alkoxides and potassium alkoxides and alkaline earth metal alkoxides such as calcium alkoxides and barium alkoxides derived from the above-mentioned alcohols.

Also, the derivatives [I] can be prepared by reacting a 2-azetidinone derivative (hereinafter referred to briefly as "starting compound [V]") having a hydroxy group at the 1-position and an amino group, at the 3-position, which may be protected or its salt with the compound [II], its salt or ester. As the salt and ester of the compound [II] and the salt of the starting compound [V], use is made of the salts and esters mentioned for the derivative [I]. When the free amino, carboxy and hydroxy groups are present in the compound [II], starting compound [V], their salts or esters, such compounds can also be used as a starting compound for this reaction after the protective groups are introduced by the conventional method. After the completion of the reaction, such protective groups may be removed by the deprotecting methods as described above, if desired. One mole of the starting compound [V] or its salt is reacted with one to ten moles, preferably one to five moles, of the compound [II] its salt or ester. This reaction is normally carried out in the presence of a base. As the base, use is made for example of inorganic salts such as potassium carbonate, sodium carbonate, potassium hydrogen carbonate and sodium hydrogen carbonate and organic bases such as triethylamine, diisopropylethylamine and pyridine. As the reaction solvent, use is made of organic solvents, solely or as a mixture, such as water, ethers exemplified by dioxane, tetrahydrofuran, etc., ketones exemplified by acetone, methyl ethyl ketone, etc., esters exemplified by ethyl formate, ethyl acetate, etc., halogenated hydrocarbons exemplified by chloroform, dichloromethane, dichloroethane, etc., amides exemplified by N,N-dimethylformamide, N,N-dimethylacetamide, etc., dimethylsulfoxide and acetonitrile, and among others, acetonitrile and N,N-dimethylformamide are preferred. The reaction is carried out at a temperature ranging from $-30°$ to $60°$ C., and the temperature range of from $0°$ to $30°$ C. is normally preferable. The reaction temperature varies greatly with the type of the compound [II] and reaction temperature, and normally ranges from a few minutes to several ten hours. The resulting derivative [I] can be isolated and purified by the above-described known methods but when it is utilized as an intermediate for synthesis, the reaction mixture, as such without being isolated, can also be used as a starting material in the subsequent step.

In more particular, the derivatives [I] can be prepared from the known starting compounds for example by the processes as illustrated by the following formulas.

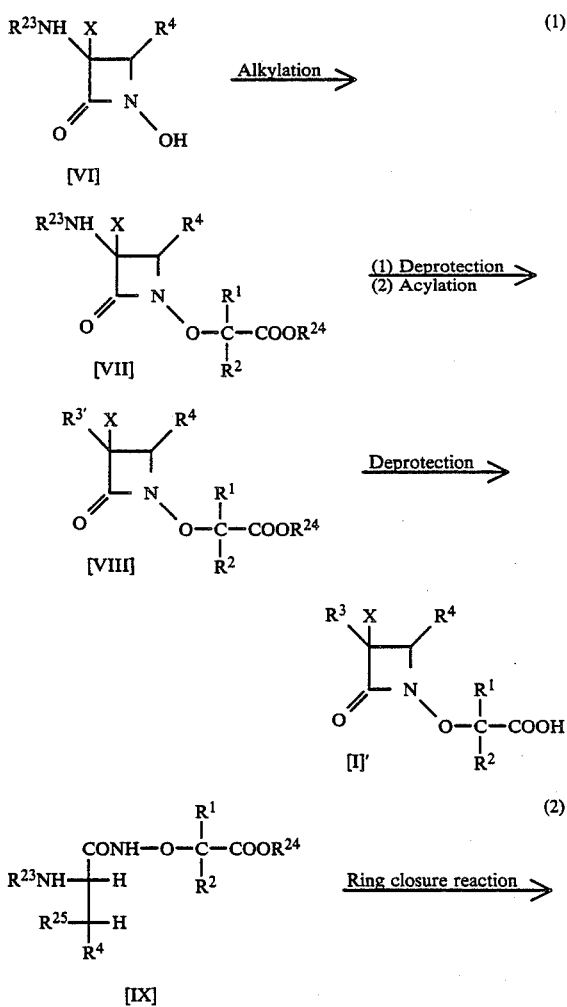

-continued

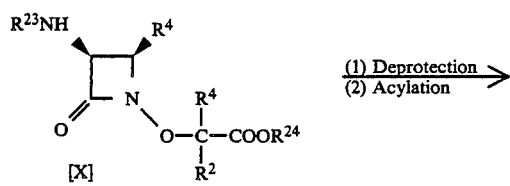

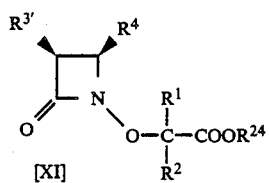

(3)

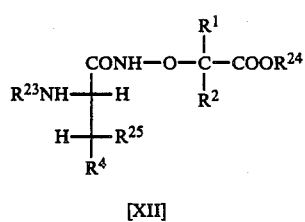

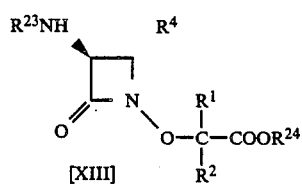

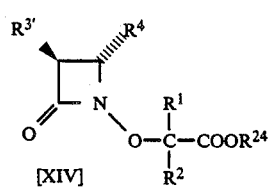

(4)

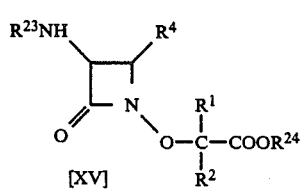

-continued

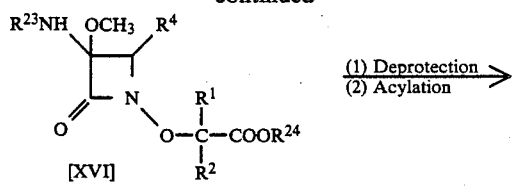

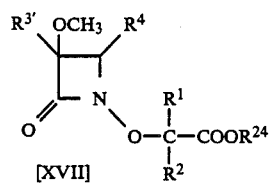

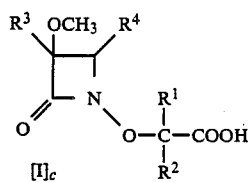

wherein $R^1$, $R^2$, $R^3$, $R^4$ and X are as defined above; $R^{23}$ is an amino-protecting group; $R^{24}$ is a carboxy-protecting group; $R^{25}$ is a hydroxy, halogen atom, alkylsulfonyloxy or aryl*sulfonyloxy group; $R^{3\prime}$ is an acylated amino group.

In the above processes (1) through (4), as the amino-protecting group represented by $R^{23}$ and carboxy-protecting group represented by $R^{24}$, use is made of those similar to the protective groups as mentioned above. Preferred exmmples of the alkylsulfonyloxy group represented by $R^{25}$ include methanesulfonyloxy, ethanesulfonyloxy and the like. Preferable examples of the aryl*sulfonyloxy group represented by $R^{25}$ include benzenesulfonyloxy, p-toluenesulfonyloxy, p-chlorobenzenesulfonyloxy and the like. As the acylated amino group represented by $R^{3\prime}$, use is made of those similar to the acylated amino groups as mentioned above, and when such groups contain free amino, carboxy and hydroxy groups, they may contain various protective groups.

In the above reaction formula (1), the alkylation reaction can be carried out, for example, in accordance with the reaction of the starting compound [V] or its salt with the compound [II], its salt or ester or by a procedure similar thereto. The acylation and deprotection in the reaction formulas (1) through (4) can be conducted in accordance with the acylation reaction and the method of deprotection as mentioned in the process for producing the derivative [I] which comprises subjecting the above starting compound [IV], its salt or ester to an acylation or protective group introduction reaction or by their analogous procedures.

The ring closure reaction in the reaction formulas (2) and (3) is a reaction which involves the conversion of a compound represented by the general formula [IX] or [XII] into a 2-azetidinone derivative, and in the case of the starting compound [IX] or [XII] where $R^{25}$ is a halogen atom, alkylsulfonyloxy or aryl*sulfonyloxy group, this ring closure reaction is carried out by reacting the compound [IX] or [XII] with a base. As such base, use is made for example of inorganic bases such as potassium carbonate, sodium carbonate, potassium hydrogen carbonate, sodium hydrogen carbonate, dipotassium phosphate and disodium phosphate and organic bases such as triethylamine and diisopropylethylamine. As the reaction solvent, use is made of organic solvents, solely or as a mixture, such as water, ethers exemplified by dioxane and tetrahydrofuran, ketones exemplified by acetone and methyl ethyl ketone, esters exemplified by ethyl formate and ethyl acetate, halogenated hydrocarbons exemplified by chloroform, dichloromethane and dichloroethane, amides exemplified by N,N-dimethylformamide and N,N-diemthylacetamide, dimethylsulfoxide and acetonitrile, and among others, acetone, dichloromethane or water in combination with halogenated hydrocarbons are preferable. The reation is carried out at a temperature ranging from 0° to 100° C., but the temperature range of from 20° to 80° C. is normally preferable.

In the case of the starting compound [IX] or [XII] where $R^{25}$ is hydroxy group, this ring closure reaction is carried out by reacting the compound [IX] or [XII] with a phosphine derivative and azodicarboxylic acid diester or reacting the said compound with a phosphine derivative and carbon tetrachloride in the presence of a base such as triethylamine. As the phosphine derivative, use is made for example of triethylphosphine, tri(n-butyl)phosphine nnd triphenylphosphine, and among others, triphenylphosphine is preferable. As the azodicarboxylic acid diester, use is made for example of lower alkyl esters having one to four carbon atoms, and among others, azodicarboxylic acid diethyl ester is preferable. As the solvent, use is made for example of diethyl ether, diisopropyl ether, tetrahydrofuran, acetonitrile and N,N-dimethylformamide. The reaction is carried out at a temperature ranging from 0° to 80° C., but the temperature range of from 20° to 40° C. is normally preferred.

The methoxylation in the above reaction formula (4) is normally conducted easily by the method well known in the art, and is carried out for example by reacting an alkali metal salt of methanol represented by the formula:

$$MOCH_3 \qquad [XVIII]$$

wherein M is an alkali metal and halogenating agent with the compound [X]. The alkali metal salt of methanol includes lithium methoxide, sodium methoxide, potassium methoxide, etc. As the halogenating agent, use is made of halogen compounds capable of liberating a cationic halogen atom, such as halogen exemplified by chlorine and bromine, N-haloimides exemplified by N-chlorosuccinimide and N-bromosuccinimide, N-haloamides exemplified by N-chloroacetamide and N-bromoacetamide, N-halosulfonamides exemplified by N-chlorobenzenesulfonamide and N-chloro-p-toluenesulfonamide, 1-halobenzotriazoles and organic hypochlorites exemplified by tert-butyl hypochlorite. This reaction is carried out in a solvent. As the solvent, use can be made of, for example, tetrahydrofuran, dioxane, dichloromethane, chloroform, acetonitrile, methanol, N,N-dimethylformamide, N,N-dimethylacetamide, etc. or mixed solvents thereof as well as any of other solvents which do not affect this reaction. The reaction is carried out by dissolving or suspending the starting compound [XV] in the above-mentioned solvent and adding an alkali metal salt of methanol, methanol and halogenating agent to the solution or suspension to allow the reaction to proceed, whereby it is preferable to add not less than one mole of methanol, one to 3.5 moles of an alkali metal salt of methanol and about one to two moles of a halogenating agent against one mole of the starting compound [XV] to allow the reaction to proceed. The reaction proceeds easily under cooling or at room temperature to not more than 30° C., and is quenched by acidifying the reaction system. As the acid suitable for the cessation of the reaction, use is made for example of formic acid, acetic acid and trichloroacetic acid. After the cessation of the reaction, the excess halogenating agent is removed by the treatment with a reducing agent such as sodium thiosulfate and trialkyl ester of phosphorous acid. The reaction terminates normally in a few minutes to ten-odd hours, preferably in 0.5 to a few hours.

The derivatives [I] as obtained by the processes according to the above reaction formulas (1) through (4) may be obtainable in the form of a compound with any high degree of purity by the separation and purification means known per se such as solvent extraction, recrystallization and chromatography.

When the derivative [I] thus obtained has a free carboxy group, generally, it can form a salt through the action on a base. Therefore, the derivatives [I] are in some instances collected in the form of a salt, and the compound obtained in the form of a salt may be converted into the free form or into other salts. Furthermore, the derivatives [I] obtained in the free form may be converted into its salt. As the method of converting the derivatives [I] obtained in the form of a salt into the free form, for example, the method comprising the use of an acid is employed. The acid used varies depending upon the type of protective groups and other conditions, and as the acid, frequent use is made of inorganic acids such as hydrochloric acid, sulfuric acid and phosphoric acid and organic acids such as formic acid, acetic acid and p-toluenesulfonic acid. In addition acidic ion exchange resins and the like are employed. As the solvent, use is in many cases made of hydrophilic organic solvents such as acetone, tetrahydrofuran, methanol, ethanol and dioxane, water or mixed solvents. This method is normally conducted at room temperature, but may also be carried out under cooling to under warming. The reaction time varies with the types of acid and solvent as well as the temperature, but it is generally preferred that the reaction be completed in a short period. The resulting derivatives [I] in the free form can be isolated by the known method as mentioned above. When the derivatives [I] having a free carboxy group are obtained, the carboxy group can be derived into an ester by the known methods.

Of the starting compounds that are used in the abovedescribed processes for producing the derivatives [I], the starting compound [IV] can be synthesized, for example, in the above processes of the reaction formulas (1) through (4) by the procedure of deprotecting the compound [VII], [X], [XIII] or [XVI] or procedures similar thereto, and the starting compound [V] and the compounds [VI], [IX] and [XII] can be prepared for example by the below-described processes or their analogous processes. However, these examples are not intended to restrict the starting compounds, and any compound can be used, only if it meets the purpose of this invention. Specific examples of such compound are shown below in the reference examples.

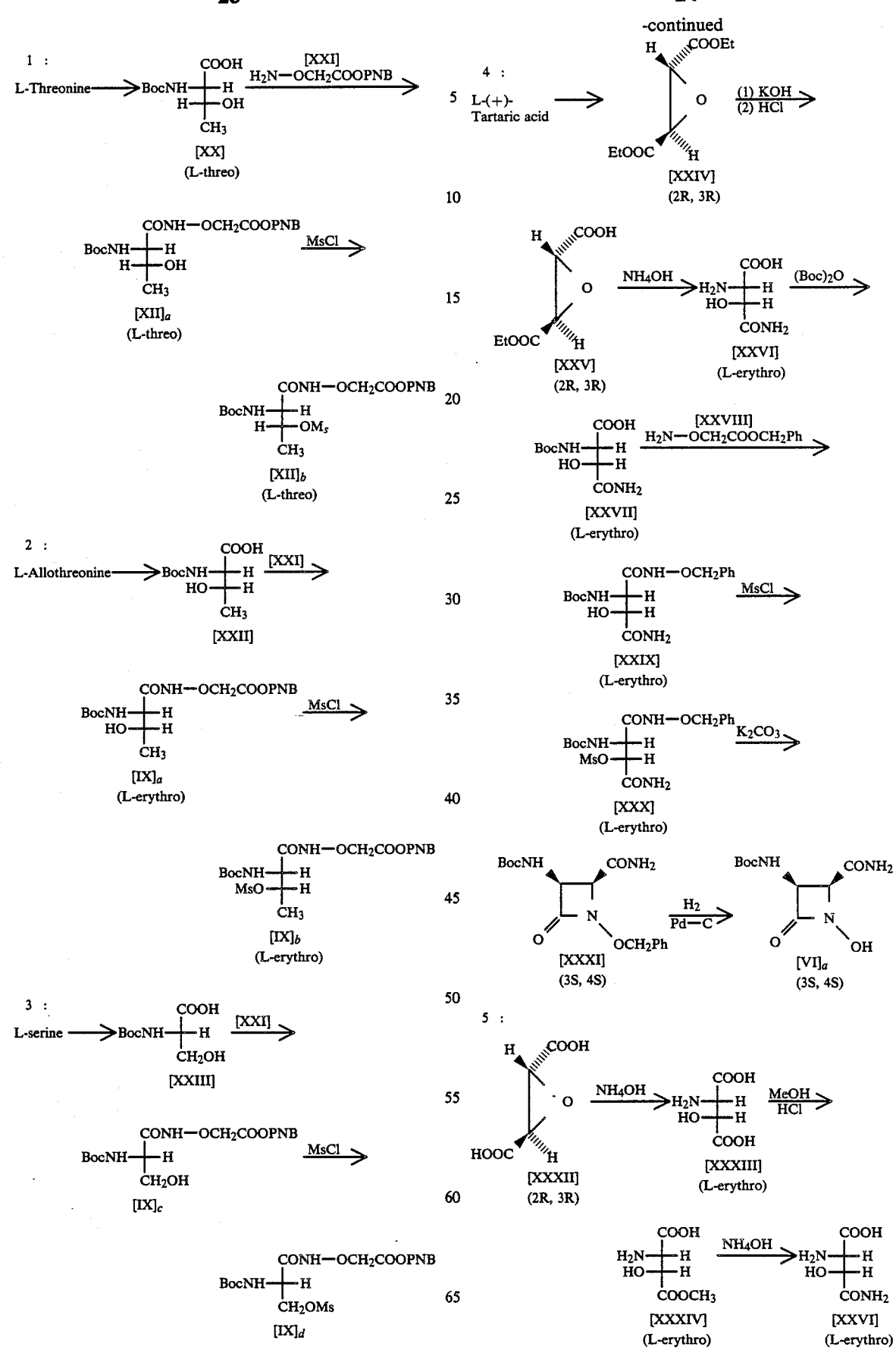

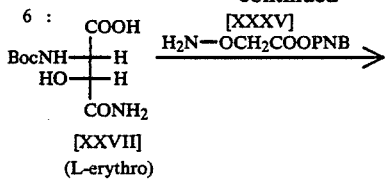

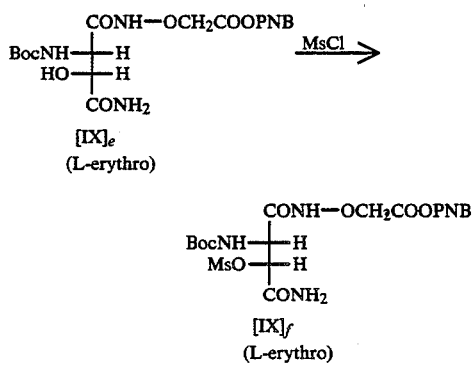

wherein Boc is tert-butoxycarbonyl group; Ph is phenyl group; PNB is p-nitrobenzyl group; Ms is methanesulfonyl group; Et is ethyl group.

The above processes (1) through (3) are examples of the process for producing an optically active isomer from an amino acid as a starting material. The conversion into diethyl (2R,3R)epoxysuccinate [XXIV] can be accomplished for example in accordance with the methods as described in Tetrahedron, 36, 87 (1980) and the Japanese Unexamined Patent Publication No. 110683/1981. (2R,3R)-epoxysuccinic acid [XXXII], the starting compound in the process (5), can be easily obtained for example by the fermentation process as described in The Journal of Medicinal Chemistry, 6, 233 (1963) etc., and is a highly valuable compound. The compound [XXXII] can be derived into the compound [XXIV] through esterification according to the conventional procedure, and is useful as a starting material for the production of optically active 2-azetidinones having various 4-substituents.

This invention is furthermore illustrated in detail in the below-described experiment example, examples and reference examples. However, it is to be understood that each of these examples is to be taken as an embodiment of the present invention and is not intended to limit the present invention, and that changes and modifications may be made without departing from the scope of the present invention.

Elution in column chromatography of the examples and reference examples was performed under observation by means of TLC (Thin Layer Chromatography), unless otherwise noted. In the observation by means of TLC, 60F$_{254}$ produced by Merck & Co. was used as a TLC plate, and the solvent utilized in column chromatography as a developing solvent was employed as an eluting solvent, with a UV detector being adopted as a detection method. The eluate containing the objective compound was also identified by a detection method utilizing the phenomenon that a spot on the TLC plate turns red to purplish red when being sprayed with 48% HBr, heated for hydrolysis, sprayed with Ninhydrin reagent and heated again, and the corresponding band of silica gel was scraped off and collected. In cases in which two kinds of solvents are used as a developing solvent, the solvent used first serves to elute by-products and the solvent employed then acts to elute the objective compound, unless otherwise noted. In the purification by column chromatography using "Amberlite" or "Sephadex", water was first used and aqueous ethanol solution then employed while increasing the concentration, unless otherwise specified in the examples and reference examples with reference to the developing solvent. In drying the objective compound, anhydrous sodium sulfate was used as a drying agent, unless otherwise referred.

"Amberlite" is produced by Rohm & Haas Co. in U.S.A, and "Dowex" is manufactured by Dow Chemical Co., while "Sephadex" is produced by Pharmacia Fine Chemicals, Inc. NMR spectra were measured with an EM 390 (90 MHz) or T60 (60 MHz) type spectrometer using tetramethylsilane as internal standard, and all the δ values were expressed in ppm. The symbols in the examples and reference examples have the following meanings:

s: Singlet
d: Doublet
q: Quartet
ABq: AB type quartet
d.d: Double doublet
d.t: Double triplet
m: Multiplet
br.: Broad
sh.: Shoulder
J: Coupling constant
Hz: Herz
mg: Milligram
g: Gram
ml: Milliliter
l: Liter
Ph: Phenyl
MeOH: Methanol
CHCl$_3$: Chloroform
DMSO: Dimethylsulfoxide
The ratio designates a volume/volume ratio.

Experiment Example

With regard to the objective compounds as obtained in Examples 2 to 5 and 17 to 19, MICs (μg/ml) were measured by the method to be described below and the results are tabulated in the following table.

Method of measurement

The MIC of a test compound was determined by the agar dilution method. Thus, 1.0 ml each of successively diluted, aqueous solutions of a test compound are poured in a petri dish, respectively, and then 9.0 ml of Trypticase soy agar was poured, followed by mixing. A suspension (about $10^8$ CFU/ml) of a test organism was smeared on the mixed agar plates. After incubation overnight at 37° C., the minimum concentration of the test compound to inhibit fully the growth of the test organism is determined as the minimal inhibitory concentration (MIC).

Test organisms (1) *Escherchia coli* NIHJ JC-2
(2) *Serratia marcescens* IFO 12648
(3) *Proteus vulgaris* IFO 3988
(4) *Proteus mirabilis* IFO 3849
(5) *Pseudomonas aeruginosa* IFO 3455
(6) *Enterobacter cloacae* IFO 12937
Results: MIC (μg/ml)

| Test compound | Test organism | | | | | |
|---|---|---|---|---|---|---|
| | (1) | (2) | (3) | (4) | (5) | (6) |
| Example 2 | 0.39 | 0.39 | 0.39 | 0.39 | >100 | 12.5 |
| Example 3 | 0.39 | 0.39 | <0.1 | <0.1 | 6.25 | 12.5 |
| Example 4 | 12.5 | 6.25 | 1.56 | 12.5 | 25 | >100 |
| Example 5 | 0.78 | 1.56 | 0.78 | 1.56 | 6.25 | 50 |
| Example 17 | 0.39 | 0.39 | 0.39 | 0.39 | 100 | 0.78 |
| Example 18 | 0.78 | 0.39 | <0.1 | <0.1 | 12.5 | 0.78 |
| Example 19 | 0.39 | 0.39 | 0.39 | 0.39 | >100 | 50 |

EXAMPLE 1

Synthesis of (3S,4S)-3-(tert-butoxycarbonylamino)-4-methyl-1-(p-nitrobenzyloxycarbonylmethoxy)-2-azetidinone;

In 400 ml of acetone is dissolved 2.32 g of N-(tert-butoxycarbonyl)-O-methanesulfonyl-L-threonine-N'-(p-nitrobenzyloxycarbonylmethoxy)amide, and 1.66 g of potassium carbonate is added to the solution. The temperature of the reaction solution is gradually increased until it reaches 60° C. over the period of 30 minutes, and stirring is effected at the same temperature for further 30 minutes. The reaction solution is filtered, and the filtrate is concentrated under reduced pressure. Water and ethyl acetate are added to the residue, followed by shaking. The ethyl acetate layer is separated, washed successively with water, dilute hydrochloric acid and aqueous sodium chloride solution, and dried over anhydrous magnesium sulfate. The solvent is distilled off under reduced prsssure, and the residue is purified by column chromatography (150 g of silica gel; ethyl acetate-n-hexane=1:1) to give 1.22 g (64.8%) of the above-identified compound as a yellowish oily product. The product, upon standing in a refrigerator, solidifies and is washed with petroleum ether to give the compound, m.p. 71°-75° C.

IR (Neat)cm$^{-1}$: 3,320, 2,970, 1,770(br.), 1,700, 1,520, 1,250.

NMR(d$_6$-DMSO)δ: 1.31(3H,d,J=6 Hz,C$_4$-CH$_3$), 1.35(9H,s,3×CH$_3$), 3.75(1H,d .t,J=2&6 Hz, C$_4$-H), 3.97(1H,d.d,J=2&9 Hz,C$_3$-H), 4.70(2H,ABq,J=15 Hz,OCH$_2$COO), 5.33(2H,s,COOCH$_2$), 7.35 (1H,d,J=9 Hz,C$_3$-NH), 7.66(2H,d,J=9 Hz,aromatic proton), 8.22(2H,d,J-9 Hz,aromatic proton).

Elemental analysis, for C$_{18}$H$_{23}$N$_3$O$_8$

| | C (%) | H (%) | N (%) |
|---|---|---|---|
| Calcd. | 52.81 | 5.66 | 10.26 |
| Found | 52.97 | 5.72 | 10.34 |

[α]$_D^{25}$ −66.5° (c = 0.8, MeOH)

EXAMPLE 2

Synthesis of (3S,4S)-3-[2-aminothiazol-4-yl)-(Z)-2-methoxyiminoacetamido]-1-carboxymethoxy-4-methyl-2-azetidinone monosodium salt.

(a) In 40 m( of dichloromethane is dissolved 940 mg of (3S,4S)-3-(tert-butoxycarbonylamino)-4-methyl-1-(p-nitrobenzyloxycarbonylmethoxy)-2-azetidinone, and 4 ml of anisole and 20 ml of trifluoroacetic acid are added to the solution under ice-cooling with stirring. After the mixture is stirred under ice-cooling for 1.5 hours, 40 ml of toluene is added to the reaction solution, followed by concentration under reduced pressure. The residue is suspended in 40 ml of dichloromethane, 1.93 ml of triethylamine and 1.145 g of 2-(2-chloroacetamidothiazol-4-yl)-(Z)-2-methoxyiminoacetyl chloride hydrochloride are added to the suspension under ice-cooling, followed by stirring for 1 hour. The solvent is distilled off under reduced pressure, and 10 ml of water and 10 ml of tetrahydrofuran are added to the residue. The mixture is adjusted to pH 7 with an aqueous sodium hydrogen carbonate solution, and stirred under ice-cooling for 30 minutes. The reaction solution is extracted with ethyl acetate, and the extract is washed with an aqueous sodium hydrogen carbonate solution, water, dilute hydrochloric acid and aqueous sodium chloride solution successively, and dried over anhydrous magnesium sulfate. The solvent is distilled off under reduced pressure, and the residue is purified by column chromatography (60 g of silica gel:ethyl acetate-n-hexane=2:1). The purified product is solidified with ether to give 763 mg (58.3%) of (3S,4S)-3-[2-(2-chloroacetamidothiazol-4-yl)-(Z)-2-methoxyiminoacetamido]-4-methyl-1-[p-nitrobenzyloxycarbonylmethoxy)-2-azetidinone as a colorless powder, m.p. 102°-106° C. (decomp.).

IR (KBr) cm$^{-1}$: 1,760, 1,670, 1,525, 1,350, 1,040.

NMR (d$_6$-DMSO)δ: 1.40(3H,d,J=6 Hz,C$_4$-CH$_3$), 3.8-4.1(1H,m, C$_4$-H), 3.87(3H,s,OCH$_3$), 4.25-4.50(1H,m,C$_3$-H), 4.34(2H,s,ClCH$_2$), 4.75(2H,ABq,J=15 Hz,OCH$_2$COO), 5.34(2H,s,COOCH$_2$), 7.38 (1H,s,thiazole-5-H), 7.65(2H,d,J=9 Hz,aromatic proton), 8.18(2H,d,J=9 Hz,aromatic proton), 9.26(1H,d,J=8 Hz,C$_3$-NH), 12.85(1H,br.s,thiazole-2-NH). [α]$_D^{28}$ −60.9° (c=0.75,MeOH)

(b) In a mixed solution of 10 ml of tetrahydrofuran and 5 ml of water is dissolved 626 mg of the product as obtained under the above (a), and 156 mg of sodium N-methyldithiocarbamate, is added to the solution, followed by stirring at room temperature for 40 minutes. 144 mg of sodium N-methyldithiocarbamate is furthermore added, and the mixture is stirred for further 50 minutes. Ethyl acetate and aqueous sodium chloride solution are added to the reaction solution, which is then shaken. The organic layer is separated and washed with aqueous sodium chloride solution. The solution is dried over anhydrous magnesium sulfate and concentrated under reduced pressure, and the residue is purified by column chromatography (50 g of silica gel: ethyl acetate) to give 326 mg (60.2%) of (3S,4S)-3-[2-(2-aminothiazol-4-yl)-(Z)-2-methoxyiminoacetamido]-4-methyl-1-(p-nitrobenzyloxycarbonylmethoxy)-2-azetidinone as a yellowish powder, m.p. 90°-95° C. (decomp.).

IR (KBr) cm$^{-1}$: 1,775, 1,670, 1,535, 1,350.

NMR (d$_6$-DMSO)δ: 1,37(3H,d,J=6 Hz,C$_4$-CH$_3$), 3.82(3H,s,OCH$_3$), 3.8–4.1(1H,m,C$_4$-H), 4.32(1H,d.d,J=2&8 Hz,C$_3$-H), 4.73 (2H,ABq,J=15 Hz,OCH$_2$COO), 5.33(2H,s,COOCH$_2$), 6.67(1H,s, thiazole-5-H), 7.13(2H,br.s,thiazole-2-NH$_2$), 7.65(2H,d,J=9 Hz,aromatic proton), 8.18(2H,d,J=9 Hz,aromatic proton), 9.10(1H,d,J=8 Hz,C$_3$-NH) [α]$_D^{29}$ −68.8° (c=0.65,MeOH)

(c) In a mixed solution of 20 ml of tetrahydrofuran and 20 ml of water dissolved 300 mg of the product as obtained under the above (b), and 300 mg of 10% palladium-charcoal added to the solution, followed by stirring under a hydrogen atmosphere at room temperature for 1 hour. 50 mg of sodium hydrogen carbonate is added to the reaction solution, which is then stirred under a hydrogen atmosphere for further 3 hours. The catalyst is filterd off, and the filtrate is concentrated under reduced pressure. The residue is purified by column chromatography (Amberlite XAD-2, 250 ml; water) and lyophilized to give 167 mg (67.4%) of the above-identified compound as a colorless poweder.

IR (KBr) cm$^{-1}$: 1,770, 1,660, 1,615, 1,530, 1,040.
NMR (d$_6$-DMSO)δ: 1.36(3H,d,J=6 Hz,C$_4$-CH$_3$), 3.77(3H,s,OCH$_3$), 3.7-4.1(1H,m,C$_4$-H), 3.95(2H,s,ClCH$_2$), 4.23(1H,d.d,J=2&8 Hz,C$_3$-H), 6.63(1H,s,thiazole-5-H), 7.13(2H,br.s,thiazole-2-NH$_2$), 9.18(1H,d,J=8 Hz,C$_3$-NH).

Elemental analysis, for C$_{12}$H$_{14}$N$_5$NaO$_6$S.1.5H$_2$O

|  | C (%) | H (%) | N (%) |
|---|---|---|---|
| Calcd. | 35.47 | 4.22 | 17.24 |
| Found | 35.42 | 4.52 | 17.06 |
| [α]$_D^{29}$ −72.8° (c = 0.7, water) | | | |

EXAMPLE 3

Synthesis of (3S,4S)-3-[2-(2-aminothiazol-4-yl)-(Z)-2-(1-carboxy-1-methylethoxyimino)acetamido]-1-carboxymethoxy-4-methyl-2-azetidinone disodium salt.

(a) In 40 ml of dichloromethane is dissolved 1.02 g of (3S,4S)-3-[tert-butoxycarbonylamino)-4-methyl-1-(p-nitrobenzyloxycarbonylmethoxy)-2-azetidinone, and 4 ml of anisole and 20 ml of trifluoroacetic acid are added to the solution under ice-cooling with stirring. After the stirring under ice-cooling for 1.5 hours, 20 ml of toluene is added to the reaction solution and the mixture is concentrated under reduced pressure. The residue is suspended in 40 ml of dichloromethane, and 2.1 ml of triethylamine and 1.62 g of 2-(2-chloroacetamidothiazol-4-yl)-(Z)-2-[1-methyl-1-(p-nitrobenzyloxycarbonyl)ethoxyimino]acetyl chloride hydrochloride (prepared by the method as described in the Japanese Unexamined Patent Publication No. 131758/1982) are added to the suspension under ice-cooling, followed by stirring for 1,5 hours. The reaction solution is concentrated under reduced pressure, ethyl acetate and water are added to the residue, followed by shaking. The ethyl acetate layer is separated, washed with aqueous sodium hydrogen carbonate solution, aqueous sodium chloride solution, dilute hydrochloric acid and aqueous sodium chloride solution successively, and dried over anhydrous magnesium sulfate. The solvent is distilled off under reduced pressure, and the residue is purified by column chromatography (80 g of silica gel; ethyl acetate-n-hexane=3:2) to give 918 mg (47.3%) of (3S,4S)-3-{2-(2-chloroacetamidothiazol-4-yl)-(Z)-2-[1-methyl-1-(p-nitrobenzyloxycarbonyl)ethoxyimino]acetamido}-4-methyl-1-(p-nitrobenzyloxycarbonyl-methoxy)-2-azetidinone as a colorless foamy product.

IR (KBr) cm$^{-1}$ : 1,785, 1,765, 1,750, 1,680, 1,525, 1,350.

NMR (d$_6$-DMSO)67 : 1,41(3H,d,J=6 Hz,C$_4$-CH$_3$), 1.50(6H,s,2×CH$_3$), 3.8-4.15(1H,m,C$_4$-H), 4.34(2H,s,ClCH$_2$), 4.44(1H,d.d,J=2&8 Hz,C$_3$-H), 4.75(2H,ABq,J=17 Hz,OCH$_2$COO), 55.33(4H,s, 2×COOCH$_2$), 7.37(1H,s,thiazole-5-H), 7.58(2H,d,J=9 Hz, aromatic proton), 7.63(2H,d,J=9 Hz,aromatic proton), 8.05(2H,d,J=9 Hz,aromatic proton), 8.18(2H,d,J=9 Hz,aromatic proton), 9.18(1H,d,J=8 Hz,C$_3$-NH), 12.87(1H,br.s,thiazole-2-NH).

(b) In a mixed solution of 15 ml of tetrahydrofuran and 5 ml of water is dissolved 784 mg of the product as obtained under the above (a), and 130 mg of sodium N-methyldithiocarbamate is added to the solution under ice-cooling with stirring. The mixture is stirred at room temperature for 1 hour, and 130 mg of sodium N-methyldithiocarbamate is furthermore added, followed by stirring for another 1 hour. Ethyl acetate and aqueous sodium chloride solution are added oo the reaction solution, and after the mixture is shaken, the organic layer is separated, washed with aqueous sodium chloride solution, dried over anhydrous magnesium sulfate and concentrated under reduced pressure. The residue is purified by column chromatography (silica gel 90 g; ethyl acetate-n-hexane=2:1, then 4:1) to give 583 mg (83.3 %) of (3S,4S)-3-{2-(2-aminothiazol-4-yl)-(Z)-2-[1-methyl-1-(p-nitrobenzyloxycarbonyl)ethoxyimino]acetamido}-4-methyl-1-(p-nitrobenzyloxycarbonylmethoxy)-2-azetidinone as a yellowish foamy product.

IR (KBr) cm$^{-1}$: 3,370, 3,120, 1,780, 1,750, 1,680, 1,525, 1,350.

NMR (d$_6$-DMSO)67: 1.40(3H,d,J=6 Hz,C$_4$-CH$_3$), 1.51(6H,s,2×CH$_3$), 3.80-4.10(1H,m,C$_4$-H), 4.38(1H,d.d,J=2&8 Hz,C$_3$-H), 4.74(2H,ABq,J=17 Hz,OCH$_2$COO), 5.34(4H,s,2×COOCH$_2$), 6.71 (1H,s,thiazole-5H), 7.25(2H,br.s,thiazole-2-NH$_2$), 7.61(2H,d,J=9 Hz,aromatic proton), 7.65(2H,d,J=9 Hz,aromatic proton), 8.11(2H,d,J=9 Hz,aromatic proton), 8.17(2H,d, J=9 Hz,aromatic proton), 9.02(1H,d,J=8 Hz,C$_3$-NH).

(c) In a mixed solution of 15 ml of tetrahydrofuran and 15 ml of water is dissolved 490 mg of the product as obtained under the above (b), and 490 mg of 10% palladium-charcoal is added to the solution, followed by stirring under a hydrogen atmosphere at room temperature for 1.5 hours. 118 mg of sodium hydrogen carbonate is added to the reaction solution, followed by stirring under a hydrogen atmosphere for further 2 hours. The catalyst is filtered off, and washed with a mixed solution (1:1) of tetrahydrofuran and water. The filtrate and washings are combined and concentrated under reduced pressure to distill off the tetrahydrofuran. The residual aqueous solution is washed with ethyl acetate and concentrated again under reduced pressure to about 5 ml. The residue is purified by column chromatography (Amberlite XAD-2, 250 ml; water) and lyophilized to give 238 mg of a yellow powder. The powder is dissolved in a small amount of water, followed by purification by column chromatography (Amberlite XAD-2, 200 ml; water) and lyophilization to give 213 mg (58.1%) of the above-identified compound as a yellowish powder.

IR (KBr) cm$^{-1}$: 1,770, 1,660, 1,620(br.), 1,530, 1,410.
NMR (d$_6$-DMSO)δ: 1,25-1,50(9H,m,3×CH$_3$), 3.80-4.25(3H,m, OCH$_2$COO&C$_4$-H), 4.40(1H,d.d,J=2&8 Hz,C$_3$-H), 6.71(1H,s,thiazole-5-H), 7.10(2H,br. s,thiazole-2-NH$_2$), 11.36(1H,d,J=8 Hz,C$_3$-NH).

Elemental analysis, for C$_{15}$H$_{17}$N$_5$Na$_2$O$_8$S.2.8H$_2$O

|  | C (%) | H (%) | N (%) |
|---|---|---|---|
| Calcd. | 34.40 | 4.35 | 13.37 |
| Found | 34.29 | 4.23 | 13.65 |
| [α]$_D^{24}$ −50.7° (c = 0.9, water) | | | |

EXAMPLE 4

Synthesis of (3S,4S)-1-carboxymethoxy-3-[(D)-2-(4-ethyl-2,3-dioxopiperazine-1-carbonylamino)-2-phenylacetamido]-4-methyl-2-azetidinone monosodium salt.

(a) In 40 ml of dichloromethane is dissolved 1.02 g of (3S,4S)-3-tert-butoxycarbonylamino)-4-methyl-1-(p-nitrobenzyloxycarbonylmethoxy)-2-azetidinone, and 4 ml of anisole and 10 m( of trifluoroacetic acid are added to the solution under ice-cooling with stirring. After the stirring under ice-cooling for 75 minutes, 20 ml of toluene is added to the reaction solution, and the mixture is concentrated under reduced pressure. Ethyl acetate and aqueous sodium chloride solution are added to the residue, and after the mixture is neutralized under ice-cooling with sodium hydrogen carbonate, the ethyl acetate layer is separated, washed with aqueous sodium chloride solution, dried over anhydrous magnesium sulfate and concentrated under reduced pressure. The residue is dissolved in 15 ml of N,N-dimethylformamide, and 798 mg of (D)-2-(4-ethyl-2,3-dioxopiperazine-1-carbonylamino)-2-phenylacetic acid and 567 mg of dicyclohexylcarbodiimide are added to the solution, followed by stirring at room temperature for 14 hours. The insoluble matter is filtered off, and the filtrate is concentrated under reduced pressure. The residue is dissolved in ethyl acetate, and the solution is washed with aqueous sodium hydrogen carbonate solution, and aqueous sodium chloride solution successively, and dried over anhydrous magnesium sulfate. The solvent is distilled off under reduced pressure, and the residue is purified by column chromatography (silica gel, 100 g; ethyl acetate) to give 164 mg (10.7%) of (3S,4S)-3-[(D)-2-(4-ethyl-2,3-dioxopiperazine-1-carbonylamino)-2-phenylacetamido]-4-methyl-1-(p-nitrobenzyloxycarbonylmethoxy)-2-azetidinone as a colorless foamy product.

IR (KBr) cm$^{-1}$: 3,300, 2,930, 1,780, 1,715, 1,680, 1,515, 1,350, 1,185. NMR (d$_6$-DMSO)δ: 1.07(3H,t,J=7.5 Hz,CH$_2$C$\underline{H_3}$), 1.33(3H,d,J=6 Hz,C$_4$-CH$_3$), 3.2–4.1(7H,m,3×NCH$_2$&C$_4$-H), 4.22(1H,d.d,J=2& 7Hz,C$_3$-H), 4.75(2H,br.s,OCH$_2$COO), 5.34(2H,s,COOCH$_2$), 5.43(1H,d,J=7.5 Hz,PhC$\underline{H}$), 7.2–7.5(5H,m,Ph), 7.66(2H,d, J=9 Hz,aromatic proton), 8.20(2H,d,J=9 Hz,aromatic proton), 9.11(1H,d,J=7 Hz,C$_3$-NH), 9.80(1H,d,J=7.5 Hz,PhCHN$\underline{H}$).

(b) In a mixed solution of 20 ml of tetrahydrofuran and 20 ml of water is dissolved 336 mg of the product as obtained under the above (a), and 340 mg of 10% palladium-charcoal is added to the solution, followed by stirring under a hydrogen atmosphere at room temperature for 40 minutes. 46 mg of sodium hydrogen carbonate is added to the mixture under ice-cooling, and the catalyst is filtered off and washed with a mixed solution (1:1) of tetrahydrofuran and water and water successively. The filtrate and washings are combined, and the tetrahydrofuran is distilled off under reduced pressure. The residual aqueous solution is washed with ethyl acetate and concentrated again under reduced pressure. The residue is purified by column chromatography (Amberlite XAD-2, 260 ml; water; 10% ethanol and 20% ethanol) and lyophilized to give 240 mg (80.5%) of the above-identified compound as a colorless powder.

IR (KBr) cm$^{-1}$: 1,770, 1,715, 1,680, 1,610, 1,510, 1,370, 1,185.

NMR (d$_6$-DMSO)δ: 1.07(3H,t,J=7.5 Hz,CH$_2$C$\underline{H_3}$), 1.33(3H,d,J=6 Hz,C$_4$-$\overline{CH_3}$), 3.2–4.1(7H,m,3×NCH$_2$&C$_4$-H), 4.23(1H,d.d,J=1.5& 7 Hz,C$_3$-H), 5.46(1H,d,J=7.5 Hz,PhC$\underline{H}$), 7.15–7.55(5H,m,Ph), 9.48(1H,d,J=7 Hz,C$_3$-$\overline{NH}$), 9.77(1H,d,J=7.5 Hz,PhCHN$\underline{H}$).

Elemental analysis, for C$_{21}$H$_{24}$N$_5$NaO$_8$.2.5H$_2$O

|  | C (%) | H (%) | N (%) |
|---|---|---|---|
| Calcd. | 46.50 | 5.39 | 12.91 |
| Found | 46.39 | 5.34 | 13.01 |

$[\alpha]_D^{24}$ −76.6° (c = 0.7, water).

EXAMPLE 5

Synthesis of (3S)-3-[2-(2-aminothiazol-4-yl)-(Z)-2-(1-carboxy-1-methylethoxyimino)acetamido]-1-carboxymethoxy-2-azetidinone disodium salt.

(a) In 90 ml of dried tetrahydrofuran are dissolved 1.78 g of N-(tert-butoxycarbonyl)-L-serine-N'-(p-nitrobenzyloxycarbonylmethoxy)amide and 1.57 g of triphenylphosphine, and 0.94 ml of diethyl azodicarboxylate is added dropwise to the solution, followed by stirring at room temperature for 5 hours. 0.393 g of triphenylphosphine and 0.24 ml of diethyl azodicarboxylate are furthermore added, followed by stirring at room temperature for another 13 hours. The reaction solution is concentrated under reduced pressure, and the residue is purified by column chromatography (silica gel, 100 g; ethyl acetate-n-hexane,2:1), and the eluates containing the objective compound are collected and concentrated. Ether is added to the residue, and the resulting colorless solid is collected by filtration to give 1.86 g of a mixture of (3S)-3-(tert-butoxycarbonylamino)-1-(p-nitrobenzyloxycarbonylmethoxy)-- 2-azetidinone and diethoxycarbonylhydrazine. The objective compound shows a purity of 63% and is obtained in the yield of 69% as converted to the purity.

IR (KBr) cm$^{-1}$: 1,780, 1,755, 1,680, 1,520

NMR (d$_6$-DMSO)67: 1.37(9H,s,3×CH$_3$), 3.43(1H,d.d,J=3&4.5 Hz, C$_4$-H), 3.78(1H,t,J=4.5 Hz,C$_4$-H), 4.3–4.6(1H,m,C$_3$-H), 4.69(2H,s,OCH$_2$COO), 5.33(2H,s,COOCH$_2$), 7.47(1H,d,J=9 Hz,C$_3$-NH), 7.65(2H,d,J=9 Hz, aromatic proton), 8.22 (2H,d,J=9 Hz, aromatic proton).

(b) In 40 ml of dichloromethane is dissolved 1.57 g of the product as obtained under the above (a), and 4 ml of anisole and 220 ml of trifluoroacetic acid are added to the solution under ice-cooling with stirring. After the stirring under ice-cooling for 1 hour, 20 ml of toluene is added to the reaction solution, and the mixture is concentrated under reduced pressure. The residue is suspended in 40 ml of dichloromethane, and 2.1 ml of triethylamine and 1.62 g of 2-(2-chloroacetamidothiazol-4-yl)-(Z)-2-[1-methyl-1-(p-nitrobenzyloxycarbonyl)ethoxyimino]acetyl chloride hydrochloride are added to the suspension under ice-cooling, followed by stirring for 1.5 hours. The reaction solution is concentrated under reduced pressure, and ethyl acetate and water are added to the residue, followed by shaking. The ethyl acetate layer is separated, washed with aqueous sodium hydrogen carbonate solution, aqueous sodium chloride solution, dilute hydrochloric acid and aqueous sodium chloride solution successively, and dried over anhydrous magnesium sulfate. The solvent is distilled off, and residue is purified by column chromatography (silica gel, 100 g; ethyl acetate-CHCl$_3$=1:1, then 2:1) to give 511 mg (26.8%) of (3S)-3-{2-(2-chloroacetamidothiazol-4-yl)-(Z)-2-[1-methyl-1-(p-nitrobenzyloxycarbonyl)ethoxyimino]acetamido}-1-(p-nitrobenzyloxycarbonylmethoxy)-2-azetidinone as a colorless powder.

IR (KBr) cm$^{-1}$: 3,400(br.), 1,785, 1,750, 1,680, 1,525, 1,350.

NMR (d$_6$-DMSO)δ: 1.51(6H,s,2×CH$_3$), 3.5–3.65(1H,m,C$_4$-H), 3.8–4.1(1H,m,C$_4$-H), 4.34(2H,s,ClCH$_2$), 4.75(2H,s,OCH$_2$COO), 4.6–5.0(1H,m,C$_3$-H), 5.33(4H,s,2×COOCH$_2$), 7.37(1H,s,thiazole-5-H), 7.59(2H,d,J=9 Hz,aromatic proton), 7.66(2H,d,J=9 Hz,aromatic proton), 8.06(2H,d,J=9 Hz,aromatic proton), 8.19(2H,d,J=9 Hz,aromatic proton), 9.15(1H,d,J=8 Hz,C$_3$-NH), 12.86(1H,br.s,thiazole-2-NH).

(c) In a mixed solution of 12 ml of tetrahydrofuran and 4 ml of water is dissolved 480 mg of the product as obtained under the above (b), and 81 mg of sodium N-methyldithiocarbamate is added to the solution under ice-cooling with stirring. After the stirring at room temperature for 1 hour, 41 mg of sodium N-methyldithiocarbamate is furthermore added to the mixture, followed by stirring for another 1 hour. Ethyl acetate and aqueous sodium chloride solution are added to the reaction solution, and after the mixture is shaken, the organic layer is separated, washed with aqueous sodium chloride solution, dried over anhydrous magnesium sulfate, and concentrated under reduced pressure. The residue is purified by column chromatography (silica gel, 50 g: ethyl acetate-n-hexane=4:1, then ethyl acetate alone) to give 357 mg (82.7%) of (3S)-3-{2-(2-aminothiazol-4-yl)-(Z)-2-[1-methyl-1-(p-nitrobenzyloxycarbonyl)ethoxyimino]acetamido}-1-(p-nitrobenzyloxycarbonylmethoxy)-2-azetidinone as a yellow foamy product.

IR (KBr) cm$^{-1}$: 3,370,(br.), 3,120, 1,780, 1,740, 1,680, 1,525, 1,350.

NMR (d$_6$-DMSO)67: 1.48(6H,s,2×CH$_3$), 3.5–3.7(1H,m,C$_4$-H), 3.8–4.1(1H,m,C$_4$-H), 4.74(2H,s,OCH$_2$COO), 4.65-4.95 (1H,m,C$_3$-H), 5.33(4H,s,2×COOCH$_2$), 6.70(1H,s,thiazole-5-H), 7.25(2H,br.s,thiazole-2-NH$_2$), 7.62(2H,d,J=9 Hz, aromatic proton), 7.65(2H,d,J=9 Hz,aromatic proton), 8.11(2H,d,J=9 Hz,aromatic proton), 8.20(2H,d,J=9 Hz, aromatic proton), 9.02(1H,d,J=8 Hz,C$_3$-NH).

(d) In a mixed solution of 15 ml of tetrahydrofuran and 15 ml of water is dissolved 310 mg of the product as obtained under the above (c), and 310 mg of 10% palladium-charcoal is added to the solution, followed by stirring under a hydrogen atmosphere at room temperature for 1.5 hours. A solution of 76 mg of sodium hydrogen carbonate in 5 ml of water is added to the reaction solution under ice-cooling. The catalyst is filtered off and washed with a mixed solution (1:1) of tetrahydrofuran and water. The filtrate and washing are combined and concentrated under reduced pressure to distill off the tetrahydrofuran. The residual aqueous solution was washed with ethyl acetate and concentrated again under reduced pressure. The residue is purified by column chromatography.

(Amberlite XAD-2, 250 ml; water) and lyophilized to give 149 mg (65.4%) of the above-identified compound as a colorless powder.

IR (KBr) cm$^{-1}$: 1,770, 1,660, 1,605(br.), 1,535, 1,410.
NMR (d$_6$-DMSO)δ: 1,40(9H,s,3×CH$_3$), 3.5–3.7(1H,m,C$_4$-H), 3.7–3.9(1H,m,C$_4$-H), 4.03(2H,br.s,OCH$_2$COO), 4.65–4.95(1H,m,C$_3$-H), 6.70(1H,s,thiazole-5-H), 7.02(2H,thiazole-2-NH$_2$), 11.49(1H,d,J=9 Hz,C$_3$-NH).

Elemental analysis, for C$_{14}$H$_{15}$N$_5$Na$_2$O$_8$S.2.5H$_2$O

|  | C (%) | H (%) | N (%) |
|---|---|---|---|
| Calcd. | 33.34 | 4.00 | 13.89 |
| Found | 33.54 | 3.94 | 13.90 |
| [α]$_D^{25}$ −141.7° (c = 0.5, water) | | | |

EXAMPLE 6

Synthesis of (3S,4S)-3-(tert-butoxycarbonylamino)-4-carbamoyl-1-(p-nitrobenzyloxycarbonylmethoxy)-2-azetidinone (the alkylation method).

In 5 ml of acetonitrile is suspended 123 mg of (3S,4S)-3-(tert-butoxycarbonylamino)-4-carbamoyl-1-hydroxy-2-azetidinone, and 0.08 ml of triethylamine is added to the suspension under ice-cooling with stirring, resulting in a clear solution. Then, 150 mg of P-nitrobenzyl bromoacetate is added, and the mixture is stirred at room temprature for 1 hour, whereby crystals separate out. The solvent is distilled off under reduced pressure, and a mixed solution (2:1) of ethyl acetate and tetrahydrofuran and water are added to the residue, followed by shaking. The organic layer is separated, dried over anhydrous magnesium sulfate and concentrated under reduced pressure. A mixed solution (1:2) of ethyl acetate and ether is added to the remaining crystals, and filtration is effected to give 144 mg (65.8%) of the above-identified compound as colorless crystals, m.p. 192°–194° C. (decomp.).

IR (KBr) cm$^{-1}$: 3.360, 1,790, 1,690, 1,520, 1,350.
NMR (d$_6$-DMSO)δ: 1.36(9H,s,3×CH$_3$), 4.60(1H,d,J=6 Hz,C$_4$-H), 4.73(2H,s,OCH$_2$COO), 4.95(1H,d.d,J=6&9 Hz,C$_3$-H), 5.28(2H,ABq,J=15 Hz,COOCH$_2$), 7.02(1H,d,J=9 Hz,C$_3$-NH), 7.25-7.55(2H,m,CONH$_2$), 7.66(2H,d,J=9 Hz, aromatic proton), 8.22(2H,d,J=9 Hz,aromatic proton).

Elemental analysis, for C$_{18}$H$_{22}$N$_4$O$_9$

|  | C (%) | H (%) | N (%) |
|---|---|---|---|
| Calcd. | 49.32 | 5.06 | 12.78 |
| Found | 49.08 | 5.07 | 12.57 |

EXAMPLE 7

Synthesis of (3S,4S)-3-tert-butoxycarbonylamino)-4-carbamoyl-1-(p-nitrobenzyloxycarbonylmethoxy)-2-azetidinone (the ring-closure method).

In 100 ml of acetone is suspended 534 mg of L-erythro-N$^α$-(p-nitrobenzyloxycarbonylmethoxy)-N-(tert-butoxycarbonyl-3-methanesulfonyloxyaspartic acid diamide, and 415 mg of potassium carbonate is added to the suspension. The reaction temperature is grandually elevated until it reaches 60° C. over the period of 20 minutes, and stirring is conducted at the same temperature for 25 minutes. The reaction solution is filtered, and after the filtrate is concentrated under reduced pressure, the residue is dissolved in a mixed solution (4:1) of ethyl acetate and tetrahydrofuran. The solution is washed with aqueous sodium chloride solution and dried over anhydrous magnesium sulfate, and the solvent is distilled off under reduced pressure. A mixed solution (1:2) of ethyl acetate and ether is added to the residue, and crystals which separate out are recovered by filtration to give 266 mg (60.7%) of the above-identified compound which is in agreement with the compound as obtained in Example 6.

EXAMPLE 8

Synthesis of (3S,4S)-3-[2-(2-aminothiazol-4-yl)-(Z)-2-methoxyiminoacetamido]-4-carbamoyl-1-carboxymethoxy-2-azetidinone monosodium salt.

(a) In 20 ml of dichloromethane is suspended 438 mg of (3S,4S)-3-(tert-butoxycarbonylamino)-4-carbamoyl-1-(p-nitrobenzyloxycarbonylmethoxy)-2-azetidinone, and 2 ml of anisole and 10 ml of trifluoroacetic acid are added to the suspension under ice-cooling with stirring. After the stirring under ice-cooling for 2 hours, 20 ml of dioxane is added to the reaction solution, which is then concentrated under reduced pressure. 20 ml of dioxane is again added to the residue, followed by concentration under reduced pressure. 20 ml of dichloromethane and 10 ml of tetrahydrofuran are added to the residue, and 0.84 ml of triethylamine and 498 mg of 2-(2-chloroacetamidothiazol-4-yl)-(Z)-2-methoxyiminoacetyl chloride hydrochloride are added to the mixture under ice-cooling with stirring, followed by stirring under ice-cooling for 2 hours. The solvent is distilled off under reduced pressure, and 15 ml of tetrahydrofuran and 15 ml of water are added to the residue, followed by neutralization with sodium hydrogen carbonate. After the mixture is stirred under ice-cooling for 1 hour, the tetrahydrofuran is distilled off under reduced pressure. 20 ml of water is added to the residue, and crystals which separate out are recovered by filtration, washed with aqueous sodium hydrogen carbonate solution, water, ether, ethyl acetate and ether successively to give 363 mg (60.7%) of (3S,4S)-4-carbamoyl-3-[2-(2-chloroacetamidothiazol-4-yl)-(Z)-2-methoxyiminoacetamido]-1-(-nitrobenzyloxycarbonylmethoxy)-2-azetidinone as colorless crystals, m.p. 210°–213° C. (decomp.).

IR (KBr) cm$^{-1}$: 3,420, 3,220, 1,790, 1,750, 1,685, 1,670

NMR (d$_6$-DMSO)67: 3.88(3H,s,OCH$_3$), 4.35(2H,s,ClCH$_2$), 4.65–4.85(3H,m,OCH$_2$COO&C$_4$-H), 5.32(2H,s,COOCH$_2$), 5.33(1H,d.d,J=5& 9 Hz,C$_3$-H), 7.32(1H,s,thiazole-5-H), 7.3–7.7(2H,m,CONH$_2$), 7.67(2H,d,J=9 Hz,aromatic proton), 8.19(2H,d,J=9Hz,aromatic proton), 9.35(1H,d,J=9 Hz,C$_3$-NH), 12.90(1H,br.s,thiazole-2-NH).

(b) In a mixed solution of 9 ml of tetrahydrofuran and 3 ml of water is suspended 270 mg of the product as obtained under the above (a), and 78 mg of sodium N-methyldithiocarbamate is added to the suspension, followed by stirring at room temperature for 50 minutes. 39 mg of sodium N-methyldithiocarbamate is furthermore added, followed by stirring for another 30 minutes. Ethyl acetate and water are added to the reaction solution, and after the mixture is shaken, the organic layer is separated, washed with aqueous sodium chloride solution, dried over anhydrous magnesium sulfate and concentrated under reduced pressure. Ether is added to the residual solid, and filtration is effected to give 195 mg (83.2%) of (3S,4S)-3[2-(2-aminothiazol 4-yl)-(Z)-2-methoxyiminoacetamido]-4-carbamoyl-1-(p-nitrobenzyloxycarbonylmethoxy)-2-azetidinone as yellow crystals, m.p. 183°–186° C. (decomp.).

IR (KBr) cm$^{-1}$: 1,785, 1,750, 1,675, 1,520, 1,350.

NMR (d$_6$-DMSO)67: 3.80(3H,s,OCH$_3$), 4.73(1H,d,J=5 Hz,C$_4$-H), 4.77(2H,br.s,OCH$_2$COO), 5.29(1H,d,J=5&9 Hz,C$_3$-H), 5.30(2H,s,COOCH$_2$), 6.67(1H,s,thiazole-5-H), 7.10(2H,br.s,thiazole-2-NH$_2$), 7.67(2H,d,J=9 Hz,aromatic proton), 8.19(2H,d,J=9 Hz,aromatic proton), 9.22(1H,d,J=9 Hz,C$_3$-NH).

(c) In a mixed solution of 10 ml of tetrahydrofuran and 10 ml of water is suspended 140 mg of the product as obtained under the above (b), and 140 mg of 10% palladium-charcoal is added to the suspension, followed by stirring under a hydrogen atmosphere at room temperature for 1 hour. 22 mg of sodium hydrogen carbonate is added to the reaction solution, which is stirred under a hydrogen atmosphere for further 1 hour. The catalyst is filtered off and washed with a mixed solution (1:1) of tetrahydrofuran and water. The filtrate and washing are combined and concentrated under reduced pressure to distill off the tetrahydrofuran. The residual aqueous solution is washed with ethyl acetate and concentrated under reduced pressure. The residue is purified by column chromatography (Amberlite XAD-2, 100 ml; water) and lyophilized to give 68 mg (55.1%) of the above-identified compound as a colorless poweder.

IR (KBr) cm$^{-1}$: 1,780, 1,680, 1,620, 1,530,

NMR (d$_6$-DMSO)δ: 3.80(3H,s,OCH$_3$), 4.16(2H,ABq,J=15 Hz, OCH$_2$COO), 4.66(1H,d,J=6 Hz,C$_4$-H), 5.20(1H,d.d,J=6&9 Hz, C$_3$-H), 6.80(1H,s,thiazole-5-H), 9.18(1H,d,J=9 Hz,C$_3$-NH).

Elemental analysis, for C$_{12}$H$_{13}$N$_6$NaO$_7$S.2.8H$_2$O

|  | C (%) | H (%) | N (%) |
| --- | --- | --- | --- |
| Calcd. | 31.41 | 4.09 | 18.32 |
| Found | 31.31 | 4.15 | 18.58 |
| $[\alpha]_D^{25}$ −30.3° (c = 0.5, water). | | | |

EXAMPLE 9

Synthesis of (3S,4S)-3-[2-(2-aminothazol-4-yl)-(Z)-2-carboxymethoxyiminoacetamido]-4-carbamoyl-1-carboxymethoxy-2-azetidinone disodium salt.

(a) In 20 ml of dichloromethane is suspended 550 mg of (3S,4S)-3-(tert-butoxycarbonylamino)-4-carbamoyl-1-(p-nitrobenzyloxycarbonylmethoxy)-2-azetidinone, and 2 ml of anisole and 10 mL of trifluoroacetic acid are added to the suspension under ice-cooling with stirring. After the stirring under ice-cooling for 2 hours, 20 ml of toluene is added to the reaction solution, and the mixture is concentreated under reduced pressure. 20 ml of dichloromethane is added to the residue, and 1.06 ml of triethylamine and 964 mg of 2-(2-chloroacetamidothiazol-4-yl)-(Z)- 2-(p-nitrobenzyloxycarbonylmethoxyimino)acetyl chloride hydrochloride (prepared by the method as described in the Japanese Unexamined Patent Publication No. 131758/1982) are added, followed by stirring under ice-cooling for 2 hours. The solvent is distilled off under reduced pressure, and 15 ml of tetrahydrofuran and 15 ml of water are added to the residue. The mixture is adjusted to pH 7 with aqueous sodium hydrogen carbonate solution, and stirred under ice-cooling for 1 hour. The tetrahydrofuran is distilled off under reduced pressure, and crystals which separate out are recovered by filtration, and washed with aqueous sodium hydrogen carbonate solution, water, ether, ethyl acetate andeether successively to give 848 mg (83.0%) of (3S,4S)-4-carbamoyl-3-[2-(2-chloroacetamidothiazol-4-yl)-(Z)-2-(p-nitrobenzyloxycarbonylmethoxyimino)acetamido]-1-(p-nitrobenzyloxycarbonylmethoxy)-2-azetidinone as yellow crystals, which is shown by TLC to contain a slight amount of impurities but used as crude crystals in the substituent reaction, m.p. 147°–153° C.

IR (KBr) cm$^{-1}$: 1,790, 1,740, 1,675, 1,520, 1,350.

NMR (d$_6$-DMSO)δ: 4.33(2H,s,ClCH$_2$), 4.65–4.95(5H,m,2×OCH$_2$COO& C$_4$-H), 5.2–5.5(5H,m,2×COOCH$_2$&C$_3$-H), 7.83(1H,s,thiazole-5-H), 7.3–7.8(6H,m,CONH$_2$ and aromatic proton), 8.15 (2H,d,J=9 Hz,aromatic proton), 8.22(2H,d,J=9 Hz,aromatic proton), 9.35(1H,d,J=9 Hz,C$_3$-NH).

Elemental analysis, for C$_{29}$H$_{25}$ClN$_8$O$_{14}$S.2H$_2$O

|  | C (%) | H (%) | N (%) |
|---|---|---|---|
| Calcd. | 42.84 | 3.59 | 13.78 |
| Found | 43.08 | 3.74 | 13.55 |

(b) In a mixed solution of 15 ml of tetrahydrofuran and 5 ml of water is suspended 700 mg of the product as obtained under the above (a), and 129 mg of sodium N-methyldithiocarbamate is added to the suspension, followed by stirring at room temperature for 1 hour. 45 ml of tetrahydrofuran, 5 ml of water and 129 mg of sodium N-methyldithiocarbamate are furthermore added to the reaction mixture, followed by stirring for further 30 minutes. The tetrahydrofuran is distilled off under reduced pressure, and after water is added to the residue, the resulting precipitate is recovered by filtration, and washed with water, ether, ethyl acetate and ether successively to give 501 mg (80%) of (3S,4S)-3-[2-(2-aminothiazol 4-yl)-(Z)-2-(p-nitrobenzyloxycarbonyl-methoxyimino) acetamido]-4-carbamoyl-1(p-nitrobenzyloxycarbonylmethoxy)-2-azetidinone as a yellow solid, m.p. 187°–190° C. (decomp.).

IR (KBr) cm$^{-1}$: 3,430, 3,260, 1,785, 1,750, 1,680, 1,520, 1,350.

NMR (d$_6$-DMSO)δ: 4.6–4.85(5H,m,2×OCH$_2$COO&C$_4$-H), 5.15–5.50 (5H,m,2×COOCH$_2$&C$_3$-H), 6.76(1H,s,thiazole-5-H), 7.17(2H, br.s,thiazole-2-NH$_2$), 7.25–7.75(6H,m,CONH$_2$ and aromatic proton), 8.18(2H,d,J=9 Hz,aromatic proton), 8.22(2H,d, J=9 Hz,aromatic proton), 9.15(1H,d,J=9 Hz,C$_3$-NH).

Elemental analysis, for C$_{27}$H$_{24}$N$_8$O$_{13}$S.1.5H$_2$O

|  | C (%) | H (%) | N (%) |
|---|---|---|---|
| Calcd. | 44.57 | 3.74 | 15.40 |
| Found | 44.54 | 3.52 | 15.14 |

(c) In a mixed solution of 15 ml of tetrahydrofuran and 15 ml of water is suspended 280 mg of the product as obtained under the above (b), and 280 mg of 10% palladium-charcoal added to the suspension, followed by stirring under a hydrogen atmosphere at room temperature for 1 hour. 67 mg of sodium hydrogen carbonate is added to the reaction solution, which is stirred under a hydrogen atmosphere for further 4 hours. The catalyst is filtered off and washed with a mixed solution (1:1) of tetrahydrofuran and water. The filtrate and washing are combined and concentrated under reduced pressure to distill off the tetrahydrofuran. The residual aqueous solution is washed with ethyl acetate and concentrated under reduced pressure, and the residue is purified by column chromatography (Amberlite XAD-2, 200 ml; water) and lyophilized to give 92 mg (44%) of the above-identified compound as a colorless powder.

IR (KBr) cm$^{-1}$: 1,780, 1,680, 1,605(br.), 1,410, 1,030.

NMR (D$_2$O)δ: 4.16(2H,s,OCH$_2$COO), 4.68(2H,s,OCH$_2$CCOO), 5.18 (1H,d,J=5 Hz,C$_4$-H), 5.60(1H,d,J=5 Hz,C$_3$-H), 7.06(1H,s, thiazole-5-H).

Elemental analysis, for C$_{13}$H$_{12}$N$_6$Na$_2$O$_9$S.4H$_2$O

|  | C (%) | H (%) | N (%) |
|---|---|---|---|
| Calcd. | 28.57 | 3.69 | 15.38 |
| Found | 28.65 | 3.41 | 15.16 |

[α]$_D^{25}$ −23.5° (c = 0.55, water)

EXAMPLE 10

Synthesis of (3S)-3-(tert-butoxycarbonylamino)-1-[1-(p-nitrobenzyloxycarbonyl-1-methylethoxy]-2-azetidinone.

In 50 ml of acetonitrile is dissolved 1.01 g of (3S)-3-(tert-butoxycarbonylamino-1-hydroxy-2-azetidinone, and 0.84 ml of triethylamine and 1.81 g of p-nitrobenzyl 2-bromo-2-methylpropionate are added to the solution under ice-cooling with stirring. After the stirring at room temperature for 1.5 hours and then at 3° to 5° C. for 60 hours, hhe reaction solution is concentrated under reduced pressure. The residue is dissolved in ethyl acetate, and the solution is washed with water and dried over anhydrous magnesium sulfate. The solvent is distilled off under reduced pressure, and the residue is purified by column chromatography (silica gel, 130 g; ethyl acetate-n-hexane=1:1) to give 0.822 g (38.8%) of the above-identified compound as a colorless gum-like product.

IR (KBr) cm$^{-1}$: 3,410, 1,790, 1,720, 1,530, 1,350, 1,170.

NMR (d$_6$-DMSO)δ: 1.37(9H,s,3×CH$_3$), 1.47(3H,s,CH$_3$), 1.51 (3H,s,CH$_3$), 3.36(1H,d.d,J=3&5 Hz,C$_4$-H), 3.70(1H,t,J=5 Hz, C$_4$-H), 4.35–4.65(1H,m,C$_3$-H), 5.31(2H,s,COOCH$_2$), 7.52 (1H,d,J=9 Hz,C$_3$-NH), 7.66(2H,d,J=9 Hz, aromatic proton), 8.23(2H,d,J=9 Hz, aromatic proton).

EXAMPLE 11

Synthesis of (3S-3-(tert-butoxycarbonylamino)-1-(p-nitrobenzyloxycarbonylmethoxy)-2-azetidinone.

In 800 ml of acetone is dissolved 3.93 g of N-(tert-butoxycarbonyl)-O-methanesulfonyl-L-serine-N'-(p-nitrobenzyloxycarbonyl)amide, and 3.31 g of potassium carbonate is added to the solution. The temperature of the reaction solution is gradually elevated under a nitrogen atmosphere until it reaches 60° C. over a period of 20 minutes, and the reaction solution is stirred at the same temperature for 55 minutes. The reaction solution is filtered, and the filtrate is concentrated under reduced pressure. The residue is dissolved in a mixed solution of 200 ml of ethyl acetate and 50 ml of tetrahydrofuran, and the solution is washed with dilute hydrochloric acid, aqueous sodium chloride solution, aqueous sodium hydrogen carbonate solution and aqueous sodium chloride solution successively and dired over anhydrous magnesium sulfate. The solvent is ditilled off under reduced pressure, and after ether is added to the residue, the resulting solid is recovered by filtration to give 2.37 g (75.0%) of the above-identified compound as colorless crystals, m.p. 144°–145° C.

IR (KBr) cm$^{-1}$: 3,360, 1,790, 1,680, 1,520, 1,350

NMR (d$_6$-DMSO)δ: 1.37(9H,s,3×CH$_3$), 3.43(1H,d.d,J=3&4.5 Hz, C$_4$-H), 3.78(1H,t,J=4.5 Hz,C$_4$-H), 4.3–4.6(1H,m,C$_3$-H), 4.69(2H,s,OCH$_2$COO), 5.33(2H,s,COOCH$_2$), 7.45(1H,d,J=9 Hz, C$_3$-NH), 7.65(2H,d,J=9 Hz,aromatic proton), 8.22(2H,d, J=9 Hz,aromatic proton).

Elemental analysis, for C$_{17}$H$_{21}$N$_3$O$_8$

|  | C (%) | H (%) | N (%) |
|---|---|---|---|
| Calcd. | 51.64 | 5.35 | 10.63 |
| Found | 51.82 | 5.18 | 10.58 |

$[\alpha]_D^{24} -14.0°$ (c = 1, MeOH)

EXAMPLE 12

Using N-(tert-butoxycarbonyl)-O-methanesulfonyl-L-allothreonine-N'-(p-nitrobenzyloxycarbonylmethoxy)amide in place of N-(tert-butoxycarbonyl)-O-methanesulfonyl-L-threonine-N'-(p-nitrobenzyoxycarbonylmethoxy)amide, the reaction is carried out in the same manner as Example 1 to give (3S,4R)-3-(tert-butoxycarbonylamino-4-methyl-1-(p-nitrobenzyloxycarbonylmethoxy)-2-azetidinone, in the yield of 75.2%, m.p. 156°–158° C.

IR (KBr) cm$^{-1}$: 3,340, 1,785, 1,765, 1,690, 1,525, 1,350, 1,210.

NMR (d$_6$-DMSO)δ: 1.12(3H,d,J=6 Hz,C$_4$-CH$_3$), 1.37(9H,s,3×CH$_3$), 3.95–4.3(1H,m,C$_4$-H), 4.65(1H,d,J=5&9 Hz,C$_3$-H), 4.68 (2H,s,OCH$_2$COO), 5.34(2H,s,COOCH$_2$), 7.54(1H,d,J=9 Hz, C$_3$-NH), 7.66(2H,d,J=9 Hz,aromatic proton), 8.22(2H,d, J=9 Hz,aromatic proton).

$[\alpha]_D^{25} +53.3°$(c=0.4,MeOH)

EXAMPLE 13

Synthesis of (3S)-3-[2-(2-aminothiazol-4-yl)-(Z)-2-(1-carboxyl-1-methylethoxyimino)acetamido]-1-(1-carboxy-1-methylethoxy)-2-azetidinone disodium salt.

(a) By subjecting 1.30 g of (3S)-3-(tert-butoxycarbonylamino)-1-[1-methyl-1-(p-nitrobenzyloxycarbonyl)ethoxy]-2-azetidinone obtained in Example 10 to the same reaction as Example 5 b), there is obtained 1.45 g (59.6%) of (3S)-3-{2-(2-chloroacetamidothiazol-4-yl)-(Z)-2-[1-methyl-1-(p-nitrobenzyloxycarbonyl)ethoxyimino]acetamido}-1-[1-methyl-1-(p-nitrobenzyloxycarbonyl)ethoxy]-2-azetidinone as a colorless foamy product.

IR(KBr) cm$^{-1}$: 3,330(br.), 1,790, 1,750, 1,690, 1,525, 1,350, 1,150.

NMR (d$_6$-DMSO)δ: 1.3–1.7(12H,m,4×CH$_3$), 3.4–3.6(1H,m,C$_4$-H), 3.75–3.95(1H,m,C$_4$-H), 4.33(2H,s,ClCH$_2$), 4.75–5.05 (1H,m,C$_3$-H), 5.30(4H,s,2xCOOCH$_2$), 7.36(1H,s,thiazole-5-H), 7.58(2H,d,J=9 Hz, aromtic proton), 7.63(2H,d,J=9 Hz, aromatic proton), 8.05(2H,d,J=9 Hz,aromatic proton), 8.20(2H,d,J=9 Hz, aromatic proton), 9.80(1H,d,J=9 Hz, C$_3$-NH), 12.87(1H,br.s,thiazole-22-NH).

(b) By subjecting 1.23 g of the product as obtained under the above (a) to the same reaction as Example 5 (c), there is obtained 0.913 g (82.0%) of (3S)-3-{2-(2-aminothiazol-4-yl)-(Z)-2-[1-methyl-1-(p-nitrobenzyloxycarbonyl)ethoxyimino]-acetamido}-1-[1-methyl-1-(p-nitrobenzyloxycarbonyl)ethoxy]-2-azetidinone as a yellow foamy product.

IR (KBr) cm$^{-1}$: 3,380(br.), 1,785, 1,740, 1,680, 1,535, 1,250.

NMR (d$_6$-DMSO)δ: 1.35–1.65(12H,m,4×CH$_3$), 3.3–3.6(1H,m,C$_4$-H), 3.73(1H,t,J=5 Hz,C$_4$-H), 4.75–5.05(1H,m,C$_3$-H), 5.32(4H, s,2xCOOCH$_2$), 6.70(1H,s,thiazole-5-H), 7.27(2H,br.s, thiazole-2-NH$_2$), 7.62(2H,d,J=9 Hz,aromatic proton), 7.65 (2H,d,J=9 Hz,aromtic proton), 8.12(2H,d,J=9 Hz,aromatic proton), 8.22(2H,d,J=9 Hz, aromatic proton), 9.06(1H,d,J=8 Hz,C$_3$-NH).

(c) By subjecting 460 mg of the product as obtained under the above (b) to the same reaction as Example 5 (d), there is 244 mg of the above-identified compound as a yellowish powder.

IR (KBr) cm$^{-1}$: 1,770, 1,660(sh), 1,595(br.), 1,530, 1,410, 1,370.

NMR (d$_6$-DMSO)δ: 1.25(3H,s,CH$_3$), 1.34(3H,s,CH$_3$), 1.40(3H, s,CH$_3$), 1.45(3H,s,CH$_3$), 3.5–3.7(1H,m,C$_4$-H), 3.7–3.95 (1H,m,C$_4$-H), 4.75–5.05(1H,m,C$_3$-H), 6.76(1H,s,thiazole-5-H), 7.14(2H,br.s,thiazole-2-NH$_2$), 11.47(1H,d,J=9 Hz, C$_3$-NH).

EXAMPLE 14

Synthesis of (3S,4S)-3-(tert-butoxycarbonylamino)-4-carbamoyloxymethyl-1-(p-nitrobenzyloxycarbonylmethoxy)-2-azetidinone.

In 40 ml of acetonitrile is dissolved 650 mg of (3S,4S)3-(tert-butoxycarbonylamino)-4-carbamoyloxymethyl-1-hydroxy-2-azetidinone, and 0.39 ml of triethylamine and 712 mg of p-nitrobenzyl bromoacetate are added to the solution under ice-cooling with stirring. The reaction solution is stirred at room temperature (15°–25° C.) for 3.5 hours. The solvent is distilled off under reduced pressure, and 50 ml of a mixed solution (1:1) of ethyl acetate and tetrahydrofuran and 50 ml of water are added to the residue. The organic layer is separated, washed with aqueous sodium chloride solution, dried over anhydrous magnesium sulfate and concentrated under reduced pressure. The remaining crystals are treated with 15 ml of a mixed solution (1:2) of ether and hexane and filtered to give 98 mg (88.6%) of the above-identified comoound as crystals, m.p. 189°–191° C.

TR(KBr) cm$^{-1}$: 3,440, 1,790, 1,700, 1,525, 1,350.

NMR (CDCl$_3$+d$_6$-DMSO)δ: 1.44(9H,s,3×CH$_3$), 3.85–4.15(2H,m, C$_4$-CH$_2$), 4.15–4.38(1H,m,C$_4$-H), 4.65(2H,s,OCH$_2$COO), 4.92 (1H,d.d,J=5&10 Hz,C$_3$-H), 5.33(2H,s,COOCH$_2$), 5.92–6.18 (2H,br,CONH$_2$), 6.88(1H,d,J=10 Hz,C$_3$-NH), 7.63(2H,d,J=9 Hz, aromatic proton), 8.27(2H,d,J=9 Hz,aromatic proton).

EXAMPLE 15

Synthesis of (3S,4S)-3-[2-(2-aminothiazol-4-yl)-(Z)-2-carboxymethoxyiminoacetamido]-4-carbamoyloxymethyl-1-carboxymethoxy-2-azetidinone disodium salt.

(a) In 20 ml of dichloromethane is suspended 436 mg of (3S,4S)-3-(tert-butoxycarbonylamino)-4-carbamoyloxymethyl-1-(p-nitrobenzyloxycarbonylmethoxy)-2-azetidinone, and 2 ml of anisole and 10 ml of trifluoroacetic acid are added to the suspension under ice-cooling with stirring. After the stirring under ice-cooling for 1.5 hours, 20 ml of toluene is added to the reaction solution, and the mixture is concentrated under reduced pressure. The residue is suspended in 25 ml of dichloromethane, and 0.84 ml of triethylamine and 614 mg of 2-(2-chloroacetamidothiazol-4-yl)-(Z)-2-(p-nitrobenzyloxycarbonylmethoxyimino)acetyl chloride hydrochloride are added to the suspension under ice-cooling, followed by stirring for 2 hours. The solvent is distilled off under reduced pressure, and the residue is dissolved in 200 ml of a mixed solution (3:1) of ethyl acetate and tetrahydrofuran, and the solution is washed with 3N hydrochloric acid, aqueous sodium hydrogen carbonate solution and aqueous sodium chloride solution successively and dried over anhydrous magnesium sulfate. The solvent is distilled off under reduced pressure, and the residue is purified by column chromatography (silica gel, 210 g; a mixed solution (1:1) of chloroform and ethyl acetate, then a fixed solution (8:8:1) of chloroform, ethyl acetate and methanol) to give 660 mg (81.8%) of (3S,4S)-4-carbamoyloxymethyl-3-[2-(2-chloroacetamidothiazol-4-yl)-(Z)-2-(p-nitrobenzyloxycarbonylmethoxyimino)acetamido]-1-(p-nitrobenzyloxycarbonylmethoxy)-2-azetidinone as a foamy product.

IR (KBr) cm$^{-1}$: 3,380, 1,760, 1,690, 1,520, 1,350.

NMR (d$_6$-DMSO)δ: 3.95–4.50(3H,m,C$_4$-H&C$_4$-CH$_2$), 4.34[2H,s, ClCH$_2$CO), 4.70(2H,s,OCH$_2$COO), 4.85(2H,s,OCH$_2$COO), 5.27 (1H,d.d,J=5&10 Hz, C$_3$-H), 5.33(2H,s, COOCH$_2$), 6,52–6.70 (2H,br.,CONH$_2$), 7.50(1H,s,thiazole-5-H), 7.60–7.78(4H,m, aromatic proton), 8.14–8.33(4H,-m,aromatic proton), 9.30 (1H,d,J=10 Hz,C$_3$-NH), 12.74–12.87(1H,br,thiazole-2-NH).

$[\alpha]_D^{23}$ +14.2° (c=0.19,DMSO)

(b) In a mixed solution of 8 ml of tetrahydrofuran and 3 ml of water is dissolved 640 mg of the product as obtained under the above (a), and 102 mg of sodium N-methyldithiocarbamate is added to the solution, followed by stirring for 45 minutes. 102 mg of sodium N-methyldithiocarbamate is furthermore added, followed by stirring for further 60 minutes. Ethyl acetate is added to the reaction solution, and after the shaking, the organic layer is separated, washed with aqueous sodium chloride solution, dried over anhydrous magnesium sulfate and concentrated under reduced pressure. The remaining solid is treated with 10 ml of a mixed solution (1:1) of ethyl acetate and tetrahydrofuran, and filtered to give 300 mg (51.8%) of (3S,4S)-3-[2-(2-aminothiazol-4-yl)-(Z)-2-(p-nitrobenzyloxycarbonylmethoxyimino)acetamido)-4-carbamoyloxymethyl-1-(p-nitrobenzyloxycarbonylmethoxy)-2-azetidinone as a reddish powder. The mother liquor is concentrated under reduced pressure, and the residue is purified by column chromatography (silica gel, 300 g; a mixed solution (1:1) of ethyl acetate and chloroform, then a mixed solution (5:5:1) of ethyl acetate, chloroform and methanol) to yield furthermore 100 mg [17.3%] of the above compound, m.p. 149°–152° C. (decomp.)

IR (KBr) cm$^{-1}$: 3,420, 1,780, 1,745, 1,690, 1,610, 1,520, 1,355.

NMR (d$_6$-DMSO)δ: 3.94–4.51(3H,m,C$_4$-CH$_2$&C$_4$-H), 4.72(2H,s, OCH$_2$COO), 4.80(2H,s,OCH$_2$COO), 5.25(1H,d.d,J=5&9 Hz,C$_3$-H), 5.33(4H,s,2×COOCH$_2$), 6.45–6.66(2H,br.s,CONH$_2$)], 6.80 (1H,s,thiazole-5-H), 7.08–7.28(2H,br.s,thiazole-2-NH$_2$), 7.58–7.79(4H,m,aromatic proton), 8.10–8.37(4H,-m,aromatic proton), 9.15(1H,d,J=9 Hz,C$_3$-NH). $[\alpha]_D^{23}$ +17.7° (c=0.22,DMSO).

(c) In a mixed solution of 10 ml of tetrahydrofuran and 10 ml of water is dissovled 380 mg of the product as obtained under the above b), and 380 mg of 10% palladium-charcoal is added to the solution, followed by stirring under a hydrogen atmosphere at room temperature (15° to 25° C.) for 6 hours. The catalyst is filtered off, and 87 mg of sodium hydrogen carbonate is added to the filtrate, and the mixture is concentrated under reduced pressure to distill off the tetrahydrofuran. The remaining aqueous solution is washed with ethyl acetate and concentrated under reduced pressure. The residue is puriiied by column chromatography (Amberlite XAD-2, 220 ml; water), and lyophilized to give 130 mg (49.6%) of the above-identified compound as a powder.

IR (KBr) cm$^{-1}$: 3,400, 1,775, 1,720, 1,610, 1,535, 1,410, 1,320, 1,040.

NMR (D$_2$O)δ: 4.25–4.70(3H,m,C$_4$-CH$_2$&C$_4$-H), 4.65(2H,s,OCH$_2$COO), 4.75(2H,s,OCH$_2$COO), 5.50(1H,d,J=5 Hz,C$_3$-H), 7.21(1H,s, thiazole-5-H).

Elemental analysis, for C$_{14}$H$_{14}$N$_6$Na$_2$O$_{10}$S.2H$_2$O

|  | C (%) | H (%) | N (%) |
| --- | --- | --- | --- |
| Calcd. | 31.12 | 3.36 | 15.55 |
| Found | 30.87 | 3.49 | 15.62 |
| $[\alpha]_D^{23}$ +18.8° (c = 0.26, H$_2$O) | | | |

EXAMPLE 16

Synthesis of trans-3-(tert-butoxycarbonylamino)-4-carbamoyloxymethyl-1-(p-nitrobenzyloxycarbonylmethoxy)-2-azetidinone.

In 45 ml of acetonitrile is dissolved 1.227 g of trans-3-(tert-butoxycarbonylamino)-4-carbamoyloxymethyl-1-hydroxy-2-azetidinone, and 0.75 ml of triethylamine and 1.34 g of p-nitrobenzyl bromoacetate are added to the solution under ice-cooling with stirring. The reaction solution is stirred at room temperature (15° to 25° C.) for 1 hour. The solvent is distilled off under reduced pressure, and ethyl acetate and water are added to the residue, followed by shaking. The ethyl acetate layer is separated, washed with aqueous sodium chloride solution, dried over anhydrous magnesium sulfate and concentrated under reduced pressure. The residue is purified by column chromatography (silica gel, 100 g; a mixed solution (2:1) of ethyl acetate and n-hexane) to give 1.735 g(83%) of the above-identified compound as a colorless foamy product.

IR (KBr) cm$^{-1}$: 3,370, 1,785, 1,710, 1,605, 1,520, 1,350.

NMR (d$_6$-DMSO)δ: 1.38(9H,s,3×CH$_3$), 3.95–4.40(4H,m,C$_3$-H,C$_4$-H, C$_4$-CH$_2$),4.71(2H,s,OCH$_2$COO), 5.33(2H,s,COOCH$_2$), 6.59(2H, br.s,OCONH$_2$), 7.50(1H,d,J=8 Hz,C$_3$-NH), 7.67(2H,d,J=9 Hz, aromatic proton), 8.22(2H,d,J=9 Hz,aromatic proton).

EXAMPLE 17

Synthesis of trans-3-[2-(2-aminothiazol-4-yl)-(Z)-2-carboxymethoxyiminoacetamido]-4-carbamoyloxymethyl-1-carboxymethoxy-2-azetidinone disodium salt.

(a) By subjecting 843 mg of trans-3-(tert-butoxycarbonylamino)-4-carbamoyloxymethyl-1-(p-nitrobenzyloxycarbonylmethoxy)-2-azetidinone to the same reaction as Example 15 (a), there is obtained 819 mg (56.4%) of trans-4-carbamoyloxymethyl-3-[2-(2-chloroacetamidothiazol-4-yl)-(Z)-2-(p-nitrobenzyloxycarbonylmethoxyimino)acetamido]-1-(p-nitrobenzyloxycarbonylmethoxy)-2-azetidinone as a colorless foamy product.

IR (KBr) cm$^{-1}$: 3,370, 1,785, 1,760–1,730(br.), 1,690, 1,520, 1,350.

NMR (d$_6$-DMSO)δ: 4.1–4.4(3H,m,C$_4$-H&C$_4$-CH$_2$), 4.33(2H,s, ClCH$_2$CO), 4.55–4.75(1H,m,C$_3$-H), 4.75(2H,s,OCH$_2$COO), 4.85(2H,s,OCH$_2$COO), 5.34(4H,s,2xCOOCH$_2$), 6.62[2H,br.s, OCHNH$_2$), 7.43(1H,s,thiazole-5-H), 7.64(4H,d,J=9 Hz, aromatic proton), 8.16(2H,d,J=9 Hz,aromatic proton), 8.18(2H,d,J=9 Hz,aromatic proton), 9.33(1H,d,J=8 Hz, C$_3$-NH), 12.85(1H,br.s,thiazole-2-NH).

(b) By subjecting 742 mg of the above product to the same reaction as Example 15 (b), there is obtained 565 mg (84.2%) of trans-3-[2-(2-aminothiazol-4-yl)-(Z)-2-(p- nitrobenzyloxy-carbonylmethoxyimino)acetamido]-4-carbamoyloxymethyl-1-(p-nitrobenzyloxycarbonylmethoxy)-2-azetidinone as a yellow powder.

IR (KBr) cm$^{-1}$: 3,400(br.), 1,785, 1,730, 1,675, 1,605, 1,520, 1,350.

NMR [d$_6$-DMSO]$\delta$: 4.1–4.4(3H,m,C$_4$-H&C$_4$-CH$_2$), 4.57(1H,d.d,J=1.5&8 Hz,C$_3$-H), 4.76(2H,s,OCH$_2$COO), 4.81(2H,s,OCH$_2$COO), 5.33(4H,s,2xCOOCH$_2$), 6.61(2H,br.s,OCONH$_2$), 6.77(1H, s,thiazole-5-H), 7.21(2H,br.s,thiazole-NH$_2$), 7.65(4H,d, J=9 Hz,aromatic proton), 8.17(2H,d,J=9 Hz,aromatic proton), 8.19(2H,d,J=9 Hz,aromatic proton), 9.19(1H,d,J=8 Hz,C$_3$-NH).

(c) By subjecting 600 mg of the product as obtained under the above (b) to the same reaction as Example 15 (c), there is obtained 213 mg (48%) of the above identified compound as a colorless powder.

IR (KBr) cm$^{-1}$: 1,775, 1,720, 1603(br.), 1,530, 1,410, 1,320.

NMR (d$_6$-DMSO)$\delta$: 4.0–4.55(7H,m,C$_4$-H,C$_4$-CH$_2$,2xOCH$_2$COO), 4.72 (1H,br.d,J=8 Hz,C$_3$-H), 6.58(2H,br.s,OCONH$_2$), 6.78(1H, s,thiazole-5-H), 7.16(2H,br.s,thiazole-NH$_2$), 11.41 (1H,d,J=8 Hz,C$_3$-NH).

Elemental analysis, for C$_{14}$H$_{14}$N$_6$Na$_2$O$_{10}$S.2H$_2$O

|  | C (%) | H (%) | N (%) |
|---|---|---|---|
| Calcd. | 31.12 | 3.36 | 15.55 |
| Found | 31.05 | 3.64 | 15.37 |

EXAMPLE 18

Synthesis of trans-3-[2-(2-aminothiazol-4-yl)-(Z)-2-(1-carboxy-1-methylethoxyimino)acetamido]-4-carbamoyloxymethyl-1-carboxymethoxy-2-azetidinone disodium salt.

(a) By subjecting 800 mg of trans-3-(tert-butoxycarbonylamino)-4-carbamoyloxymethyl-1-(p-nitrobenzyloxycarbonylmethoxy)-2-azetidinone obtained in Example 16 to the same reaction as Example 3 (a), there is obtained 1.240 g (70.1%) of trans-4-carbamoyloxymethyl-3-{2-(2-chloroacetamidothiazol-4-yl)-(Z)-1-methyl-1-(p-nitrobenzyloxycarbonyl)ethoxyimino]acetamido}-1-(p-nitrobenzyloxycarbonylmethoxy)-2-azetidinone as a colorless powder.

IR (KBr) cm$^{-1}$: 3,370(br.), 1,785, 1,735, 1,690, 1,520, 1,350.

NMR (d$_6$-DMSO)$\delta$: 1.51(6H,s,2×CH$_3$), 4.1–4.5(3H,m,C$_4$-H&C$_4$-CH$_2$), 4.34(2H,s,ClCH$_2$CO), 4.6–4.9(3H,m,C$_3$-H&OCH$_2$COO), 5.33 (4H,s,COOCH$_2$), 6.62(2H,br.,OCONH$_2$), 7.59(1H,s,thiazole-5-H), 7.59(2H,d,J=9 Hz,aromatic proton), 7.66(2H,d,J=9 Hz, aromatic proton), 8.07(2H,d,J=9 Hz,aromatic proton), 8.19(2H,d,J=9 Hz,aromatic proton), 9.20(2H,d,J=7.5 Hz, C$_3$-NH), 12.87(1H,br. s,thiazole-2-NH).

(b) By subjecting 994 mg of the product as obtained under the above (a) to the same reaction as Example 3 (b), there is obtained 817 mg (90.5%) of trans-3-{2-(2-aminothiazol- 4-yl)-(Z)-2-[1-methyl-1-(p-nitrobenzyloxycarbonyl)ethoxyimino]acetamido}-carbamoyloxymethyl-1-(p-nitrobenzyloxycarbonylmethoxy)-2-azetidinone as a yellow foamy product.

IR (KBr) cm$^{-1}$: 3,370, 1,790, 1,735, 1,680, 1,605 1,520.

NMR (d$_6$-DMSO)$\delta$: 1.48(6H,s,2×CH$_3$), 4.10–4.45(3H,m,C$_4$-H&C$_4$-CH$_2$), 4.63(1H,d.d,J=1.5&7.5 Hz,C$_3$-H), 4,76(2H,s, OCH$_2$COO), 5.33(4H,s,2xCOOCH$_2$), 6.62(2H,br.,s,OCONH$_2$), 6.73(1H,s,thiazole-5-H), 7.27(2H,br.s,thiazole-2-NH$_2$), 7.62(2H,d,J=9 Hz,aromatic proton), 7.65(2H,d,J=9 Hz, aromatic proton), 8.12(2H,d,J=9 Hz,aromatic proton), 8.19(2H,d,J=9 Hz,aromatic proton), 9.07(1H,d,J=7.5 Hz, C$_3$-NH).

(c) By subjecting 668 mg of the product as obtained under the above (b) to the same reaction as Example 3 (c), there is obtained 248 mg (49.6%) of the above-identified compound as a colorless powder.

IR (KBr) cm$^{-1}$: 1,780, 1,735, 1,610(br.), 1,535, 1,410.

NMR (d$_6$-DMSO)$\delta$: 1.40(6H,s,2×CH$_3$), 4.07(2H,br.s,OCH$_2$COO), 4.15–4.55(3H,m,C$_4$-H&C$_4$-CH$_2$), 4.71(2H,br.d,J=8 Hz,C$_3$-H), 6.57 (2H,br.s,OCONH$_2$), 6.73(1H,s,thiazole-5-H),7.10 (2H,br.s,thiazole-2-NH$_2$), 11.45(1H,d,J=8 Hz,C$_3$-NH).

Elemental analysis, for C$_{16}$H$_{18}$N$_6$Na$_2$O$_{10}$S.2H$_2$O

|  | C (%) | H (%) | N (%) |
|---|---|---|---|
| Calcd. | 33.81 | 3.90 | 14.78 |
| Found | 33.76 | 4.10 | 14.86 |

EXAMPLE 19

Synthesis of (3S,4S)-3-[2-(2-aminothiazol-4-yl)-(Z)-2-carboxymethoxy-iminoacetamido]-1-carboxymethoxy-4-methyl-2-azetidinone disodium salt.

(a) By subjecting 1.228 g of (3S,4S)-3-(tert-butoxycarbonylamino)-4-methyl-1-(p-nitrobenzyloxycarbonylmethoxy)-2-azetidinone to the same reaction as Example 15 (a), there is obtained 1.441 g (64.2%) of (3S,4S)-3-[2-(2-chloroacetamidothiazol-4-yl)-(Z)-2-(p-nitrobenzyloxycarbonylmethoxyimino)acetamido]-4-methyl-1-(p-nitrobenzyloxycarbonylmethoxy)-2-azetidinone as a colorless foamy product.

IR (KBr) cm$^{-1}$: 3,380(br.), 1,765, 1,680, 1,520, 1,350.

NMR (d$_6$-DMSO)$\delta$: 1.40(3H,d,J=6 Hz,CH$_3$), 3.85–4.15(1H,m,C$_4$-H), 4.33(2H,s,ClCH$_2$CO), 4.3–4.5(1H,m,C$_3$-H), 4.74(2H,ABq, J=15 Hz,OCH$_2$COO), 4.85(1H,s,OCH$_2$COO), 5.33(4H,s,2xCOOCH$_2$), 7.42(1H,s,thiazole-5-H), 7.63(4H,d,J=9 Hz,aromatic proton), 8.15(2H,d,J=9 Hz,aromatic proton),8.17(2H,d, J=9 Hz,aromatic proton), 9.32(1H,d,J=8 Hz,C$_3$-NH), 12.88 (1H,br.s,thiazole-2-NH).

(b) By subjecting 1.06 g of the product as obtained under the above (a) to the same reaction as Example 15 (b), there is obtained 808 mg (84.9%) of 3S,4S)-(3-[2-(2-aminothiazol-4-yl)-(Z)-2-(p-nitrobenzyloxycarbonylmethoxyimino)acetamido]-4-methyl-1-(p-nitrobenzyloxycarbonylmethoxy)-2-azetidinone as a yellow foamy product.

IR (KBr) cm$^{-1}$: 3,330, 1,770, 1,680, 1,610, 1,520, 1,350.

NMR (d$_6$-DMSO)$\delta$: 1.38(3H,d,J=6 Hz,CH$_3$), 3.8–4.1(1H,m,C$_4$-H), 4.36(1H,d.d,J=1.5&7.5 Hz,C$_3$-H), 4.75(2H,ABq,J=15 Hz, OCH$_2$COO), 4.81(2H,s,OCH$_2$COO), 5.33(4H,s,2xCOOCH$_2$), 6.75(1H,s,thiazole-5-H), 7.22(2H,br.s,thiazole-2-NH$_2$), 7.64(4H,d,J=9 Hz, aromatic proton), 8.18(2H,d,J=9 Hz, aromatic proton), 8.20(2H,d,J=9 Hz,aromatic proton), 9.19(1H,d,J=7.5 Hz,C$_3$-NH).

(c) By subjecting 550 mg of the product as obtained under the above (b) to the same reaction as Example 15 c), there is obtained 270 mg (68.5%) of the above-identified compound as a colorless powder.

IR (KBr) cm$^{-1}$: 1,770, 1,670(sh), 1,615(br.), 1,530, 1,420, 1,320, 1,040.

NMR (d$_6$-DMSO)δ: 1.35(3H,d,J=6 Hz,CH$_3$), 3.8–4.6(6H,m,C$_3$-H, C$_4$-H,2xOCH$_2$COO), 6.80(1H,s,thiazole-5-H), 7.17(2H,br.s, thiazole-2-NH$_2$), 11.34(1H,d,J=9 Hz,C$_3$-NH).

Elemental analysis, for C$_{13}$H$_{13}$N$_5$Na$_2$O$_8$S.2H$_2$O

|  | C (%) | H (%) | N (%) |
|---|---|---|---|
| Calcd. | 32.44 | 3.56 | 14.55 |
| Found | 32.72 | 3.63 | 14.59 |

$[\alpha]_D^{23}$ −43.6° (c = 0.605, water)

EXAMPLE 20

Synthesis of (3S,4S)-3-[2-(2-aminothiazol- 4-yl)-(Z)-(1-methyl-1-pivaloyloxymethoxycarbonylethoxyimino)acetamido]-4-methyl-1-pivaloyloxymethoxycarbonylmethoxy-2-azetidinone.

In 2 ml of N,N-dimethylformamide is dissolved 102 mg of (3S,4S)-3-[2-(2-aminothiazol-4-yl)-(Z)-2-(1-carboxy-1-methylethoxyimino)acetamido]-1-carboxymethoxy-4-methyl-2-azetidinone disodium salt as obtained in Example 3, and 0.072 ml of chloromethyl pivalate and 51 mg of sodium bromide are added to the solution, followed by stirring at room temperature (15° to 25° C.). 18 hours later, 0.029 ml of chloromethyl pivalate and mg of sodium bromide are furthermore added, followed by stirring for another 1 hour. The reaction solution is poured into 10 ml of ice-cold water, and the mixture is extracted with ethyl acetate. The extract is washed with aqueous sodium chloride solution, dried over anhydrous magnesium sulfate and concentrated under reduced pressure. The residue is purified by column chromatography (silica gel, 25 g; a mixed solution (1:1) of ethyl acetate and n-hexane) to give 68 mg (51.7%) of the above-identified compound as a coiorless foamy product.

IR (KBr) cm$^{-1}$: 3,370(br.) 1,780(sh.), 1,750, 1,680, 1,625, 1,535.

NMR (CDCl$_3$)δ: 1.07(9H,s,3×CH$_3$), 1.18(9H,s,3xCH$_3$), 1.54 (3H,d,J=6 Hz,CH$_3$),1.58(6H,s,2×CH$_3$), 4.11(1H,d.q,J=1.5 &6 Hz,C$_4$-H), 4.42(1H,d.d,J=1.5&7.5 Hz,C$_3$-H), 4.62(2H, ABq,J=16 Hz,OCH$_2$COO), 5.70(2H,s,COOCH$_2$O), 5.77(2H,s, COOCH$_2$O), 6.48(2H,br.s,thiazole-2-NH$_2$), 6.82(1H,s, thiazole-5-H), 7.26(1H,d,J=7.5 Hz,C$_3$-NH).

Elemental analysis, for C$_{27}$H$_{39}$N$_5$O$_{12}$S

|  | C (%) | H (%) | N (%) |
|---|---|---|---|
| Calcd. | 49.31 | 5.98 | 10.65 |
| Found | 49.17 | 5.78 | 10.43 |

$[\alpha]_D^{23}$ −51.3° (c = 0.515, methanol).

EXAMPLE 21

Synthesis of (3S,4S)-3-[2-(2-aminothiazol-4-yl)-(Z)-2-methoxyiminoacetamido]-1-(1-carboxy-1-phenylmethoxy)-4-methyl-2-azetidinone sodium salt.

(a) In 60 ml of acetonitrile is suspended 1.296 g of (3S, 4S)-3-(tert-butoxycarbonylamino)-1-hydroxy-4-methyl-2-azetidinone, and 1.01 ml of triethylamine and 2.268 g of 2-(trimethylsilyl ethyl α-bromophenylacetate are added to the suspension under ice-cooling with stirring. The reaction solution is stirred at room temperature (15° to 25° C.) for 3 hours, and 0.67 ml of triethylamine and 1.51 g of 2-(trimethylsilyl)ethylα-bromophenylacetate are furthermore added. After the stirring at room temperature 15° to 25° C.) for further 1 hour, the reaction solution is concentrated under reduced pressure. Ethyl acetate and water are added to the residue, and the mixture is shaken thoroughly. The ethyl acetate layer is separated, washed with aqueous sodium hydrogen carbonate solution, and aqueous sodium chloride solution successively, and dried over anhydrous magnesium sulfate. The solvent is distilled off under reduced pressure, and the residue is purified by column chromatography (silica gel, 100 g; a mixed solution (1:3) of ethyl acetate and hexane) to give 2.207 g (81.6%) of a mixture of the two diastereomeric forms of (3S,4S)-3-(tert-butoxycarbonylamino-4-methyl-1-{1-phenyl-1-[2-(trimethylsilyl)ethoxycarbonyl]methoxy}-2-azetidinone as a colorless oil. The oil, upon standing, allows either of the two diastreomers to crystallize. The isomer that crystallizes is called "A type isomer", while the other isomer obtainable from the mother liquor remaining after the A type of crystals are collected is called "B type isomer".

Analytical Data of A type:

Melting point, 110°–111° C.

IR (KBr) cm$^{-1}$: 3,350, 1,765, 1,755(sh), 1,740, 1,720, 1,515, 1,180.

NMR (CDCl$_3$)δ: 0.8–1.1(2H,m,SiCH$_2$), 1.37(3H,d,J=6 Hz,CH$_3$), 1.42(9H,s,3×CH$_3$), 3.83(1H,d.q,J=1.5&6 Hz,C$_4$-H), 3.9–4.4(3H,m,COOCH$_2$&C$_3$-H), 4.8–5.2(1H,br,C$_3$-NH), 5.47 (1H,s,OCHCO), 7.2–7.6(5H,m,aromatic proton).

Elemental analysis: for C$_{22}$H$_{34}$N$_2$O$_6$Si

|  | C (%) | H (%) | N (%) |
|---|---|---|---|
| Calcd. | 58.64 | 7.63 | 6.22 |
| Found | 58.94 | 7.63 | 6.24 |

$[\alpha]_D^{23}$ +7.6° (c = 0.675, methanol).

Analytical Data of B type:

IR (neat) cm$^{-1}$: 3,340, 1,780, 1,750, 1,720, 1,510

NMR (CDCl$_3$)δ: 0.8–1.1(2H,m,CH$_2$Si), 1.37(3H,d,J=6 Hz,CH$_3$), 1.40(9H,s,3×CH$_3$), 3.42(1H,d.q,J=1.5&6 Hz,C$_4$-H), 3.9–4.4(3H,m,COOCH$_2$&C$_3$-H), 4.8–5.2(1H,br,C$_3$-NH),5.43 (1H,s,OCHCO), 7.2–7.6(5H,m,aromatic proton).

(b) By subjecting 451 mg of the product (A type) obtained under the above (a) to the same reaction as Example 2 (a), there is obtained 428 mg (70.2%) of (3S,4S)-3-[2-(2-chloroacetamidothiazol-4-yl)-(Z)-2-methoxyiminoacetamido]-4-methyl-1-{1-phenyl-1-[2-(trimethylsilyl)ethoxycarbonyl]methoxy}-2-azetidinone as a colorless foamy product.

IR (KBr) cm$^{-1}$: 3,270 2,960, 1,770(sh), 1,755, 1,680, 1,550.

NMR (CDCl$_3$)δ: 0.7–1.0(2H,m,SiCH$_2$), 1.46(3H,d,J=6 Hz,CH$_3$), 3.98(3H,s,OCH$_3$), 3.9–4.35(3H,m,COOCH$_2$&C$_4$-H), 4.22 (2H,s,ClCH$_2$CO), 4.60(1H,br.d,J=8 Hz,C$_3$-H), 5.46(1H,s OCHCO$_2$), 7.11(1H,s,thiazole-5-H), 7.1-7.5(5H,m,aromatic proton), 8.18(1H,d,J=8 Hz,C$_3$-NH), 10.65(1H,br.s, thiazole-2-NH).

(c) In 15 ml of dried tetrahydrofuran is dissolved the product as obtained under the above (b), and 416 mg of tetra-n-butylammonium fluoride trihydrate is added to the solution, followed by stirring at room temperature (15° to 25° C.). 1 hour later, 189 mg of tetra-n-butyl ammonium fluoride trihydrate is furthermore added, followed by stirring for further 1 hour. 30 ml of ethyl acetate and 15 ml of water are added to the reaction solution, and the mixture is acidified (pH 2) under ice-cooling with 3N hydrochloric acid. The organic layer is separated, washed with aqueous sodium chloride solution, admixed with 30 ml of water and adjusted to pH 6.5 with aqueous sodium hydrogen carbonate solution. The aqueous layered is separated and concentrated under reduced pressure. The residue is purified by column chromatography (Amberlite XAD-2, 150 ml; water, then 10 to 20% aqueous ethanol) and lyophilized to give 229 mg (66.2%) of (3S,4S)-1-(1-carboxy-1-phenylmethoxy)-3-[2-(2-chloroacetamidothiazol-4-yl)-(Z)-2-methoxyiminoacetamido]-methyl-2-azetidinone sodium salt as a colorless powder.

IR (KBr) cm$^{-1}$: 1,775, 1,670(sh), 1,620, 1,550, 1,390, 1,040.

NMR (d$_6$-DMSO)δ: 1.43(3H,d,J=6 Hz,CH$_3$), 3.86(3H,s,OCH$_3$), 4.11(1H,d.d,J=1.5&6 Hz,C$_3$-H), 4.2-4.7(3H,m,C$_4$-H&ClCH$_2$CO), 5.10(1H,s,OCHCOO), 7.15-7.55(6H,m,thiazole-H, aromatic proton), 9.40(1H,d,J=6 Hz,C$_3$-NH).

Elemental analysis, for C$_{20}$H$_{19}$ClN$_5$NaO$_7$S.2.5H$_2$O

|  | C(%) | H(%) | N(%) |
|---|---|---|---|
| Calcd. | 41.64 | 4.19 | 12.14 |
| Found | 41.61 | 4.02 | 12.18 |
| [α]$_D^{23}$ +33.4° (c = 0.595, water) | | | |

(d) In 15 ml of water is dissolved 179 mg of the product as obtained under the above (c), and 50 mg of sodium N-methyldithiocarbamate is added to the solution, followed by stirring at room temperature (15° to 25° C.). 1 hour later, 50 mg of sodium N-methyldithiocarbamate is furthermore added, followed by stirring for further 1 hour. The reaction solution is washed with ether and concentrated under reduced pressure. The residue is purified by column chromatography (Amberlite XAD-2, 200 ml; water, then 5 to 10% aqueous ethanol) and lyophilized to give 134 mg (86.7%) of one isomer (A type) above-identified compound as a colorless powder.

IR (KBr) cm$^{-1}$: 1,770, 1,660(sh),1,620, 1,535, 1,390, 1,040.

NMR (d$_6$-DMSO)δ: 1.32(3H,d,J=6 Hz,CH$_3$), 3.83(3H,s,OCH$_3$), 3.7-4.1(1H,m,C$_4$-H), 4.28(1H,d.d,J=1.5&8 Hz,C$_3$-H), 4.96 (1H,s,OCHCOO), 6.67(1H,s,thiazole-5-H), 7.1-7.5(5H,m, aromatic proton), 9.28(1H,d,J=8 Hz,C$_3$NH).

Elemental analysis, for C$_{18}$H$_{18}$N$_5$NaO$_6$S.2.4H$_2$O

|  | C(%) | H(%) | N(%) |
|---|---|---|---|
| Calcd. | 43.36 | 4.61 | 14.04 |
| Found | 43.55 | 4.37 | 13.89 |
| [α]$_D^{23}$ +42.1° (c = 0.595, H$_2$O) | | | |

(e) By subjecting the product (B type) as obtained under the above (a) to the reaction as is the case with the above (b),(c) and (d), there is obtained other isomer (B type) of the subject compound.

IR (KBr) cm$^{-1}$: 1,770, 1,660(sh), 1,620, 1,530, 1,385, 1,035.

NMR (d$_6$-DMSO)δ: 1.24(3H,d,J=6 Hz,CH$_3$), 3.80(3H,s,OCH$_3$), 4.21 (1H,d.d,J=1.5&7.5 Hz,C$_3$-H), 4.93(1H,s,OCHCOO), 6.60 (1H,s,thiazole-5-H), 7.10-7.55(5H,aromatic proton), 9.20 (1H,d,J=7.5 Hz,C$_3$-NH).

Elemental analysis, for C$_{18}$H$_{18}$N$_5$NaO$_6$S.2H$_2$O

|  | C(%) | H(%) | N(%) |
|---|---|---|---|
| Calcd. | 43.99 | 4.51 | 14.25 |
| Found | 44.07 | 4.21 | 14.14 |

EXAMPLE 22

Synthesis of trans-3-(tert-butoxycarbonylamino)-4-carbamoyl-1-(p-nitrobenzyloxycarbonylmethoxy)-2-azetidinone.

By subjecting 2.60 g of trans-3-(tert-butoxycarbonylamino)-4-carbamoyl-1-hydroxy-2-azetidinone to the same reaction as Example 6, there is obtained 3.64 g (78.4% of the above-identified compound as a yellowish foamy product.

IR (KBr) cm$^{-1}$: 3,400(br.), 1,795, 1,690, 1,530, 1,350.

NMR (d$_6$-DMSO)δ: 1.39(9H,s,3×CH$_3$), 4.05-4.30(1H,m,C$_3$-H), 4.31(1H,d,J=2 Hz,C$_4$-H), 4.73(2H,s,OCH$_2$COO), 5.32(2H,s, COOCH$_2$), 7.37&7.84(each 1H, br.s,CONH$_2$), 7.50-7.75 (1H,m,C$_3$-NH), 7.67(2H,d,J=9 Hz,aromatic proton), 8.33 (2H,d,J=9 Hz,aromatic proton).

EXAMPLE 23

Synthesis of trans-3-[2-(2-aminothiazol-4-yl)-(Z)-2-carboxymethoxyiminoacetamido]-4-carbamoyl-1-carboxymethoxy-2-azetidinone disodium salt.

(a) By subjecting 1.096 g of trans-3-(tert-butoxycarbonylamino)-4-carbamoyl-1-(p-nitrobenzyloxycarbonylmethoxy)-2-azetidinone to the same reaction as Example 9 (a), there is obtained 1.51 g (77.5%) of trans-4-carbamoyl-3-[2-(2-chloroacetamidothiazol-4-yl)-(Z)-2-(p-nitrobenzyloxycarbonylmethoxyimino)acetamido]-1-(p-nitrobenzyloxycarbonylmethoxy)-2-azetidinone as a colorless powder.

IR (KBr) cm$^{-1}$: 3,350(br.), 1,795, 1,750, 1,690, 1,610, 1,520, 1,350.

NMR (d$_6$-DMSO)δ: 4.33(2H,s,ClCH$_2$CO), 4.40-4.65(2H,m,C$_3$-H&C$_4$-H), 4.77(2H,s,OCH$_2$COO), 4.87(2H,s,OCH$_2$COO), 5.32 (2H,s,COOCH$_2$), 5.33(2H,s,COOCH$_2$), 7.45(1H,s,thiazole-5-H), 7.55&7.86(each 1H,br,CONH$_2$), 7.64(4H,d,J=9 Hz,aromatic proton), 8.15(2H,d,J=9 Hz,aromatic proton), 9.47(1H,d, J=8 Hz,C$_3$-NH), 12.92(1H,br.s,thiazole-2-NH).

(b) By subjecting 1.088 g of the product as obtained under the above (a) to the same reaction as Example 9 (b), there is obtained 768 mg (78.3%) of trans-3-[2-(2-aminothiazol-4-yl)-(Z)-2-(p-nitrobenzyloxycarbonylmethoxyimino)acetamido]-4-carbamoyl-1-(p-nitrobenzyloxycarbonylmethoxy)-2-azetidinone as a yellowish powder.

IR (KBr) cm$^-$: 3,350 (br.), 1,790, 1,690, 1,520, 1,350.

NMR (d$_6$-DMSO)δ: 4.4-4.6(2H,m), 4.76(2H,s,OCH$_2$COO), 4.80 (2H,s,OCH$_2$COO), 5.31(2H,s,COOCH$_2$), 5.32(2H,s,COOCH$_2$), 6.79(1H,s,thiazole-5-H), 7.22(2H,br.s,thiazole-2-NH₂), 7.50&7.84(each 1H, br.s,CONH₂), 7.64(4H,d,J=9 Hz,aromatic proton), 8.16(2H,d,J=9 Hz,aromatic proton), 9.32(1H,d, J=8 Hz,C₃-NH).

(c) By subjecting 600 mg of the product as obtained under the above (b) to the same reaction as Example 9 (c), there is obtained 84 mg (18.9%) of the above-identified compound as a yellowish powder.

IR (KBr) cm⁻¹: 1,780, 1,670(sh), 1,610(br.), 1,530.

NMR (D₂O)δ: 4.70(2H,s,OCH₂COO), 4.80(2H,s,OCH₂COO), 4.98 (1H,d,J=2 Hz,C₄-H), 5.16(1H,d,J=2 Hz,C₃-H), 7.24(1H,s, thiazole-5-H).

Elemental analysis, for C₁₃H₁₂N₆Na₂O₉S₂.5H₂O

|  | C (%) | H (%) | N (%) |
|---|---|---|---|
| Calcd. | 30.07 | 3.30 | 16.18 |
| Found | 30.15 | 3.16 | 16.37 |

EXAMPLE 24

Synthesis of (3S,4S)-3-[2-(2-aminothiazol-4-yl)-(Z)-2-(1-carboxy-1-methylethoxyimino)acetamido]-4-methyl-1-pivaloyloxymethoxycarbonylmethoxy-2-azetidinone sodium salt.

(a) In 53 ml of dried tetrahydrofuran are dissolved 2.0 g of N-(benzyloxycarbonyl)-L-threonine-N'-(tert-butoxycarbonylmethoxy)amide and 1.644 g of triphenylphosphine, and 0.942 ml of diethyl azodicarboxylate is added to the solution in a nitorgen atmosphere under cooling with cold water. The reaction solution is stirred at room temperature (15° to 25° C.) for 3 hours, and concentrated under reduced pressure. 20 ml of ethyl acetate and 10 ml of hexane are added to the residue, and the mixture is allowed to stand in a refrigerator overnight. The crystals which separate out are filterd off, and the filtrate is concentrated under reduced pressure. The residue is purified by column chromatography (silica gel, 60 g; a mixed solution (1:2, then 1;1) of ethylacettte and n-hexane) to give 1.70 g (89.2%) of (3S,4S)-3-benzyloxycarbonylamino-1-tert-butoxycarbonylmethoxy)-4-methyl-2-azetidinone as a colorless oil.

IR (Neat) cm⁻¹: 3,330, 1,790, 1,750, 1,530, 1,250(br.), 1,160.

NMR (d₆-DMSO)δ: 1.35(3H,d,J=6 Hz,CH₃), 1.43(9H,s,3xCH₃), 3.85(1H,d.q,J=2&6 Hz,C₄-H), 4.05(1H,d.d,J=2&8 Hz,C₃-H), 4.42(2H,ABq,J=16 Hz,OCH₂COO), 5.03(2H,s,COOCH₂), 7.33 (5H,s,aromatic proton), 7.93(1H,d,J=8 Hz,C₃-NH).

(b) In 40 ml of methanol is dissolved 1.822 g of the product as obtained under the above (a), and 400 mg of 5% palladium-charcoal is added to the solution, followed by stirring under a hydrogen atmosphere at room temperature (15° to 25° C.) for 1 hour. The catalyst is filtered off, and the filtrate is concentrated under reduced pressure. The residue is dissolved in 100 ml of dichloromethane, and 3.50 ml of triethylamine and 3.24 g of 2-(2-chloroacetamidothiazol-4-yl)-(Z)-2-[1-methyl-1-(p-nitrobenzyloxycarbonyl)ethoxyimino]acetyl chloride hydrochloride are added to the solution under ice-cooling with stirring. The reaction solution is stirred under ice-cooling for 50 minutes, and concentrated under reduced pressure. Water and ethyl acetate are added to the residue, and the mixture is shaken. The ethyl acetate layer is separated, washed with dilute hydrochloric acid, water, aqueous sodium hydrogen carbonate solution and aqueous sodium chloride solution successively, and dried over anhydrous magnesium sulfate. The solvent is distilled off under reduced pressure, and the residue is purified by column chromatograph (silica gel, 150 g; a mixed solution (1:1) of ethyl acetate and chloroform)to give 1.904 g (54.6%) of (3S,4S)-1-(tert-butoxycarbonylmethoxy)-3-{2-(2-chloroacetamidothiazol-4-yl)-(Z)-2-[1-methyl-1-(p-nitrobenzyloxycarbonyl)ethoxyimino]-acetamido}-4-methyl-2-azetidinone as a colorless foamy product.

IR (Neat) cm⁻¹: 3,380, 1,780, 1,750, 1,680, 1,550, 1,530, 1,350, 1,160.

NMR (d₆DMSO)δ: 1.43(3H,d,J=6 Hz,CH₃), 1.44(9H,s,3xC₃), 1.50(6H,s,2xCH₃), 3.8–4.2(1H,m,C₄-H),4.30–4.55(1H,m, C₃-H), 4.33(2H,s,ClCH₂CO), 4.48(2H,ABq,J=1 Hz,OCH₂COO), 5.32(2H,s,COOCH₂), 7.37(1H,thiazole-5-H), 7.61(2H,d, J=9 Hz,aromatic proton), 8.08(2H,d,J=9 Hz,aromatic proton), 9.18(1H,d,J=8 Hz,C₃-NH), 12.89(1H,br.s,thiazole-2-NH).

(c) By subjecting 1.80 g of the product as obtained under the above (b) to the same reaction as Example 3 (b), there is obtained 1.55 g (96.8%) of (3S,4S)-3-{2-(2-aminothiazol-4-yl)-(Z)-2-[1-methyl-1-(p-nitrobenzyloxycarbonyl)ethoxyimino]-acetamido}-1-(tert-butoxycarbonylmethoxy)-4-methyl-2-azetidinone as a yellow foamy product.

IR (KBr) cm⁻¹: 3,430, 3,350, 1,790, 1,785, 1,685, 1,530, 1,350, 1,160.

NMR (d₆-DMSO)δ: 1.35–1.55(18H,m,6xH₃), 3.8–4.1(1H,m,C₄-H), 4.37(1H,d.d,J=2&7.5 Hz,C₃-H), 4.47(2H,ABq,J=16 Hz,OCH₂COO), 5.33(2H,s,COOCH₂), 6.70(1H,s,thiazole-5-H), 7.27(2H,br.s, thiazole-2-NH₂), 7.65(2H,d,J=9 Hz,aromatic proton), 8.14 (2H,d,J=9 Hz,aromatic proton), 9.07(1H,d,J=7.5 Hz,C₃-NH).

(d) In 50 ml of dichloromethane is dissolved 1.48 g of the product as obtained under the above (c), and 5 ml of anisole and 50 ml of trifluoroacetic acid are added to the solution under ice-cooling with stirring. The reaction solution is stirred under ice-cooling for 3 hours and then at 10° C. for 1 hour. 20 ml of toluene is added, and the mixture is concentrated under reduced pressure. 50 ml of ethyl acetate and 50 ml of water are added to the residue, and the mixture is adjusted to pH 6.5 to 7 with aqueous sodium hydrogen carbonate solution. The aqueous layer is separated, and the organic layer is extracted with water. The aqueous layers are combined, adjusted to pH 6.0 with 1N hydrochloric acid and concentrated under reduced pressure. The residue is purified by column chromatography (Amberlite XAD-2, 300 ml; water, then 10–30% aqueous ethanol) and lyophilized to give 920 mg (62.9%) of (3S,4S)-3-{2-(2-aminothiazol-4-yl)-(Z)-2-[1-methyl-1-(p-nitrobenzyloxycarbonyl)ethoxyimino]acetamido}-1-carboxymethoxy-4-methyl-2-azetidinone sodium salt as a yellowish powder.

IR (KBr) cm⁻¹: 1,775, 1,750(sh), 1,675, 1,625, 1,530, 1,350, 1,150.

NMR (d₆-DMSO)δ: 1.43(3H,d,J=6 Hz,CH₃), 1.48(6H,s,2xCH₃), 3.8–4.1(1H,m,C₄-H), 4.02(2H,s,OCH₂COO), 4.34(1H,d.d, J=1.5&7.5 Hz,C₃-H), 6.68(1H,s,thiazole-5-H), 7.23(2H, br.s,thiazole-2-NH₂), 7.64(2H,d,J=9 Hz,aromatic proton), 8.12(2H,d,J=9 Hz,aromatic proton), 9.14(1H,d,J=7.5 Hz, C₃-NH).

Elemental analysis, for C₂₂H₂₃N₆NaO₁₀S.1.5H₂O

|  | C (%) | H (%) | N (%) |
|---|---|---|---|
| Calcd. | 43.07 | 4.27 | 13.70 |
| Found | 43.25 | 4.16 | 13.62 |
| $[\alpha]_D^{23}$ −45.3° (c = 0.775, water). | | | |

(e) By subjecting 860 mg of the product as obtained under the above (a) to the same reaction as Example 20, there is obtained 870 mg (87.4%) of (3S,4S)-3-{2-(2-aminothiazol-4-yl)-(Z)-2-[1-methyl-1-(p-nitrobenzyloxycarbonyl)ethoxyimino]-acetamino}-4-methyl-1-(pivaloyloxymethoxycarbonylmethoxy)-2-azetidinone as a yellowish foamy product.

IR (KBr) cm$^{-1}$: 3,430(br.), 1,790, 1,755, 1,685, 1,530, 1,350.

NMR (d$_6$-DMSO)δ: 1.14(9H,s,3xCH$_3$), 1.43(3H,d,J=6 Hz,CH$_3$), 1.48(6H,s,2xCH$_3$), 3.75–4.05(1H,m,C$_4$-H), 4.39[1H,d.d, J=2&8 Hz,C$_3$-H), 4.69(2H,ABq,J=17 Hz,OCH$_2$COO), 5.33(2H,s, COOCH$_2$), 5.76(2H,s,OCH$_2$O), 6.70(1H,s,thiazole-5-H), 7.26(2H,br.s,thiazole-2-NH$_2$), 7.63(2H,d,J=9 Hz,aromatic proton), 8.13(2H,d,J=9 Hz,aromatic proton), 9.02(1H,d, J=8 Hz,C$_3$-NH).

(f) In a mixed solution of 40 ml of tetrahydrofuran and 40 ml of water is dissolved 810 mg of the product as obtained under the above (e), and 810 mg of 10% palladium-charcoal is added to the solution, followed by stirring under a hydrogen atmosphere at room temperature (15° to 25° C.) for 1 hour. A solution of 200 mg of sodium hydrogen carbonate in 10 ml of water is added to the reaction solution, and the catalyst is filtered off and washed with 50 ml of a mixed solution (1:1) of water and tetrahydrofuran and 50 ml of water successively. The filtrate and washings are combined and concentrated under reduced pressure to distill off the tetrahydrofuran. The residual aqueous solution is washed with ethyl acetate and concentrated again under reduced pressure. The residue is purified by column chromatography (Amberlite XAD-2, 200 ml; water, then 10 to 30% aqueous ethanol) and lyophilized to give 280 mg (41.6%) of the above-identified compound as a colorless powder.

IR (KBr) cm$^{-1}$: 1,780, 1,675, 1,595, 1,540, 1,225.

NMR (d$_6$-DMSO)δ: 1.16(9H,s,3xCH$_3$), 1.37(6H,s,2xCH$_3$), 1.40 (3H,d,J=6 Hz,CH$_3$), 3.8–4.1(1H,m,C$_4$-H), 4.32(1H,d.d,J=2&8 Hz,C$_3$-H), 4.67(2H,ABq,J=17 Hz,OCH$_2$COO), 5.76(2H, ABq,J=6 Hz,OCH$_2$O), 6.70(1H,s,thiazole-5-H), 7.11(2H, br.s,thiazole-2-NH$_2$), 11.66(1H,d,J=8 Hz,C$_3$-NH).

Elemental analysis, for C$_{21}$H$_{28}$N$_5$NaO$_{10}$S.H$_2$O

|  | C(%) | H(%) | N(%) |
|---|---|---|---|
| Calcd. | 43.22 | 5.18 | 12.00 |
| Found | 42.95 | 5.10 | 11.99 |
| $[\alpha]_D^{24}$ −47.0° (c = 0.795, H$_2$O) | | | |

Reference Example 1

In 100 ml of ethyl acetate is suspended 4.0 g (10 mmole) of N-(tert-butoxycarbonyl)-L-threonine dicyclohexylamine salt, and 50 ml of 0.2N sulfuric acid is added little by little to the solution under ice-cooling. The ethyl acetate layer is separated, and the aqueous layer is extracted four times with ethyl acetate. The ethyl acetate layers are combined, washed with a small amount of aqueous saturated sodium chloride solution and dried over anhydrous sodium sulfate. The solvent is distilled off under reduced pressure, and 50 ml of tetrahydrofuran, 1.68 g of 1-hydroxybenzotriazole and 3.39 g of O-(p-nitrobenzyloxycarbonylmethyl)hydroxylamine (prepared by the method as described in the Japanese Unexamined Patent Publication No. 131758/1982) are added to the residue, followed by addition of 2.27 g of dicyclohexylcarbodiimide under ice-cooling with stirring. The reaction solution is stirred at room temperature for 16 hours, and the insoluble matter is filtered off, while the filtrate is concentrated under reduced pressure. The residue is purified by column chromatography (silica gel, 180 g; ethyl acetate-CHCl$_3$= 1:1, then 3:2) to give 3.71 g (86.9%) of N-(tert-butoxycarbonyl)-L-threonine-N'-(p-nitrobenzyloxycarbonylmethoxy)amide as a colorless foamy product.

IR (KBr) cm$^{-1}$: 3,380, 1,750, 1,680, 1,525, 1,350.

NMR (d$_6$-DMSO)δ: 1.01(3H,d,J=6 Hz,CH$_3$), 1.37(9H,s,3xCH$_3$), 3.6–4.0(2H,m,2xCH), 4.56(2H,s,OCH$_2$COO), 4.76(1H,d, J=5 Hz,OH), 5.33(2H,s,COOCH$_2$), 6.26(1H,d,J=8 Hz,BocNH), 7.56(2H,d,J=9 Hz,aromatic proton), 8.22(2H,d,J=9 Hz, aromatic proton).

Reference Example 2

In 15 ml of pyridine is dissolved 3.40 g (7.96 mmole) of N-(tert-butoxycarbonyl)-L-threonine-N'-(p-nitrobenzyloxycarbonylmethoxy)amide, and 0.80 ml of methanesulfonyl chloride is adde to the solution under a nitrogen stream at −20° C. After the stirring under ice-cooling for 6 hours ethyl acetate is added to the reaction solution, which is then adjusted to pH 2 with 3N hydrochloric acid. The ethyl acetate layer is separated, washed with aqueous sodium chloride solution, aqueous sodium hydrogen carbonate solution and aqueous sodium chloride solution successively, and dried over anhydrous magnesium sulfate. The solvent is distilled off under reduced pressure, and after ether is added to the residue, the resulting colorless powder is recovered by filtration and washed with ether to give 3.16 g (78.5%) of N-(tert-butoxycarbonyl)-O-methanesulfonyl-L-threonine-N'-(p-nitrobenzyloxycarbonylmethoxy)amide.

Melting point, 53°–56° C.

IR (KBr) cm$^{-1}$: 3,360, 2,990, 1,760, 1,700(br.), 1,670, 1,525, 1,350, 1,170.

NMR (d$_6$-DMSO)δ: 1.27(3H,d,J=6 Hz,CH$_3$), 1.37(9H,s,3xCH$_3$), 3.08(3H,s,SO$_2$CH$_3$), 4.0–4.3(1H,m,CHNH), 4.58(2H,s, OCH$_2$COO), 4.7–4.9(1H,m,CHOH), 5.31(2H,s,COOCH$_2$), 6.91 (1H,d,J=8 Hz,BocNH), 7.65(2H,d,J=9 Hz,aromatic proton), 8.22(2H,d,J=9 Hz,aromatic proton), 11.70(1H,br.s,CONHO).

Reference Example 3

In 20 ml of MeOH is dissolved 2.95 g (10 mmole) of N-(tert-butoxycarbonyl)-O-benzyl-L-serine, and 0.6 g of 5% palladium-charcoal is added to the solution, followed by stirring under a hydrogen atmoshhere at room temperature for 1.5 hours. The catalyst is filtered off, and the filtrate is concentrated under reduced pressure. The residue is dissolved in a mixed solution of 50 ml of tetrahydrofuran and 100 m of water, and 2.71 g of O-(p-nitrobenzyloxycarbonylmethyl)hydroxylamine is added to the solution, which is adjusted to pH 4, followed by addition of an aqueous solution containing 2.30 g of 1-ethyl-3-(3-dimethylaminopropyl)carbodiimide. The reaction solution is stirred at room temperature for 2 hours while adjusting it to pH 4 to 4.5, and extracted with ethyl acetate. The extract is washed with 1N citric acid, water, aqueous sodium hydrogen carbonate solution and aqueous sodium chloride solution successively, and dried over anhydrous magnesium sulfate. The solvent is distilled off under reduced pressure, and after a mixed solution (2:1) of ethyl acetate and n-hexane is added to the residue, the resulting colorless powder is recovered by filtration. The filtrate is concentrated, and the residue is purified by column chromatography (silica gel, 200 g; ethyl acetate-CHCl₃, 2:1). The resulting powder and the powder previously obtained are combined and washed with ether to give 1.785 g (43.2%) of N-tert-butoxycarbonyl-L-serine-N'-(p-nitrobenzyloxycarbonylmethoxy)amide.

Melting point, 121°–122° C.

IR (KBr) cm$^{-1}$: 3,310, 1,750, 1,670, 1,530, 1,350.

NMR (d₆-DMSO)δ: 1.37(9H,s,3×CH₃), 3.35–3.61(2H,m,CH₂OH), 3.7–4.05(1H,m,CH), 4.54(2H,s,OCH₂COO), 4.82(1H,t,J=6 Hz,OH), 5.32(2H,s,COOCH₂), 6.58(1H,d,J=8 Hz,BocNH), 7.64(2H,d,J=9 Hz, aromatic proton), 8.22(2H,J=9 Hz, aromatic proton),11.29(1H,br.s,CONHO)

Elemental analysis, for $C_{17}N_{23}N_3O_9$

|  | C(%) | H(%) | N(%) |
| --- | --- | --- | --- |
| Calcd. | 49.39 | 5.61 | 10.16 |
| Found | 49.22 | 5.54 | 10.10 |

Reference Example 4

In 40 ml of pyridine is dissolved 5.99 g (14.5 mmole) of (tert-butoxycarbonyl)-L-serine-N'-(p-nitrobenzyloxycarbonylmethoxy)amide, and 1.68 ml of methanesulfonyl chloride is added to the solution under a nitrogen stream at −20° to −30° C. The temperature of the reaction solution is gradually elevated until it reaches 0° C. over the period of 30 minutes, and stirring is effected under ice-cooling for 1 hour. 300 ml of ethyl acetate is added to the reaction solution, which is then adjusted to pH 2 to 2.5 with 3N hydrochloric acid. The ethyl acetate layer is separated, washed with aqueous sodium chloride solution, aqueous sodium hydrogen carbonate solution and aqueous sodium chloride solution successively, and dried over anhydrous magnesium sulfate. The solvent is distilled off under reduced pressure, and the residue, upon standing at room temperature, partially crystallizes out. After 25 ml of ethyl acetate and 25 ml of ether are added, crystals are recovered by filtration to give 2.05 g (28.9%) of N-tert-butoxycarbonyl)-O-methane-sulfonyl-L-serine-N'-(p-nitrobenzyloxycarbonylmethoxy)amide as colorless crystals. The mother liquor is concentrated under reduced pressure, and the residue is purified by column chromatography (silica gel, 100 g; ethyl acetate-chloroform=3:2, then 2:1). The resulting solid is washed with a mixed solution (1:1) of ethyl acetate and name to give furthermore 2.92 g of the above crystals. Total yield of 4.97 g (69.8%).

Melting point, 102°–104° C.

IR (KBr) cm$^{-1}$: 3,350, 3,280, 1,770, 1,680, 1,515, 1,360, 1,185.

NMR (d₆-DMSO)δ: 1.39(9H,s,3xCH₃), 3.13(3H,s,CH₃SO₂) 4.1–4.4(3H,m,CHCH₂SO₂), 4.56(2H,s,OCH₂COO), 5.32(2H, COOCH₂), 7.0–7.25(1H,m,CHNH), 7.64(2H,d,J=9 Hz,aromatic proton), 8.21(2H,d,J=9 Hz,aromatic proton), 11.64(1H, br.,CONHO).

Elemental analysis, for $C_{18}H_{25}N_3O_{11}S$

|  | C(%) | H(%) | N(%) |
| --- | --- | --- | --- |
| Calcd. | 43.99 | 5.13 | 8.55 |
| Found | 44.11 | 5.19 | 8.51 |
| $[\alpha]_D^{24}$ −15.2° (c = 0.9, MeOH) | | | |

Reference Example 5

In 50 ml of ethanol is dissolved 13.1 g (69.7 mmole), of diethyl (2R,3R)-epoxysuccinate, and a solution of 3.94 g of potassium hydroxide in 120 ml of ethanol is added dropwise to the solution under ice-cooling with stirring. After the stirring under ice-cooling for 3 hours, the ethanol is distilled off under reduced pressure. 50 ml of water and 100 ml of ether are added to the residue to a solution, and the aqueous layer is separated. The ether layer is extracted three times with dilute aqueous sodium chloride solution, and the aqueous layers are combined and acidified with 3N hydrochloric acid. The solution, after being saturated with sodium chloride, is extracted four times with ethyl acetate, and the extract is washed with aqueous sodium chloride solution and dried over anhydrous magnesium sulfate. The solvent is distilled off under reduced pressure, and the residue is distilled under reduced pressure to give 4.76 g (42.7%) of (2R,3R)-epoxysuccinic acid monoethyl ester as a colorless oil having a boiling point of 121°–122° C. (0.85 mmHg). The product, upon standing, crystallizes, and the crystals are recrystallized from isopropyl ether-petroleum ether (1:2) to give colorless crystals.

Melting point, 55°–56° C.

IR (KBr) cm$^{-1}$: 3,420(br.), 1,740(br.), 1,380, 1,310, 1,210.

NMR CDCl₃)δ: 1.33(3H,t,J=7 Hz,CH₃), 3.72(2H,s,2xCH), 4.28 (2H,q,J=7 Hz,CH₂), 10.63(1H,s,COOH).

Elemental analysis, for $C_6H_8O_5$

|  | C(%) | H(%) |
| --- | --- | --- |
| Calcd. | 45.01 | 5.04 |
| Found | 44.81 | 5.12 |
| $[\alpha]_D^{23}$ −119.0° (c = 0.985, ethanol) | | |

REFERENCE EXAMPLE 6

In 60 ml of ammonium hydroxide is dissolved 3.2 g(20 mmole) of (2R,3R)-epoxysuccinic acid monoethyl ester, and the solution is stirred at 45° to 50° C. for 23 hours. The reaction solution is concentrated under reduced pressure, and the residual solid is recrystallized from water to give 2.12 g of colorless crystals. A 2.0 g portion of the crystals is recrystallized from water-ethanol to yield 1.9 g 68%) of L-erythro-3-hydroxyasparagine as colorless crystals. This product does not exhibit a definite melting point.

IR (KBr) cm$^{-1}$: 3,360, 3,180, 1,690, 1,670, 1,510, 1,405, 1,290, 1,170.

Elemental analysis, for $C_4H_8N_2O_4$

|  | C(%) | H(%) | N(%) |
| --- | --- | --- | --- |
| Calcd. | 32.44 | 5.44 | 18.91 |
| Found | 32.39 | 5.50 | 19.11 |

-continued

| | C(%) | H(%) | N(%) |
|---|---|---|---|

$[\alpha]_D^{23}$ +46.7° (c = 0.54, water)

REFERENCE EXAMPLE 7

In 15 ml of a mixed solution (1:1) of dioxane and water is suspended 740 mg (5 mmole) of L-erythro-3-hydroxyasparagine, and 1.4 ml of trietyylamine and 1.74 g of di-tert-butyl dicarbonate are added to the suspension, followed by stirring at room temperature for 3 hours. 25 ml of ethyl acetate and 12 ml of water are added to the reaction solution, and the mixture is shaken. The aqueous layer is separated, and the organic layer is extracted with aqueous sodium chloride solution. The aqueous layers are combined and adjusted under ice-cooling to pH 1.5 to 2 with 10% aqueous potassium hydrogen sulfate solution, followed by dissolution of sodium chloride until saturation. The solution is extracted four times with a mixed solution (2:1) of ethyl acetate and tetrahydrofuran and twice with ethyl acetate. The extract is washed with aqueous sodium chloride solution and dried over anhydrous magnesium sulfate. The solvent is distilled off under reduced pressure, and 30 ml of ether is added to the residue. The mixture is allowed to stand under cooling overnight and filtered to give 1.04 g (84%) of L-erythro-N-(tert-butoxycarbonyl)-3-hydroxyasparagine, Melting point, 121°–124° C. (decomp.).

IR (KBr) cm$^{-1}$: 3400, 3300 (br.), 1720, 1675, 1600, 1520.

NMR (d$_6$-DMSO)δ: 1.39(9H,s,3xCH$_3$), 4.07(1H,d,J=3 Hz,CHOH), 4.42(1H,d.d,J=3&9 Hz,CHNH), 6.23(1H,J=9 Hz,CHNH), 6.95–7.45(2H-,CONH$_2$).

Elemental analysis, for C$_9$H$_{16}$N$_2$O$_6$·¼H$_2$O

| | C(%) | H(%) | N(%) |
|---|---|---|---|
| Calcd. | 42.77 | 6.53 | 11.09 |
| Found | 42.82 | 6.63 | 10.85 |

$[\alpha]_D^{23}$ +27.5° (c = 0.9, water)

REFERENCE EXAMPLE 8

In 50 ml of water are dissolved 1.24 g (5 mmole) of L-erythro-N-(tert-butoxycarbonyl)-3-hydroxyasparagine and 630 mg of sodium hydrogen carbonate, and after the addition of 1.2 g of O-benzylhydroxylamine hydrochloride, the reaction solution is adjusted to pH 4. An aqueous solution of 1.05 g of 1-ethyl-3-(3-dimethylaminopropyl)carbodiimide hydrochloriee in 5 ml of water is added, and the mixture is stirred at room temperature for 3 hours while maintaining it to pH 4 to 5. The reaction solution is saturated with sodium chloride, and extracted with a mixed solution (4:1) of ethyl acetate and tetrahydrofuran. The extract is washed with 1N citric acid, 3% aqueous sodium hydrogen carbonate solution and aqueous sodium chloride solution succesively and dried over anhydrous magnesium sulfate. The solvent is distilled off under reduced pressure, whereby the residue crystallizes. Recrystallization from ethyl acetate yields 888 mg (50.3%) of L-erythro-N$^\alpha$-benzyloxy-N-(tert-butoxycarbonyl)3-hydroxyaspartic acid diamide as colorless crystals.

Melting point, 146°–148° C.

IR (KBr) cm$^{-1}$: 3,310, 3,220, 1,690, 1,670, 1,530.

NMR (d$_6$-DMSO)δ: 1.37(9H,s,3×CH$_3$), 3.85–4.25(2H,2×CH), 4.77 (2H,s,OCH$_2$), 5.4–5.7(1-H,OH), 6.2–6.55(1H,CONH), 7.05–7.30(2H,CONH$_2$), 7.39(5H,s,Ph), 10.8–11.3(1H,CONH).

REFERENCE EXAMPLE 9

In 30 ml of pyridine is dissolved 2.12 g (6 mmole) of L-erythro-Nα-benzyloxy-N-(tert-butoxycarbonyl)-3-hydroxyaspartic acid diamide, and 0.6 ml of methanesulfonyl chloride is added dropwise to the solution under an argon atmosphere at −20° C. The reaction solution is stirred at −20° C. for 30 minutes and then at 3° to 5° C. for 20 hours, and a mixed solution (1:1) of ethyl acetate and tetrahydrofuran is added to it under ice-cooling. The aqueous layer is adjusted to pH 2 with 6N hydrochloric acid, and after the mixture is shaken thoroughly, the organic layer is separated, while the aqueous layer is extracted again with ethyl acetate. The organic layers are combined, washed with aqueous sodium chloride solution and dried over anhydrous magnesium sulfate. The solvent is distilled off under reduced pressure, and ether is added to the residue, followed by filtration to give 1.84 g (71.2%) of L-erythro-Nα-benzyloxy-N-(tert-butoxycarbonyl)-3-methanesulfonyloxyaspartic acid diamide as colorless crystals.

Melting point, 138°–140° C. (decomp.)

IR (KBr) cm$^{-1}$: 3,310, 3,230(sh.), 1,690, 1,670, 1,530, 1,370, 1,180.

NMR (d$_6$-DMSO)δ: 1.40(9H,s,3×CH$_3$), 3.13(3H,s,SO$_2$CH$_3$), 4.2–4.5(1H,CHNH), 4.80(2H,s,OCH$_2$), 4.98(1H,d,J=7.5 Hz,CHOSO$_2$), 6.45–6.75(1H,CONH), 7.2–7.7(7H,Ph&CONH$_2$), 11.58(1H,br.s, CONH).

Elemental analysis, for C$_{17}$H$_{25}$N$_3$O$_8$S

| | C(%) | H(%) | N(%) |
|---|---|---|---|
| Calcd. | 47.32 | 5.84 | 9.74 |
| Found | 47.59 | 5.97 | 9.75 |

$[\alpha]_D^{25}$ +1.3° (c = 0.985, DMSO)

REFERENCE EXAMPLE 10

In 750 ml of acetone is dissolved 3.24 g (7.5 mmole) of L-erythro-N$^\alpha$-benzyloxy-N-(tert-butoxycarbonyl)-3-methanesulfonyloxyaspartic acid diamide, and 3.11 g of potassium carbonate is added to the solution under an argon atmosphere. The reaction solution is stirred for 20 minutes wiile elevating the temperature, and furthermore stirred at 50° C. for 35 minutes after the temperature reaches 50° C. After being cooled, the reaction solution is filtered and washed with 400 ml of warmed tetrahydrofuran. The filtrate and washing are combined and concentrated under reduced pressure, and a mixed solution (1:1) of tetrahydrofuran and ethyl acetate and water are added to the residue, followed by thorough shaking. The organic layer is separated, and the water layer is extracted with a mixed solution of ethyl acetate and tetrahydrofuran. The organic layers are combined, washed with aqueous sodium chloride solution, aqueous sodium hydrogen carbonate solution and aqueous sodium chloride solution successively, and dried over anhydrous magnesium sulfate. The solvent is distilled off under reduced pressure, and ether is added to the residue, followed by filtration to give 2.3 g (91.5%) of (3S,4S)-1- C benzyloxy-3-tert-butoxycarbonylamino)-4-carbamoyl-2-azetidnnone as colorless crystals.

Melting point, 232°–235° C. (decomp.).

IR (KBr) cm$^{-1}$: 3,330, 3,170, 1,795, 1,700, 1,665, 1,530.

NMR (d$_6$-DMSO)δ: 1.37(9H,s,3×CH$_3$), 4.47(1H,d,J=5 Hz,C$_4$-H), 4.92(1H,d.d,J=5&9 Hz,C$_3$-H), 4.99(2H,s,OCH$_2$), 6.95(1H,d, J=9 Hz,C$_3$-NH), 7.40(5H,s,aromatic proton), 7.46(2H,br.s, CONH$_2$).

Elemental analysis, for C$_{16}$H$_{21}$N$_3$O$_5$

| | C(%) | H(%) | N(%) |
|---|---|---|---|
| Calcd. | 57.30 | 6.31 | 12.53 |
| Found | 57.40 | 6.42 | 12.51 |
| [α]$_D^{23}$ +31.3° (c = 0.45, DMSO) | | | |

REFERENCE EXAMPLE 11

In 40 ml of MeOH is suspended 671 mg (2 mmole) of (3S,4S)- benzyloxy-3-(tert- butoxycarboxamido)-4-carbamoyl-2-azetidinone, and 140 mg of 10% palladium-charcoal is added to the suspension, followed by stirring under a hydrogen atmosphere at room temperature for 25 minutes. The catalyst is filtered off, and the filtrate is concentrated under reduced pressure. Ether is added to the residue, and the precipitate that separates out is recovered by fitlration to give 435 mg (85.6%) of (3S,4S) -3-(tert-butoxycarbonylamino)-4-carbamoyl-1-hydroxy-2-azetidinone. This product does not show a definite melting point, discolors as from about 130° C. and decomposes at about 156° C.

IR (KBr) cm$^{-1}$: 3,330, 3,190, 1,780, 1,690, 1,665, 1,525, 1,165.

NMR (d$_6$-DMSO)δ: 1.37(9H,s,3×CH$_3$), 4.32(1H,d,J=5 Hz,C$_4$-H), 4.88(1H,d.d,J=5&9 Hz,C$_3$-H), 6.90(1H,d,J=9 Hz,C$_3$-NH).

Elemental analysis, for C$_9$H$_{15}$N$_3$O$_5$·½H$_2$O

| | C(%) | H(%) | N(%) |
|---|---|---|---|
| Calcd. | 42.52 | 6.34 | 16.53 |
| Found | 42.79 | 6.46 | 16.34 |
| [α]$_D^{25}$ +18.5° (c = 0.5, MeOH). | | | |

REFERENCE EXAMPLE 12

In 48 ml of tetrahydrofuran are dissolved 1.99 g (8 mmole) of L-erythro-N-(tert-butoxycarbonyl)-3-hydroxyasparagine, 2.35 g of O-(p-nitrobenzyloxycarbonylmethyl)hydroxylamine and 1.35 g of 1-hydroxybenzotriazole, and 1.82 g of dicyclohexylcarbodiimide is added to the solution under ice-cooling with stirring. After stirring at room temperature for 19 hours, the insoluble matter is filtered off, and washed with ethyl acetate. The filtrate and washing are combined and concentrated under reduced pressure, and the residue is dissolved in a mixed solution (4:1) of ethyl acetate and tetrahydrofuran. The solution is washed with aqueous sodium hydrogen carbonate solution, aqueous sodium chloride solution, dilute hydrochloric acid and aqueous sodium chloride solution successively, and dried over anhydrous magnesium sulfate. The solvett is distilled off under reduced pressure, and after 40 ml of ethyl acetate and 20 ml of hexane are added to the residue, the resulting powder is recovered by filtration to give 2.14 g (58.6%) of L-erythro-N$^α$-(p-nitrobenzyloxycarbonyl-methoxy)-N-(tert-butoxycarbonyl)-3-hydroxyasparagine.

Melting point, 140°–142° C.

IR (KBr) cm$^{-1}$: 3,360, 1,750, 1,670, 1,525, 1,350.

NMR (d$_6$-DMSO)δ: 1.37(9H,s,3×CH$_3$), 3.9–4.25(2H,m,C$_2$-H&C$_3$-H), 4.53(2H,s,OCH$_2$COO), 5.33(2H,s,COOCH$_2$), 6.45(1H,d,J=9 Hz, C$_2$NH), 7.0–7.35(2H,m,CONH$_2$), 7.66(2H,d,J=9 Hz,aromatic proton), 8.22(2H,d,J=9 Hz,aromatic proton), 11.12(1H, br.,CONHO).

REFERENCE EXAMPLE 13

In 10 ml of pyridine is dissolved 1.14 g (2.5 mmole) of L-erythro-Nα-(p-nitrobenzyloxycarbonylmethoxy)-N-(tert-butoxycarbonyl)-3-hydroxyasparagine, and 0.25 ml of methanesulfonyl chloride is added dropwise to the solution at −20° C. After stirring under ice-cooling for 14 hours, a mixed solution (3:1) of ethyl acetate and tetrahydrofuran is added to the reaction solution, and the mixture is adjusted to pH 2 to 2.5 with 3N hydrochloric acid. The organic layer is separated, washed with aqueous sodium chloride solution, aqueous sodium hydrogen carbonate solution and aqueous sodium chloride solution successively, and dried over anhydrous magnesium sulfate. The solvent is distilled off under reduced pressure, and the residue is washed with cold ethyl acetate and ether to give 965 mg (72.2%) of L-erythro-N$^α$-(p-nitrobenzyloxycarbonylmethoxy)-N-(tert-butoxycarbonyl)-3-methanesulfonyloxyaspartic acid diamide as colorless crystals.

Melting point, 156°–157° C. (decomp.)

IR (KBr) cm$^{31}$ $^1$: 3,440, 3,320, 1,750, 1,695, 1,670, 1,525, 1,370, 1,355.

NMR (d$_6$-DMSO)δ: 1.37(9H,s,3×CH$_3$), 3.13(3H,s,CH$_3$SO$_2$), 4.2–4.6(1H,m,C$_2$-H), 4.56(2H,s,OCH$_2$COO), 4.92(1H,d,J=7 Hz, C$_3$-H), 5.32(2H,s,COOCH$_2$), 6.66(1H,d,J=8 Hz,C$_2$-NH), 7.35–7.65(2H,m,CONH$_2$), 7.65(2H,d,J=9 Hz,aromatic proton), 8.22(2H,d,J=9 Hz,aromatic proton), 11.78(1H,br. s,CONHO).

REFERENCE EXAMPLE 14

A 1.2 l portion of ammonium hydroxide is added little by little to 79.2 g of (2R,3R)-epoxysuccinic acid under ice-water-cooling. The reaction mixture is stirred at 45° to 47° C. for 48 hours and concentrated under reduced pressure, and 200 ml of water is added to the residue, followed by concentration under reduced pressure. The residue is dissolved in 120 ml of water, and 1.2 g of activated charcoal is added to the solution, followed by filtration. 50 ml of concentrated hydrochloric acid is added to the filtrate under ice-water-cooling, and the solution is allowed to stand under cooling overnight. The crystals that separate out are recovered by filtration and washed with 60 ml of cold water to give 73.1 g (81.7%) of L-erythro-3-hydroxyaspartic acid as colorless crystals.

IR (Nujol) cm$^{-1}$: 3,460, 3,210, 1,690.

Elemental analysis, for C$_4$H$_7$NO$_5$

| | C(%) | H(%) | N(%) |
|---|---|---|---|
| Calcd. | 32.22 | 4.73 | 9.40 |
| Found | 32.02 | 4.84 | 9.54 |
| [α]$_D^{24.5}$ +55.6° (c = 0.9, 1 N hydrochloric acid) | | | |

REFERENCE EXAMPLE 15

In 300 ml of methanol is suspended 29.8 g of L-erythro3-hydroxyaspartic acid, and 20 ml of concentrated hydrochloric acid is added to the suspension, followed by heating under reflux for 8 hours. The solvent is distilled off under reduced pressure, and methanol is added to the residue, followed by distillation of the solvent. The solidified residue is dissolved in a mixed solution of 60 ml of water and 60 ml of ethanol, and 15. 8 g of pyridine is added to the solution under ice-water-cooling. The mixture is shaken thoroughly and allowed to stand under cooling overnight. The crystals that separate out are recovered by filtration, and wahsed with 50% ethanol and ethanol successively to give 23.8 g (73%) of L-eythro-3-hydroxyaspartic acid β-methyl ester as colorless crystals. Thin layer chromatography indicates that this product contains a slight amount of the unreacted starting compound. Recrystallization from 50% ethanol yields the pure product as colorless crystals.

melting point, 226°–229° C. (decomp.)
IR (Nujol) cm$^{-1}$: 3,175, 1,770, 1,755, 1,620.
Elemental analysis, for $C_5H_9NO_5$

|  | C(%) | H(%) | N(%) |
|---|---|---|---|
| Calcd. | 36.81 | 5.56 | 8.59 |
| Found | 36.57 | 5.65 | 8.54 |

$[\alpha]_D^{25}$ +64.4° (c = 1,1 N—hydrochloric acid)

REFERENCE EXAMPLE 16

To 20 ml of ammonium hydroxide is added 6.52 g (40 mmole) of L-erythro-3-hydroxyaspartic acid 8-methyl ester, and the solution is stirred at room temperature for 8 hours and concentrated under reduced pressure. After water is added to the residue and the mixture is again concentrated, 80 ml of water and 80 ml of ethanol are added to the residue. The mixture is warmed, shaken thoroughly and allowed to stand under cooling. The crystals are recovered by filtration and washed with 80 ml of cooled 50% ethanol to give 4.7 g (79%) of L-erythro-3-hydroxyasparagine, which shows the IR spectrum in agreement with that of the product obtained in Reference Example 5.

$[\alpha]_D^{24}$ +46.3° (c=0.5,water)

REFERENCE EXAMPLE 17

In a mixed solution of 18 ml of dioxane and 18 ml of water is suspended 3.57 g (30 mmole) of L-allothreonine, and 5.04 ml of triethylamine is added to the suspension under ice-water-cooling. followed by addition of 7.85 g of di-tert-butyl dicarbonate and stirring at room temperature for 3 hours. 1.96 g of di-tert-butyl dicarbonate is furthermore added, followed by stirring at room temperature for further 14 hours. 80 ml of ethyl acetate and 40 ml of water are added to the reaction solution, and after the mixture is shaken thoroughly, the aqueous layer is separated, while the organic layer is extracted with 20 ml of aqueous sodium chloride solution. The aqueous layers are combined, washed with 40 ml of ethyl acetate, and adjusted to pH 2.0 to 2.5 by adding 10% aqueous potassium hydrogen sulfate solution to it under ice-cooling. The solution is salted out with sodium chloride and extracted with four 80 ml portions of ethyl acetate. The extracts are combined, washed twice with saturated aqueous sodium chloride solution and dried over anhydrous magnesium sulfate. The solvent is distilled off under reduced pressure, and the residue is dissolved in 150 ml of tetrahydrofuran, followed by addition of 5.05 g of 1-hydroxybenzotriazole and 8.14 g of O-(p-nitrobenzyloxycarbonylmethyl)hydroxylamine. 6.81 of dicyclohexylcarbodiimide is added to the reaction mixture under ice-cooling with stirring, and the reaction solution is stirred at room temperature for 22 hours. The insoluble matter is filterd off, and the filtrate is concentrated under reduced pressure. The residue is dissolved in a mixed solution (4:1) of ethyl acetate ahd tetrahydrofuran, and the solution is washed with aqueous sodium hydrogen carbonate solution and aqueous sodium chloride solution successively and dried over anhydrous magnesium sulfate. The solvent is distilled off under reduced pressure, and the residue is dissolved in 80 ml of ethyl acetate under heating. 80 ml of hexane is added to the solution, and the powder that separates out is recovered by filtration and wahsed with 200 m of a mixed solution (1:1) of ethyl acetate and hexane to give 10.9 g (85.1%) of N-(tert-butoxycarbonyl)-L-allothreonine-N'-(p-nitrobenzyloxycarbonylmethoxy)amide.

Melting point, 141°–143° C.
IR (KBr) cm$^{-1}$: 3,330, 1,755, 1,670, 1,530, 1,350.
NMR (d$_6$-DMSO)δ: 1.04(3H,d,J=6 Hz,CH$_3$), 1.35(9H,s,3xCH$_3$), 3.5–3.9(2H,m,2xCH), 4.54(2H,s,OCH$_2$COO), 4.82(1H,d, J=5 Hz,OH), 5.32(2H,s,COOCH$_2$), 6.5–6.85(1H,m,C$_3$-NH), 7.63(2H,d,J=9 Hz,aromatic proton), 8.19(2H,d,J=9 Hz, aromatic proton), 11.15(1H,br.s,CONHO)

$[\alpha]_D^{24}$ −25.5° (c=1,MeOH)

When this product is reacted with methanesulfonyl chloride in pyridine in the same manner as Reference Example 2, there is obtained N-(tert-butoxycarbonyl-O-methanesulfonyl-L-allothreonine-N'-(p-nitrobenzyloxycarbonylmethoxy)amide in a yield of 83.0%.

Melting point, 153°–155° C. (decomp.)
IR (KBr) cm$^{-1}$: 3,330, 1,750, 1,690, 1,675, 1,530, 1,350.
NMR (d$_6$-DMSO)δ: 1.29(3H,d,J=6 Hz,CH$_3$), 1.37(9H,s,3×CH$_3$), 3.95–4.3(1H,m,CH), 4.55(2H,s,OCH$_2$COO), 4.65–4.95(1H,m, CH), 5.31(2H,s,COOCH$_2$), 7.13(1H,d,J=9 Hz,BocNH), 7.63 (2H,d,J=9 Hz,aromatic proton), 8.20(2H,d,J=9 Hz,aromatic proton), 11.73(1H,br.s,CONHO).

$[\alpha]_D^{25}$ −12.0° (c=0.5MeOH)

REFERENCE EXAMPLE 18

In 20 ml of tetrahydrofuran is dissolved 1.9 g [5.4 mmole) of (3S,4S)-1-benzyloxy-3-(tert-butoxycarbonylamino)-4-methoxycarbonyl -2-azetidinone obtained in the same manner as the method described in The Journll of Organic Chemistry, 48(1983), 3556–3559, and a solution of 410 mg (10.8 mmole) of sodium borohydride in 4 ml of water is added dropwise to the solution over the 10-minute period. After the addition is completed, the reaction solution is stirred under ice-cooling for 20 minutes, and 3 ml of 3N hydrochloric acid is added to stop the reaction. 10 ml of 0.6M aqueous potassium hydrogen sulfate solution is added, followed by extraction with ethyl acetate. The extract is washed with saturated aqueous sodium hydrogen carbonate solution and aqueous sodium chloride solution successively, and dried over anhydrous magnesium sulfate. The solvent is distilled off under reduced pressure, and the residue is purified by column chromatography (silica gel, 100 g;h-hexane-ethyl acetate, 2:1, then 1:1). The fractions containing the objective compound are collected the solvent is distilled off under reduced pressure, and after ether and n-hexane are added to the residue, the resulting crystals are recovered by filtration to give 200 mg (11.4%) of (3S,4S)-1-benzyloxy-3-(tert-butoxycarbonylamino)-4-hydroxymethyl-2-azetidinone.

Melting point, 125°–126° C.

IR (KBr) cm$^{-1}$: 3,440, 3,380, 1,760, 1,520, 1,330, 1,170.

NMR (CDCl$_3$)δ: 1.43(9H,s,3×CH$_3$), 4.81(1H,d.d,J=5&10 Hz, C$_3$-H), 4.98(2H,s,N$_1$-OCH$_2$), 5.45(1H,d,J=10 Hz,C$_3$-NH), 7.40(5H,s,aromatic proton).

Elemental analysis, for C$_{16}$H$_{22}$N$_2$O$_5$

|  | C(%) | H(%) | N(%) |
| --- | --- | --- | --- |
| Calcd. | 59.62 | 6.88 | 8.69 |
| Found | 59.68 | 6.86 | 8.67 |

[α]$_D^{24}$ +50.0° (c = 0.23, CHCl$_3$)

REFERENCE EXAMPLE 19

In 6 ml of chloroform dried with molecular sieve is dissolved 390 mg (1.21 mmole) of (3S,4S)-1-benzyloxy-3-(tert-butoxycarbonylamino)-4-hydroxymethyl-2-azetidinone, and a solution of 0.11 ml (1.33 mmole) of chlorocarbonyl isocyanate in 2 ml of dried chloroform is added dropwise to the solution under ice-cooling with stirring. After the stirring under ice-cooling for 30 minutes, the same amount of chlorocarbonyl isocyanate is furthermore added to the reaction solution in the same manner. After the stirring under ice-cooling for further 30 minutes, 10 ml of saturated aqueous sodium hydrogen carbonate solution is added to the reaction solution. The chloroform is distilled off under reduced pressure, and 10 ml of 3N hydrochloric acid and ethyl acetate are added to the residue, followed by thorough shaking. The ethyl acetate layer is separated, while the aqueous layer is extracted again with ethyl acetate, and the ethyl acetate layers are combined, washed with aqueous sodium chloride solution, dried over anhydrous magnesium sulfate and concentrated under reduced pressure. Ether and n-hexaneare added to the residue, and the resulting crystals are recovered by filtration to give 320 mg of (3S,4S)-1benzyloxy-3-(tert-butoxycarbonylamino)-4-carbamoyloxymethyl-2azetidinone.

Melting point, 175°–179° C. (decomp.)

IR(KBr) cm$^{-1}$: 3,440, 3,350, 1,790, 1,710, 1,615, 1,530, 1,325.

NMR (d$_6$-DMSO)δ: 1.38(9H,s,3×CH$_3$), 4.80(1H,d.d,J=5&10 Hz, C$_3$-H), 4.92(2H,s,N$_1$-OCH$_2$), 7.40(5H,s,aromatic proton).

Elemental analysis, for C$_{17}$H$_{23}$N$_3$O$_6$

|  | C(%) | H(%) | N(%) |
| --- | --- | --- | --- |
| Calcd. | 55.88 | 6.34 | 11.50 |
| Found | 56.04 | 6.17 | 11.54 |

REFERENCE EXAMPLE 20

In 10 ml of methanol is suspended 900 mg (2.46 mmole) of (3S,4S)-1-benzyloxy-3-(tert-butoxycarbonylamino)-4-carbamoyloxymethyl-2-azetidinone, and 100 mg of 10% palladium-charcoal is added to the solution, followed by stirring under a hydrogen atmosphere at room temperature for 1 hour. The catalyst is filtered off, and the filtrate is concentrated to dryness under reduced presuure to give 680 mg of (3S,4S)-3-(tert-butoxycarbonyl- amino)-4-carbamoyloxymethyl-1-hydroxy-2-azetidinone as colorless powder.

Melting point, 145°–148° C. (decomp.)

IR (KBr) cm$^{-1}$: 3,420, 3,330, 1,775, 1,700, 1,525, 1,370, 1,325.

NMR (d$_6$-DMSO)δ: 1.40(9H,s,3×CH$_3$), 4.77(1H,d.d,J=5&10 Hz, C$_3$-H), 7.47(1H,d,J=10 Hz,C$_3$-NH).

[α]$_D^{23}$ +59.7° (c=0.35,MeOH).

REFERENCE EXAMPLE 21

In 60 ml of tetrahydrofuran is dissolved 5.95 g (17 mmole) of trans-1-benzyloxy-3-(tert-butoxycarbonylamino)-4-methoxycarbonyl-2-azetidinone obtained in the same manner as the method described in The Journal of Organic Chemistry, 48 (1983), 3556–3559, and a solution of 965 mg (25.5 mmole) of sodium borohydride in 15 ml of water is added dropwise to the solution under cooling at −15° C. with stirring over the period of 10 minutes. After the addition is completed, the reaction solution is stirred at −5° to −10° C. for 40 minutes, and acetic acid is added to decompose excess sodium borohydride. 100 ml of ethyl acetate and 30 ml of aqueous sodium chloride solution are added, and the mixture is shaken, followed by separation of the ethyl acetate layer. The aqueous layer is extracted again with ethyl acetae, and the ethyl acetate layer are combined, washed with saturated aqueous sodium hydrogen carbonate solution and aqueous sodium chloride solution successively, and dried over anhydrous megnesium sulfate. The solvent is distilled off under reduced pressure, and the residue i purified by column chromatography (silica gel, 250 g; n-hexabeethyl acetate =3:2, then 1:1). The fractions containing the objective compound are collected, and the solvent is distilled off under reduced pressure. Ether and petroleum ether (1:2) are added to the residue, and the resulting crystals are recovered by filtration to give 1.33 g (24.3%) of trans-1-benzyloxy-3-(tert-butoxycarbonylamino)-4-hydroxymethyl-2-azetidinone.

Melting point, 110°–112° C.

IR (KBr) cm$^{-1}$: 3,380, 3,330, 1,750, 1,710, 1,535, 1,310, 1,260.

NMR (d$_6$-DMSO)δ: 1.38(9H,s,3xCH$_3$), 4.92(2H,s,N$_1$-OCH$_2$)

Elemental analysis, for C$_{16}$H$_{22}$N$_2$O$_5$

|  | C(%) | H(%) | N(%) |
| --- | --- | --- | --- |
| Calcd. | 59.62 | 6.88 | 8.69 |
| Found | 59.86 | 6.76 | 8.46 |

REFERENCE EXAMPLE 22

In 42 ml of dichloromethane is dissolved 2.25 g (7.0 mmole) of trans-1-benzyloxy-3-(tert-butoxycarbonylamino)-4-hydroxymethyl2-azetidinone, and a solution of 0.68 ml (8.4 mmole) of chlorocarbonyl isocyanate in 14 ml of dichloromethane is added to the solution under cooling at −60° C. with stirring over the period of 35 minutes, followed by stirring at −60° to −30° C. for 1 hour. A solution of 0.08 ml (1 mmole) of chlorocarbonyl isocyanate in 1 ml of dichloromethane ss furthermore added, followed by stirring at the above-mentioned temperature for further 30 minutes. 20 ml of saturated aqueous sodium hydrogen carbonate solution is added to the reaction solution, and the dichloromethane is distilled off under reduced pressure. 150 ml of ethyl acetate is added to the residual solution, and the mixture is adjusted, under ice-cooling, to pH 2 to 3 with 10% aqueous potassium hydrogen sulfate solution. The ethyl acetate layer is separated, washed with aqueous sodium chloride solution, aqueous sodium hydrogen carbonate solution and aqueous sodium chloride solution successively, and dried over anhydrous magnesium sulfate. The solvent is distilled off under reduced pressure, and the residue is purified by column chromatography (silica gel, 330 g; n-hexane:ethyl acetate=1:1, then 1:2). The fractions containing the objective compound are collected, and the solvent is distilled off under reduced pressure. Ether and n-hexane are added to the residue, and the resulting powder is recovered by filtration to give 1.72 g (74.6%) of trans-1-benzyloxy-3-(tert-butoxycarbonylamino)-4-carbamoyloxymethyl-2-azetidinone.

IR (KBr) cm$^{-1}$: 3,460, 3,360, 1,790, 1,710, 1,690, 1,530.

NMR (d$_6$-DMSO)$\delta$: 1.38(9H,s,3×CH$_3$), 4.90(2H,s,N$_1$-OCH$_2$).

Elemental analysis, for C$_{17}$H$_{23}$N$_3$O$_6$

|  | C(%) | H(%) | N(%) |
|---|---|---|---|
| Calcd. | 55.88 | 6.34 | 11.50 |
| Found | 56.01 | 6.39 | 11.27 |

REFERENCE EXAMPLE 23

In 50 ml of methanol is dissolved 1.83 g (5 mmole) of trans-1-benzyloxy-3-(tert-butoxycarbonylamino)-4-carbamoyloxymethyl-2-azetidinone, and 190 mg of 10% palladium-charcoal is added to the solution, followed by stirring under a hydrogen atmosphere at room temperature for 30 minutes. The catalyst is filtered off, and the filtrate is concentrated under reduced pressure to give 1.32 g (96.1%) of trans-3-(tert-butoxycarbonylamino)-4-carbamoyloxymethyl-1-hydroxy-2-azetidinone as a colorless foamy product.

IR (Kbr) cm$^{-1}$: 3,380, 1,770, 1,710, 1,530, 1,370, 1,165.

NMR (d$_6$-DMSO)$\delta$: 1.38(9H,s,3×CH$_3$), 7.48(1H,d,J=8 Hz,C$_3$-NH).

REFERENCE EXAMPLE 24

In ethyl acetate is suspended 8.0 g (50 mmole) of O-benzylhydroxylamine hydrochloride, which is dissolved by adding 5 ml of 2N aqueous sodium hydroxide solution under ice-cooling. After the salting out with sodium chloride, the ethyl acetate layer is separated, and the aqueous layer is extracted again with ethyl acetate. The ethyl acetate layers are combined, washed with aqueous sodium chloride solution, and dried over anhydrous sodium sulfate. The solvent is distilled off under reduced pressure, and 11.2 g (45 mmole) of DL-threo-N-(tert-butoxycarbonyl)-3-hydroxyasparagine and 250 ml of tetrahydrofuran are added to the residue. 7.65 g (50 mmole) of 1-hydroxybenzotriazole and 10.3 g (50 mmole) of dicyclohexylcarbodiimide are added to the mixture under ice-cooling with stirring, followed by stirring at room temperature for 22 hours. The reaction solution is filtered, and the filtrate is concentrated under reduced pressure. A mixed solution (2:1) of ethyl acetate and tetrahydrofurane and water are added to the residue, followed by shaking. The organic layer is separated, washed with aqueous sodium chloride solution and dried over anhydrous magnesium sulfate. The solvent is distilled off under reduced pressure, and ethyl acetate and hexane (2:1) are added to the solidified residue, followed by filtration to give 12.5 g (78.4%) of DL-threo-N$^\alpha$-benzyloxy-N-(tert-butoxycarbonyl)-3-hydroxyaspartic acid diamide as colorless crystals.

Melting point, 147°–150° C.

IR (KBr) cm$^{-1}$: 3,470, 3,380, 3,270, 1,695, 1,675, 1,630, 1,500.

NMR (d$_6$-DMSO)$\delta$: 1.35(9H,s,3×CH$_3$), 4.78(2H,s,CH$_2$), 7.38 (5H,s,aromatic proton).

REFERENCE EXAMPLE 25

In 60 ml of pyridine is dissolved 10.6 g (30 mmole) of DL-threo-N$^\alpha$-benzyloxy-N-(tert-butoxycarbonyl)-3-hydroxyaspartic acid diamide, and 3.02 ml (39 mmole) of methanesulfonyl chloride is added dropwise to the solution at −20° C. After the addition is completed, stirring is continued at 3° to 5° C. for 15 hours, and a mixed solution (2:1) of ethyl acetate and tetrahydrofran and 5N hydrochloric acid are added to the reaction solution to make the solution acidic. The organic layer is separated, and the aqueous layer is extracted again with a mixed solution (4:1) of ethyl acetate and tetrahydrofuran. The organic layers are combined, washed with aqueous sodium chloride solution, aqueous sodium hydrogen carbonate solution and aqueous sodium chloride ssolution successively, and dried over anhydrous magnesium sulfate, followed by concentration under reduced pressure. Ethyl acetate and n-hexane (1:1) are added to the residue, and the resulting crystals are recovered by filtration and washed with ether to give 7.3 g (56.5%) of DL-threo-N$^\alpha$-benzyloxy-N-(tert-butoxycarbonyl)-3-methanesulfonyloxyaspartic acid diamide as colorless crystals.

Melting point, 133°–136° C. (decomp.)

IR (KBr) cm$^{-1}$: 3,430, 3,320, 1,680, 1,665, 1,630, 1,525, 1,370.

NMR (d$_6$-DMSO)$\delta$: 1.38(9H,s,3×CH$_3$), 3.17(3H,s,SO$_2$CH$_3$), 4.53 (1H,d.d,J-4&10 Hz,C$_2$-H), 3.78(2H,s,CH$_2$), 5.08(1H,d,J=4 Hz, C$_3$-H), 6.65(1H,d,J=10 Hz,C$_2$-NH), 7.37(5H,s,aromatic proton).

REFERENCE EXAMPLE 26

In 1.5 l of acetone are suspended 6.465 g (15 mmole) of DL-threo-N$^{n\alpha}$-benzyloxy-N-(tert-butoxycarbonyl)-3-methanesulfonyloxyaspartic acid diamide and 6.21 g (45 mmole) of potassium carbonate, and the suspension is gradually warmed under a nitrogen atmosphere until its temperature reaches 60° C. over the period of 15 minutes, followed by stirring at the same temperature for 40 minutes. The reaction solution is filtered, and the filtrate is concentrated under reduced pressure. The residue is dissolved in a mixed solution (3:1) of ethyl acetate and tetrahydrofuran, and solution is washed with dilute hydrochloric acid, aqueous sodium chloride solution, aqueous sodium hydrogen carbonate solution and aqueous sodium chloride solution successively, and dried over anhydrous magnesium sulfate. The solvent is distilled off under reduced pressure, and after ethyl acetate and n-hexane (1:1) are added to the residue, the resulting crystals are recovered by filtration and washed with ether to give 4.48 g (89.1%) of trans-1-benzyloxy-3-(tert-butoxycarbonylamino)-4-carbamoyl-2-azetidinone as colorless crystals.

Melting point, 172°–175° C.

IR (KBr) cm$^{-1}$: 3,380, 1,790, 1,780, 1,695, 1,630, 1,535.

NMR (d6-DMSO)δ: 1.39(9H,s,3×CH3), 4.95(2H,s,N1-OCH2), 7.37(5H,s,aromatic proton), 7.65(1H,d,J=9 Hz,C3-NH).

REFERENCE EXAMPLE 27

In 200 ml of methanol is suspended 3.69 g (11 mmole) of trans-1-benzyloxy-3-(tert-butoxycarbonylamino)-4-carbamoyl-2-azetidinone, and 350 mg of 10% palladium-charcoal is added to the suspension, followed by stirring under a hydrogen atmosphere at room temperature for 30 minutes. The catalyst is filtered off, and the filtrate is concentrated to dryness under reduced pressure to give 2.7 g of trans-3-(tert-butoxycarbonylamino)-4-carbamoyl-1-hydroxy-2-azetidinone as a yellowish foamy product.

IR (KBr) cm$^{-1}$: 3,330, 1,780, 1,690, 1,630, 1,530, 1,165.

NMR (d6-DMSO)δ: 1.39(9H,s,3×CH3), 4.06(1H,d,J=1.5 Hz,C4-H), 4.24(1H,d.d,J=1.5&9 Hz,C3-H), 7.65(1H,d,J=9 Hz,C3-NH).

REFERENCE EXAMPLE 28

In N,N-dimethylformamide (200 ml) ar dissolved 24.5 g (0.15 mole) of N-hydroxyphthalimide and 29.3 g (0.15 mole) of tert-butyl bromoacetate, and 20.7 g (0.15 mole) of powdered potassium carbonate is added to the solution under ice-cooling with stirring. The reaction solution is stirred under ice-cooling for 30 minutes and then at room temperature for 20 hours, and poured into 2 l of ice cold water. The crystals that separate out are recovered by filtration, washed with 1 l of water and 500 ml of hexane successively and dried under reduced pressure at 40° C. to give 39.7 g (95.5%) of N-(tert-butoxycarbonylmethoxy)phthalimide as colorless crystals. This product is to be used in the subsequent reaction, and part of this product, when recrystallized from etyyl acetate-n-hexane (1:2), exhibits a melting point of 145°-146° C.

IR(KBr) cm$^{-1}$: 1,790, 1,750, 1,730, 1,380, 1,250, 1,140.

NMR (CDCl3)δ: 1.51(9H,s,3xCH3), 4.72(2H,s,CH2).

Elemental analysis, for $C_{14}H_{15}NO_5$

|  | C(%) | H(%) | N(%) |
|---|---|---|---|
| Calcd. | 60.64 | 5.45 | 5.05 |
| Found | 60.72 | 5.40 | 4.99 |

REFERENCE EXAMPLE 29

In 1.35 l of dichloromethane is dissolved 37.4 g (0.135 mole) of N-(tert-butoxycarbonylmethoxy) phthalimide, and 9.21 ml (0.189 mole) of hydrazine hydrate is added dropwise to the solution over the period of 10 minutes, followed by stirring at room temperature for 2 hours. 3.95 ml (0.081 mole) of hydrazine hydrate is furthermore added, followed by stirring for further 1.5 hours. The reaction solution is filtered, and the filtrate is washed with 300 ml of 2N ammonium water and aqueous sodium chloride solution successively, and dried over anhydrous sodium sulfate. The solvent is distilled off under reduced pressure to give 18.95 g (95.4%) of O-(tert-butoxycarbonylmethyl)hydroxylamine as a yellow oily product.

IR (Neat) cm$^{-1}$: 3,330, 2,980, 1,750, 1,585, 1,370, 1,230, 1,160.

NMR (CDCl3)δ: 1.49(9H,s,3×CH3), 4.10(2H,s,CH2).

REFERENCE EXAMPLE 30

In 600 ml of tetrahydrofuran are dissolved 30.4 g (0.12 mole) of N-benzyloxycarbonyl-L-threonine, 17.7 g (0.12 mole) of O-(tert-butoxycarbonylmethoxy)hydroxylamine and 20.2 g (0.132 mole) of 1-hydroxybenzotriazole, and dicyclohexylcarbodiimide (27.2 g, 0.132 mole) is added to the solution under ice-cooling with stirring, followed by stirring at room temperature for 18 hours. The precipitate is filtered off, and washed with ethyl acetate. The filtrate and washing are combined and concentrated under reduced pressure, and the residue is purified by column chromatography (silica gel, 700 g: ethyl acetate-chloroform=1:1) to give 24.0 g (52.3%) of N-benzyloxycarbonyl-N$^\alpha$-(tert-butoxycarbonylmethoxy)-L-threonine amide as a colorless gum-like product.

IR (KBr) cm$^{-1}$: 3,380, 1,750, 1,730, 1,690, 1,520, 1,250.

NMR (d6-DMSO)δ: 1.02(3H,d,J=6 Hz,CH3), 1.33(9H,s,3×CH3), 4.28(2H,s,OCH2COO), 5.02(2H,s,PhCH2O), 6.92(1H,d,J=8 Hz, C3-NH), 7.33(5H,s,aromatic proton).

Elemental analysis, for $C_{18}H_{26}N_2O_7$

|  | C(%) | H(%) | N(%) |
|---|---|---|---|
| Calcd. | 56.54 | 6.85 | 7.33 |
| Found | 56.63 | 6.96 | 7.28 |

What we claim is:

1. A 2-azetidinone compound represented by the formula

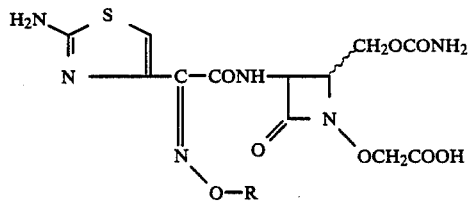

wherein R is an alkyl or carboxyalkyl group, or a pharmaceutically acceptable salt or ester thereof.

2. A 2-azetidinone compound as claimed in claim 1 wherein the substituent at the 3-position is 2-(2-aminothiazol-4-yl)-(Z)-2-carboxymethoxyiminoacetamido group, or a pharmaceutically acceptable salt or ester thereof.

3. A 2-azetidinone compound as claimed in claim 1 wherein the substituent at the 3-position is the 2-(2-aminothiazol-4-yl)-(Z)-2-(1-carboxy-1-methylethoxyiminoacetamido group, or a pharmaceutically acceptable salt or ester thereof.

4. A compound as claimed in claim 1 wherein said compound has a 4-substituent of the azetidine ring in the trans-configuration to the 3-substituent.

5. A compound as claimed in claim 1, namely (3S,4S)-3-[2-(2-aminothiazo-4-yl)-(Z)-2-carboxymethoxyiminoacetamido]-4-carbamoyloxymethyl-1-carboxymethoxy-2-azetidinone, or a pharmaceutically acceptable salt or ester thereof.

6. A compound as claimed in claim 1, namely trans-3-[2-(2-aminothiazol-4-l -yl)-(Z)-2-carboxymethoxyiminoacetamido]-4-carbamoyloxymethyl-1-carboxymethoxy-2-azetidinone, or a pharmaceutically acceptable salt or ester thereof.

7. A compound as claimed in claim 1, namely trans-3-[2-(2-aminothiazol-4-yl)-(Z)-2-(1-carboxy-1-methylethoxyimino)acetamido]-4-carbamoyloxymethyl-1-carboxymethoxy-2-azetidinone, or a pharmaceutically acceptable salt or ester thereof.

8. An antibacterial composition which comprises an antibacterially effective amount of a compound or pharmaceutically acceptable salt or ester thereof as defined in claim 1 in admixture with a pharmaceutically acceptable carrier therefor.

* * * * *